(12) United States Patent
Lu et al.

(10) Patent No.: US 9,434,741 B2
(45) Date of Patent: Sep. 6, 2016

(54) THIENO[2,3-D]PYRIMIDINE DERIVATIVES, PREPARATION METHOD AND USE THEREOF

(71) Applicants: Canzhong Lu, Fujian (CN); Jianping Yong, Fujian (CN)

(72) Inventors: Canzhong Lu, Fujian (CN); Jianping Yong, Fujian (CN)

(73) Assignee: FUJIAN INSTITUTE OF RESEARCH ON THE STRUCTURE OF MATTER, CHINESE ACADEMY OF SCIENCES, Fuzhou, Fujian (CN)

( * ) Notice: Subject to any disclaimer, the term of this patent is extended or adjusted under 35 U.S.C. 154(b) by 0 days.

(21) Appl. No.: 14/241,056

(22) PCT Filed: Sep. 19, 2012

(86) PCT No.: PCT/CN2012/081611
§ 371 (c)(1),
(2) Date: Feb. 25, 2014

(87) PCT Pub. No.: WO2014/043866
PCT Pub. Date: Mar. 27, 2014

(65) Prior Publication Data
US 2015/0080416 A1    Mar. 19, 2015

(51) Int. Cl.
| C07D 495/04 | (2006.01) |
| A61K 31/519 | (2006.01) |
| A61P 35/00 | (2006.01) |
| A61P 35/04 | (2006.01) |

(52) U.S. Cl.
CPC .................. C07D 495/04 (2013.01)

(58) Field of Classification Search
CPC ........................ C07D 495/04; A61K 31/519
See application file for complete search history.

(56) References Cited

FOREIGN PATENT DOCUMENTS

| CN | 103664991 A | 3/2014 |
| WO | 2006136402 A1 | 12/2006 |
| WO | 2009104026 A1 | 8/2009 |
| WO | 2009104027 A1 | 8/2009 |
| WO | 2010038060 A1 | 4/2010 |

OTHER PUBLICATIONS

STN Search, Downloaded Apr. 22, 2015, pp. 1-3.*
STN Printout, Aurora Fine Chemicals (registered Jun. 26, 2008, Downloaded From STN on Jul. 27, 2015).*
CAS Registry No. 1296589-04-2 (equivalent of RN 1296589-04-2 Registry, STN entry: May 18, 2011).
CAS Registry No. 1031065-97-0 (equivalent of RN 1031065-97-0 Registry, STN entry: Jun. 26, 2008).
CAS Registry No. 938387-04-3 (equivalent of RN 938387-04-3 Registry, STN entry: Jun. 22, 2007).
CAS Registry No. 931650-30-5 (equivalent of RN 931650-30-5 Registry, STN entry: Apr. 22, 2007).
CAS Registry No. 929987-29-1 (equivalent of RN 929987-29-1 Registry, STN entry: Apr. 13, 2007).
Li et al., Clin. Cancer Res., vol. 10, No. 24, 2004, pp. 8266-8274.

* cited by examiner

*Primary Examiner* — Susanna Moore
(74) *Attorney, Agent, or Firm* — Novick, Kim & Lee, PLLC; Allen Xue

(57) ABSTRACT

This disclosure provides thieno[2,3-d]pyrimidine compounds containing isoxazole heterocycle represented by formula (I), or pharmaceutically acceptable salts thereof.

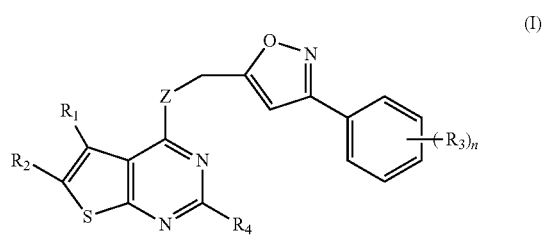

Such compounds are useful for the treatment of diseases including tumors and cancers.

11 Claims, No Drawings

THIENO[2,3-D]PYRIMIDINE DERIVATIVES, PREPARATION METHOD AND USE THEREOF

TECHNICAL FIELD

This invention relates to a class of thieno[2,3-d]pyrimidine derivatives of novel structures containing isoxazole heterocycles, pharmaceutical compositions comprising these derivatives and their uses. In particular, this class of thieno[2,3-d]pyrimidine derivatives or pharmaceutical compositions thereof possess activity to inhibit colon cancer cell lines (HCT-116) and human lung cancer cell lines (A549), and can be used as medicants or lead compounds for the treatment of tyrosine kinase related diseases, such as tumors, cancers.

BACKGROUND ART

Binding of epidermal growth factor (EGF) to epidermal growth factor receptor (EGFR) can activate tyrosine kinase activity, and thus the reactions that lead to cellular proliferation. Both overexpression and increased activity of EGFR would cause uncontrolled cell division.

The epidermal growth factor receptor tyrosine kinase (EGFR-TK) was the earliest discovered protein tyrosine kinase. It is widely distributed in various human tissue cell membranes, and overexpresses in most of tumors (e.g. bladder cancer, non-small cell lung cancer, ovarian cancer, breast cancer, stomach cancer, esophageal cancer). There is an adenosine triphosphate (ATP) binding site in EGFR intracellular region and EGFR inhibitors may competitively bind to the ATP binding site, and thereby inhibit EGFR phosphorylation and block the downstream signal transduction, and in turn inhibit the growth, differentiation and metastasis of tumor cells. Nowadays the targeted tumor therapy based on EGFR receptor as a target is one of active research areas in cancer treatments and has also achieved remarkable curative effect in clinical studies.

Patent WO2009/104027 discloses a series of thieno[2,3-d]pyrimidine derivatives possessing activity to inhibit tyrosine kinases; Patent WO2009/104026 discloses some thieno[2,3-d]pyrimidine derivatives possessing anticancer activity, which bear a phenylamino substituent at the 4-position. The above-mentioned documents are hereby incorporated herein by reference.

The present invention, being based on Patents WO2009/104027 and WO2009/104026, introduces isoxazole heterocycle into the nucleus of thieno[2,3-d]pyrimidine. A series of thieno[2,3-d]pyrimidine derivatives containing isoxazole heterocycles has been synthesized. Their activity to inhibit colon cancer cell lines (HCT-116) and human lung cancer cell lines (A549) in vitro has shown that the compounds possess stronger inhibitory activity to inhibit colon cancer cell lines (HCT-116) and human lung cancer cell lines (A549) at a concentration of $1 \times 10^{-4}$ M. They can be used as candidate compounds or lead compounds of antitumor and anticancer medicants.

DETAILED DESCRIPTION OF THE INVENTION

An object of this invention is to provide thieno[2,3-d]pyrimidine compounds containing isoxazole heterocycles represented by formula (I), which are used as an active ingredient possessing activity to inhibit colon cancer cell lines (HCT-116) and human lung cancer cell lines (A549). This invention is realized by the following technical solutions:

Thieno[2,3-d]pyrimidine derivatives containing isoxazole heterocycles represented by formula (I), pharmaceutically acceptable salts or solvates thereof:

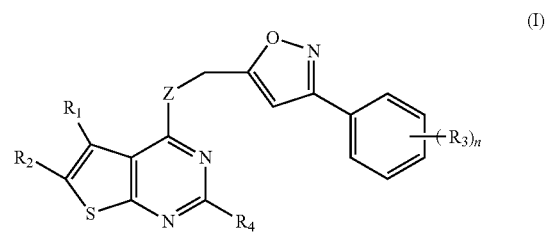

wherein: $R_1$ and $R_2$ may be the same or different and is independently to each other selected from H, $C_{1-6}$ alkyl, $C_{1-6}$ alkoxy, halo-$C_{1-6}$ alkyl, halo-$C_{1-6}$ alkoxy or hydroxyl substituted $C_{1-6}$ alkyl, aryl group optionally substituted by $R^7$ or heteroaryl group optionally substituted by $R^8$;

or $R_1$ and $R_2$ together with the carbon atoms to which they are attached, may form a 4- to 6-membered carbocyclic ring or heterocyclic ring, said carbocyclic ring or heterocyclic ring is optionally substituted by $R^{11}$; and said heterocyclic ring contains at least one heteroatom selected from N, O or S;

Z is —$NR_5$—, $C(R_6)_2$, —S— or —O—, in which $R_5$ is H or $C_{1-6}$ alkyl, and $R_6$ is the same or different, selected from H, $C_{1-6}$ alkyl, halo-$C_{1-6}$ alkyl or hydroxyl substituted $C_{1-6}$ alkyl;

$R_3$ is selected from H, halogen, $C_{1-6}$ alkyl, $C_{1-6}$ alkoxy, halo-$C_{1-6}$ alkyl, halo-$C_{1-6}$ alkoxy or hydroxyl substituted $C_{1-6}$ alkyl; n is an integer of 0-5;

$R_4$ is selected from H, $C_{1-6}$ alkyl, $C_{1-6}$ alkoxy, halo-$C_{1-6}$ alkyl or halo-$C_{1-6}$ alkoxy, aryl group optionally substituted by $R^9$, or heteroaryl group optionally substituted by $R^{10}$;

$R^7$, $R^8$, $R^9$, $R^{10}$ or $R^{11}$ independently to each other, is selected from H, hydroxy, mercapto, cyano, amino, $C_{1-6}$ alkylamino, di($C_{1-6}$ alkyl)amino, nitro, halogen, $C_{1-6}$ alkyl, $C_{1-6}$ alkoxy, $C_{1-6}$ alkylthio, carboxy, halo-$C_{1-6}$ alkyl, halo-$C_{1-6}$ alkoxy, halo-$C_{1-6}$ alkylthio, or hydroxyl substituted $C_{1-6}$ alkyl.

According to the preferred technical solutions of the present invention, in formula (I):

$R_1$ and $R_2$ may be the same or different and is independently to each other selected from H, $C_{1-6}$ alkyl, $C_{1-6}$ alkoxy, halo-$C_{1-6}$ alkyl, halo-$C_{1-6}$ alkoxy, aryl or aryl group substituted by $R^7$;

or $R_1$ and $R_2$ together with the carbon atoms to which they are attached, may form a 4- to 6-membered carbocyclic ring, which is optionally substituted by H, $C_{1-6}$ alkyl, halogen, nitro or amino;

Z is —$NR_5$—, $C(R_6)_2$, —S— or —O—, in which $R_5$ is H or $C_{1-3}$ alkyl, and $R_6$ is the same or different, selected from H, $C_{1-3}$ alkyl or hydroxyl-substituted $C_{1-3}$ alkyl;

$R_3$ is selected from H, halogen, $C_{1-6}$ alkyl, $C_{1-6}$ alkoxy, halo-$C_{1-6}$ alkyl, halo-$C_{1-6}$ alkoxy; n is an integer of 0-5;

$R_4$ is selected from H, $C_{1-6}$ alkyl, $C_{1-6}$ alkoxy, halo-$C_{1-6}$ alkyl, aryl or aryl group substituted by $R^9$.

According to the preferred technical solutions of the present invention, in formula (I):

$R_1$ and $R_2$ may be the same or different and is independently to each other selected from H, $C_{1-6}$ alkyl, $C_{1-6}$ alkoxy, halo-$C_{1-6}$ alkyl, halo-$C_{1-6}$ alkoxy, phenyl or phenyl group substituted by $R^7$, or $R_1$ and $R_2$ together with the carbon atoms to which they are attached, may form a 4- to 6-membered carbocyclic ring.

$R_4$ is selected from H, $C_{1-6}$ alkyl, $C_{1-6}$ alkoxy, halo-$C_{1-6}$ alkyl, phenyl or phenyl group substituted by $R^9$.

According to the preferred technical solutions of the present invention, $R_1$ and $R_2$ is independently to each other selected from H, $C_{1-3}$ alkyl, phenyl or phenyl group substituted by $R^7$, more preferably H, methyl, ethyl, propyl, isopropyl, butyl, isobutyl, tert-butyl or phenyl;

Z is —NH—, $CH_2$ or —O—;

$R_3$ is selected from H, fluoro, chloro, bromo, methyl, methoxy or trifluoromethyl; n is preferably 1-4, more preferably 2-3.

$R_4$ is selected from H, $C_{1-6}$ alkyl, $C_{1-6}$ alkoxy or halo-$C_{1-6}$ alkyl, phenyl or substituted phenyl group.

According to the more preferred technical solutions of the present invention, $R_1$ and $R_2$ may be the same or different and is independently to each other selected from $C_{1-6}$ alkyl, phenyl or phenyl group substituted by $R^7$, more preferably H, methyl, ethyl, tert-butyl or phenyl;

Z is —NH— or —O—;

$R_3$ is preferably at the ortho- or para-position in the isoxazole ring, more preferably being 4-fluoro, 4-chloro, 2-chloro, 4-bromo, 2,4-dichloro, 4-methyl, 4-methoxy, H, 4-trifluoromethyl or 2,4-dimethoxy;

$R_4$ is selected from H, methyl or phenyl.

According to the present invention, more preferably, $R_1$ is selected from H, methyl, phenyl; $R_2$ is selected from H, methyl, ethyl or tert-butyl.

According to the preferred technical solutions of the present invention, wherein:

$R^7$, $R^8$, $R^9$ or $R^{10}$ independently to each other, is selected from H, hydroxy, cyano, amino, $C_{1-6}$ alkylamino, di($C_{1-6}$ alkyl)amino, halogen, $C_{1-6}$ alkyl, $C_{1-6}$ alkoxy, $C_{1-6}$ alkylthio, carboxy, halo-$C_{1-6}$ alkyl, halo-$C_{1-6}$ alkoxy or halo-$C_{1-6}$ alkylthio.

Further, $R^7$, $R^8$, $R^9$ or $R^{10}$ independently to each other, is selected from H, hydroxy, mercapto, cyano, amino, halogen, $C_{1-6}$ alkyl, $C_{1-6}$ alkoxy, $C_{1-6}$ alkylthio, carboxy. Still further, $R^7$, $R^8$, $R^9$ and $R^{10}$ independently to each other, is selected from H, hydroxy, cyano, amino, halogen, $C_{1-6}$ alkyl, $C_{1-6}$ alkoxy, $C_{1-6}$ alkylthio or carboxy.

According to the present invention, said thieno[2,3-d] pyrimidine compounds represented by formula (I) are selected from any one of the following compounds.

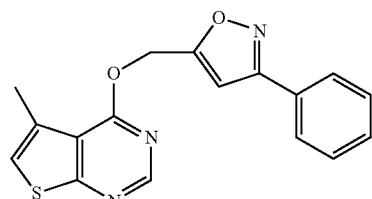

S-1

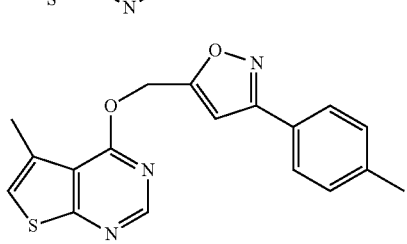

S-2

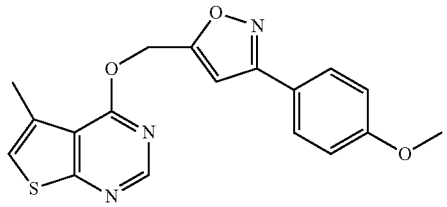

S-3

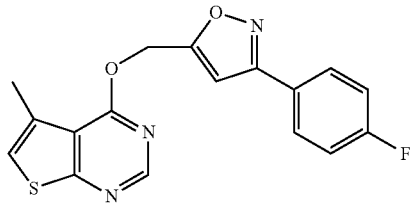

S-4

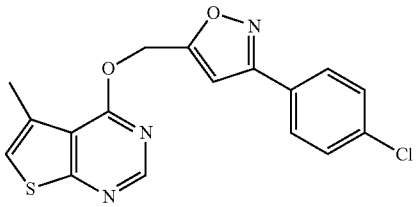

S-5

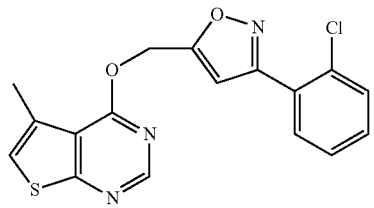

S-6

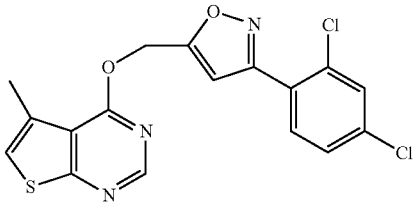

S-7

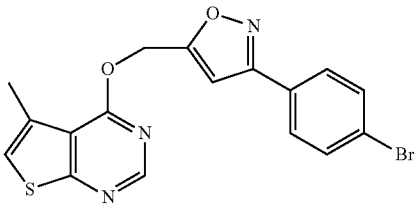

S-8

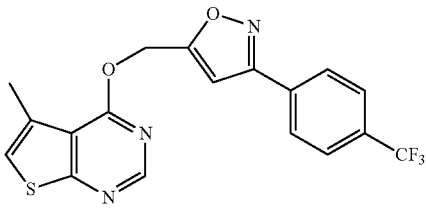

S-9

-continued
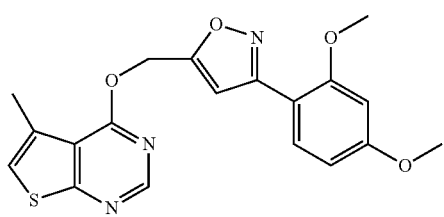
S-10
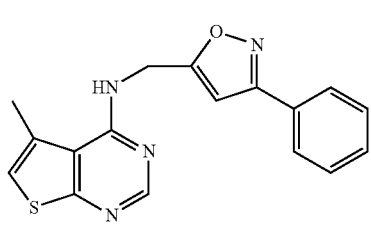
S-11
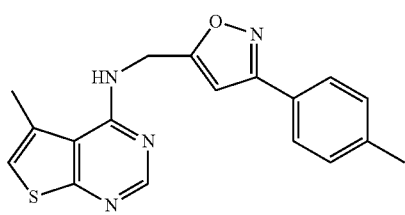
S-12
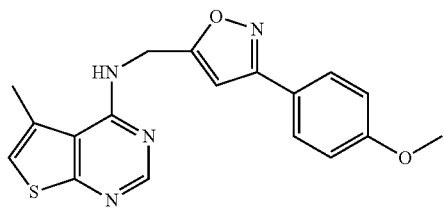
S-13
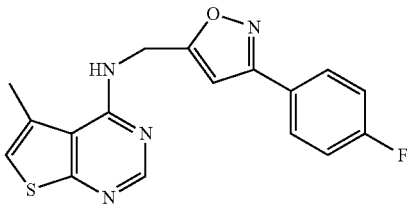
S-14
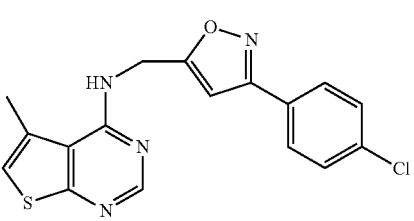
S-15
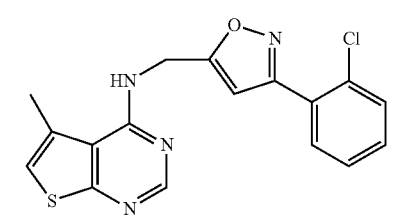
S-16
-continued
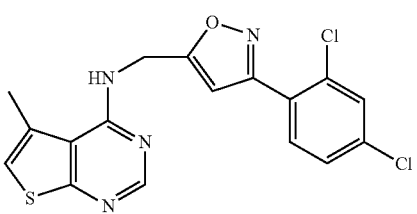
S-17
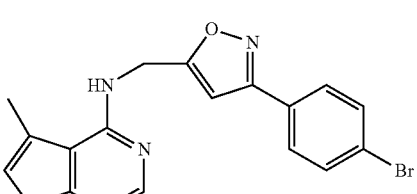
S-18
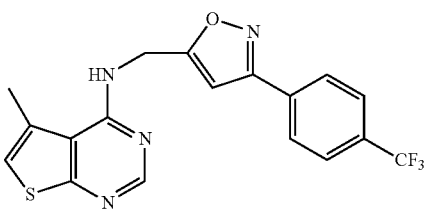
S-19
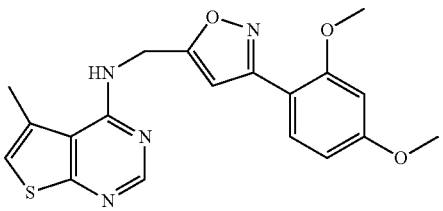
S-20
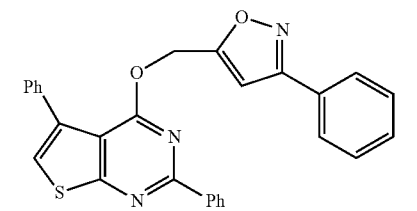
S-21
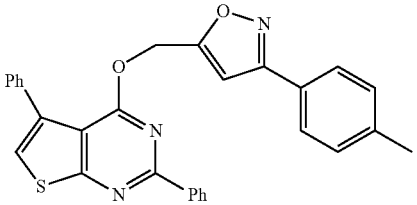
S-22
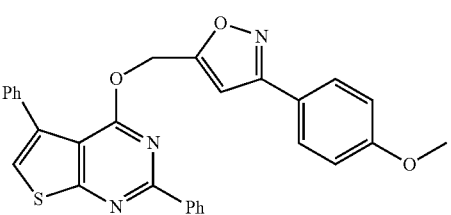
S-23

-continued

S-24

S-25

S-26

S-27

S-28

S-29

S-30

-continued

S-31

S-32

S-33

S-34

S-35

S-36

S-37

S-38 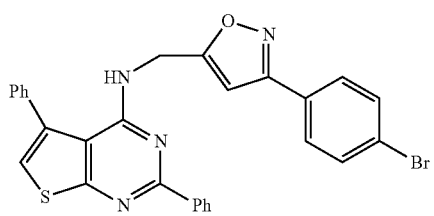
S-39 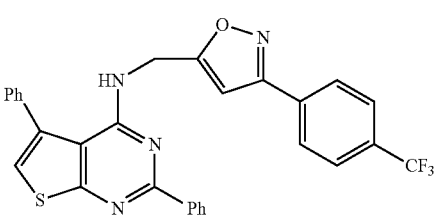
S-40 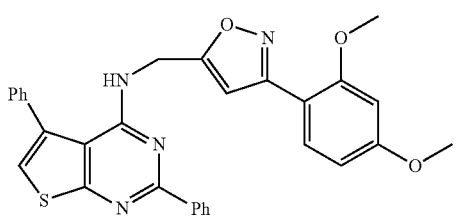
S-41 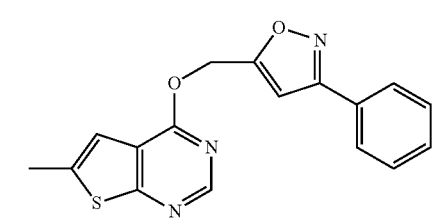
S-42 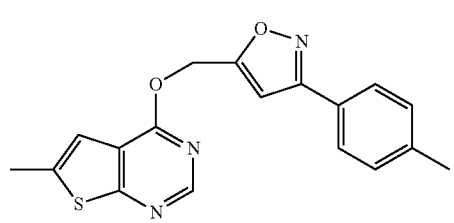
S-43 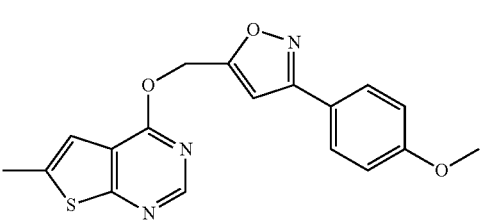
S-44 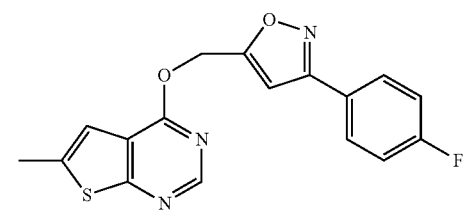
S-45 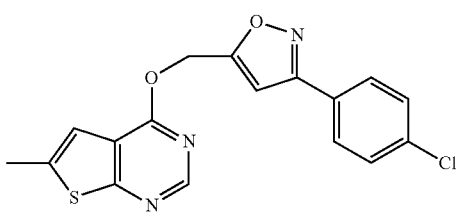
S-46 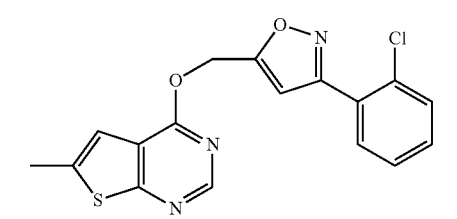
S-47 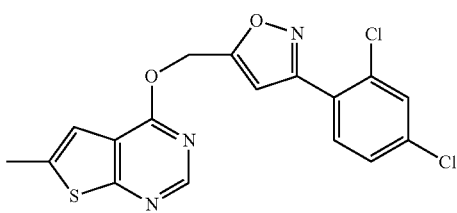
S-48 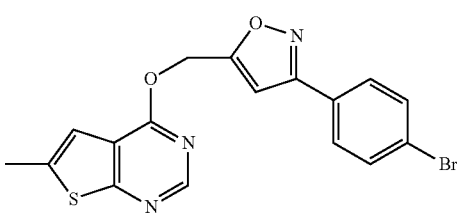
S-49 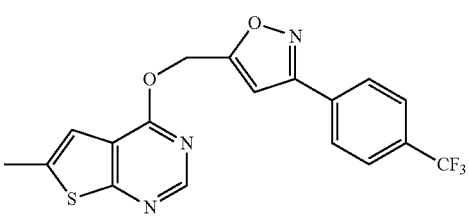
S-50 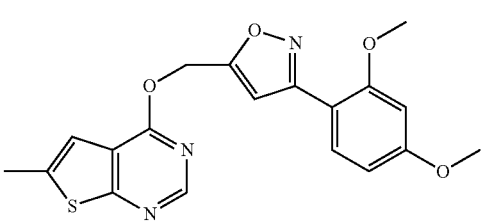
S-51 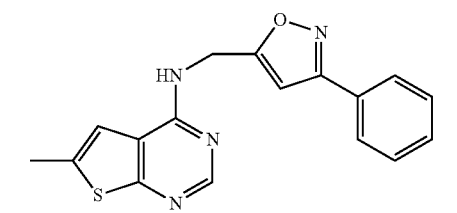

S-52
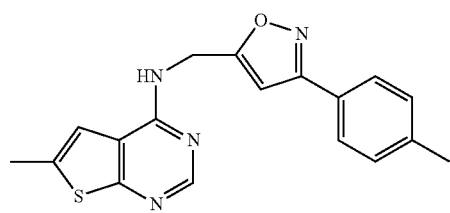
S-53
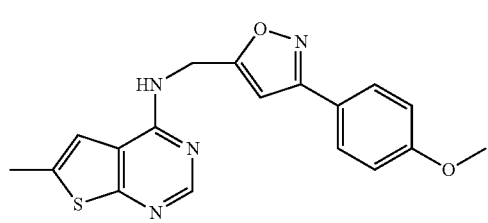
S-54
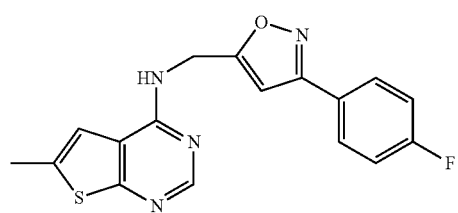
S-55
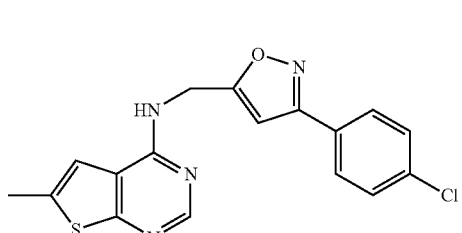
S-56
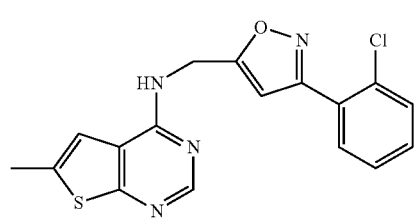
S-57
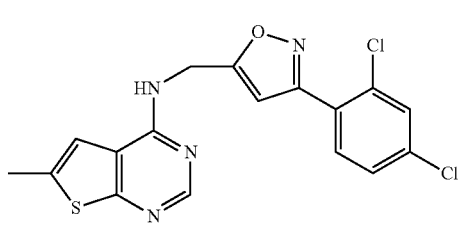
S-58
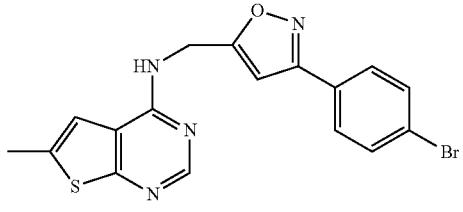
S-59
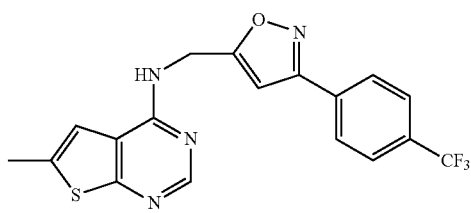
S-60
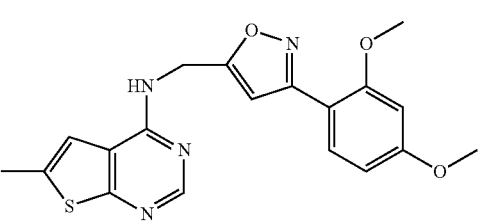
S-61
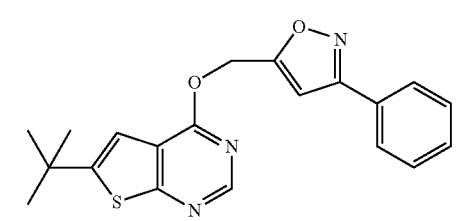
S-62
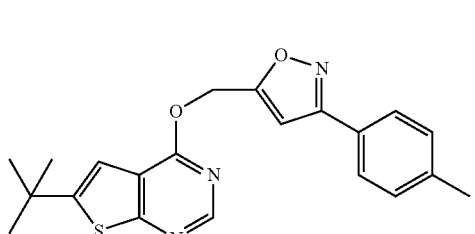
S-63
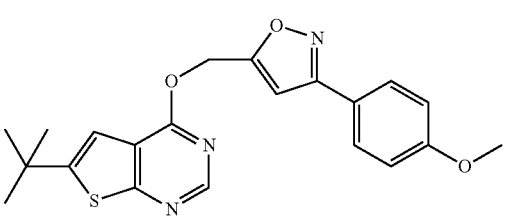
S-64
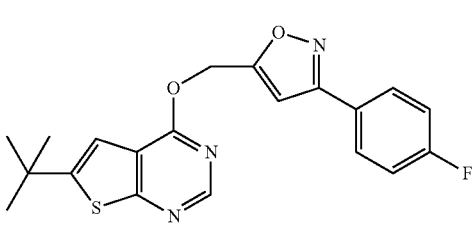
S-65
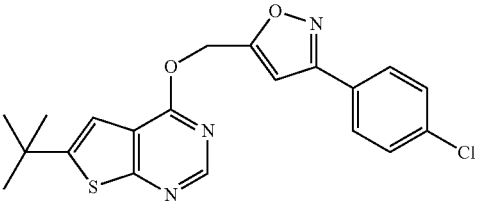

| | |
|---|---|
| S-66 | S-73 |
| S-67 | S-74 |
| S-68 | S-75 |
| S-69 | S-76 |
| S-70 | S-77 |
| S-71 | S-78 |
| S-72 | S-79 |

-continued
S-80
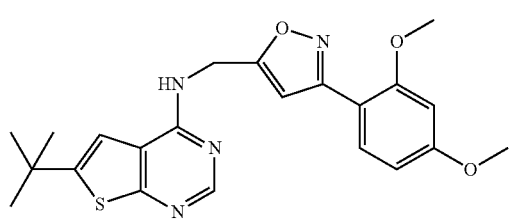
S-81
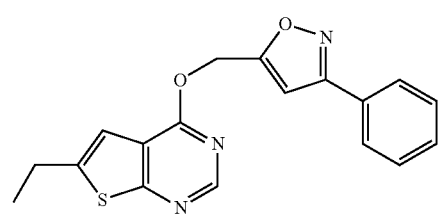
S-82
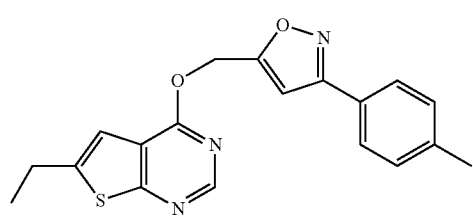
S-83
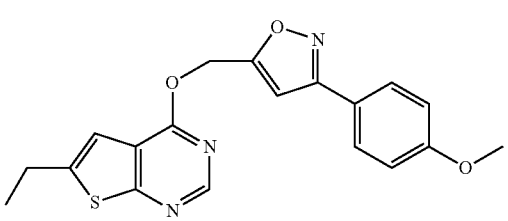
S-84
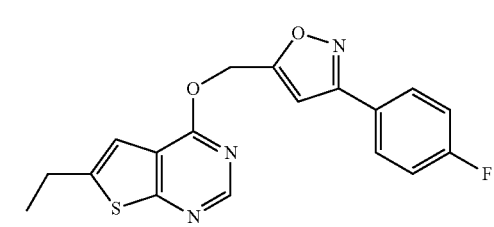
S-85
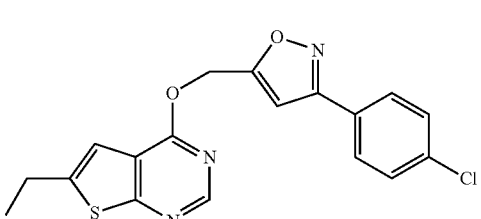
S-86
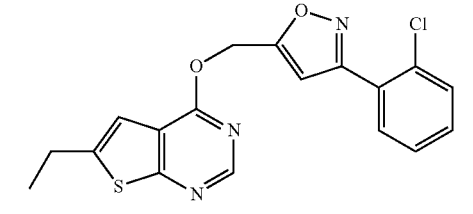
-continued
S-87
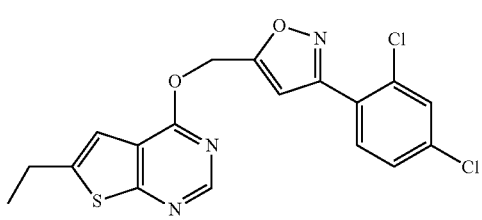
S-88
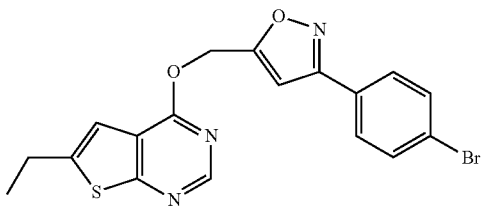
S-89
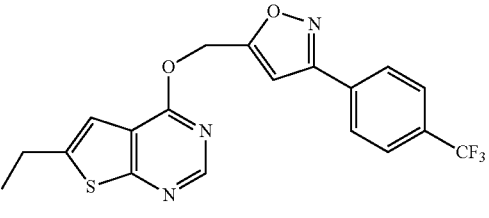
S-90
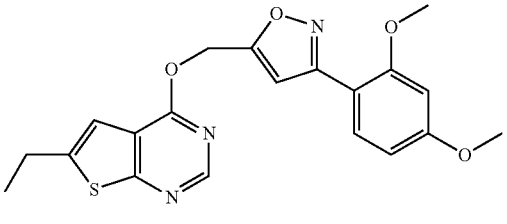
S-91
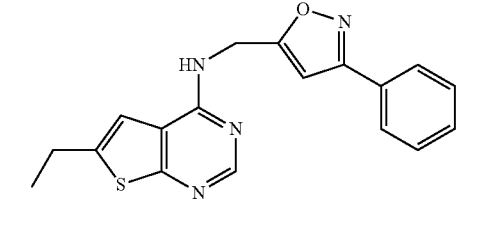
S-92
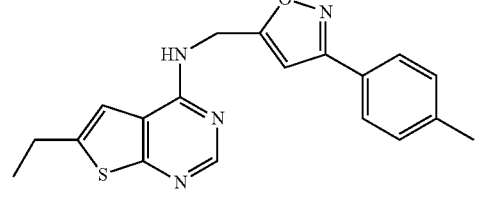
S-9
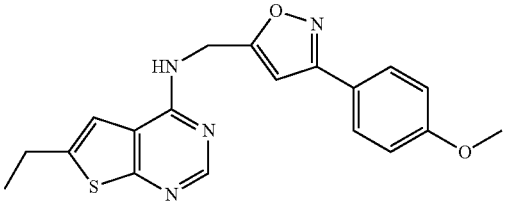

17
-continued
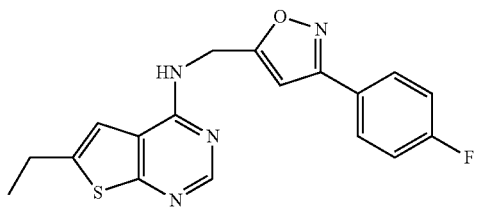
S-94
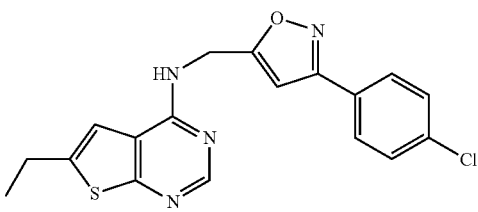
S-95
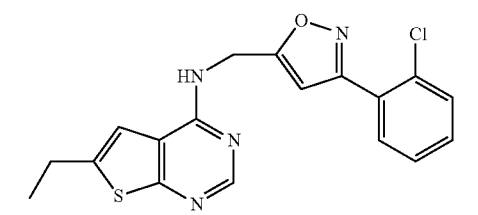
S-96
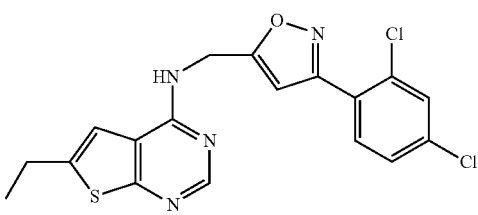
S-97
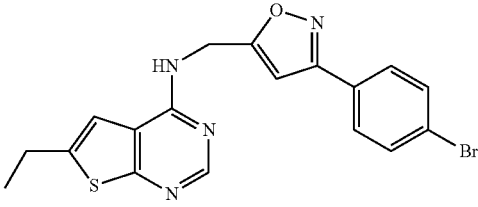
S-98
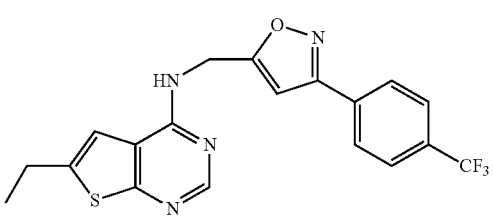
S-99
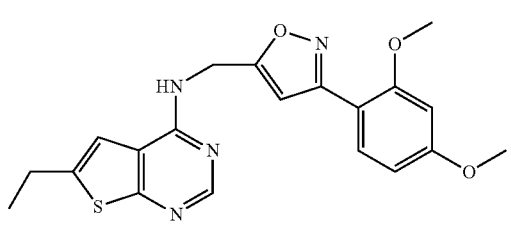
S-100
18
-continued
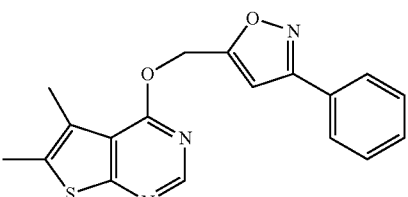
S-101
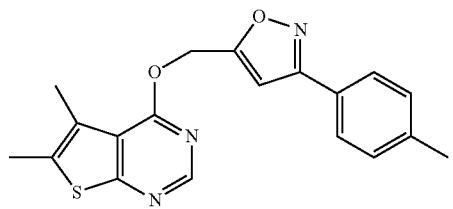
S-102
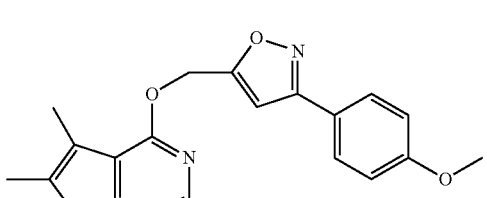
S-103
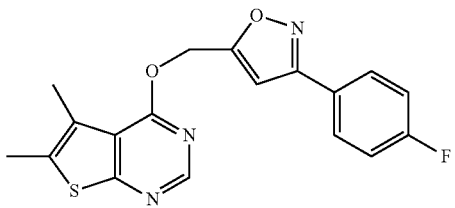
S-104
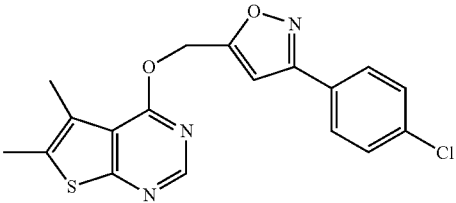
S-105
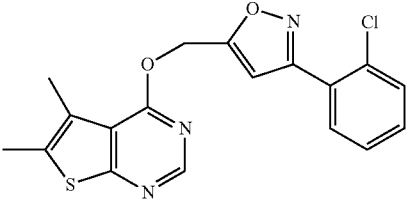
S-106
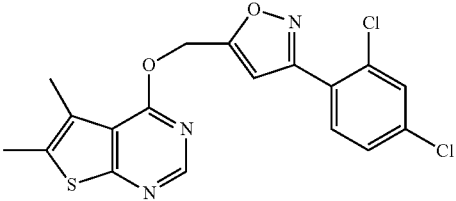
S-107

-continued

S-108, S-109, S-110, S-111, S-112, S-113, S-114, S-115, S-116, S-117, S-118, S-119, S-120, S-121

S-122 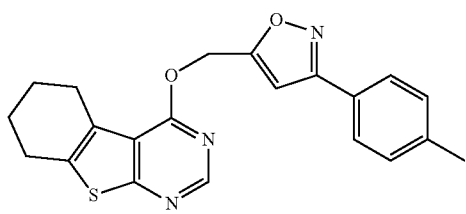
S-123 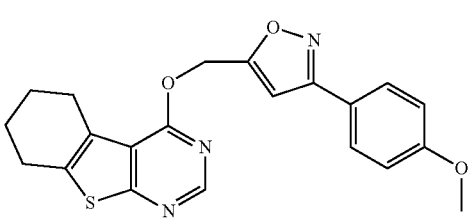
S-124 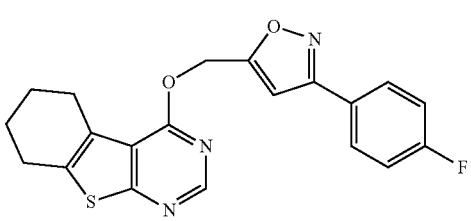
S-125 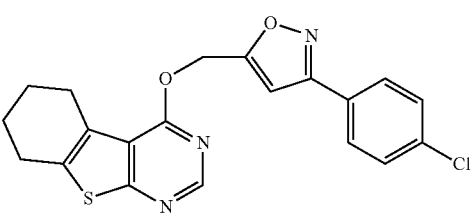
S-126 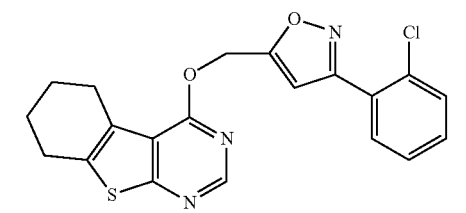
S-127 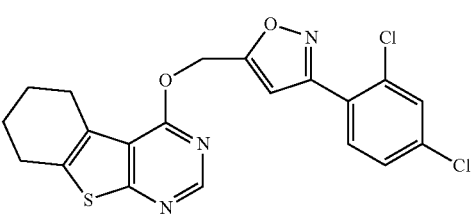
S-128 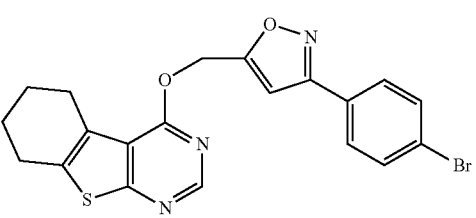
S-129 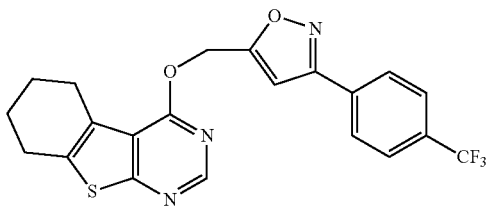
S-130 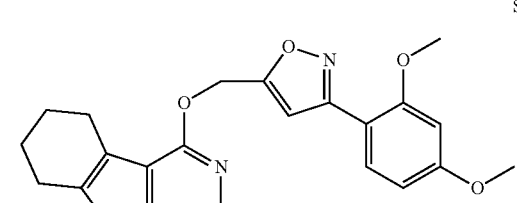
S-131 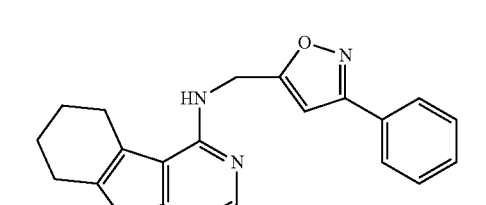
S-132 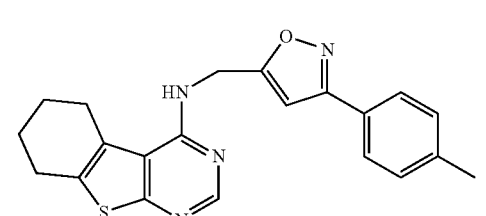
S-133 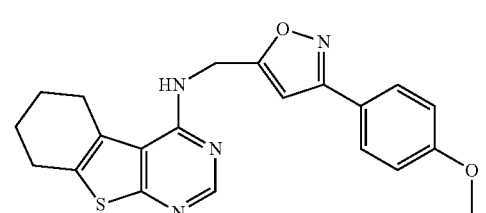
S-134 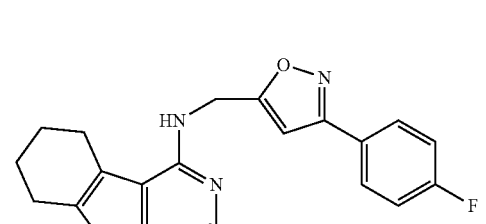
S-135 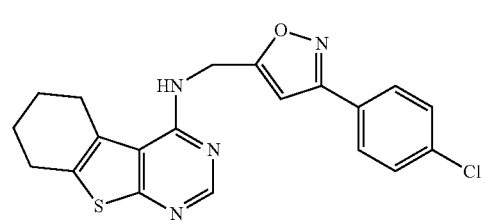

-continued

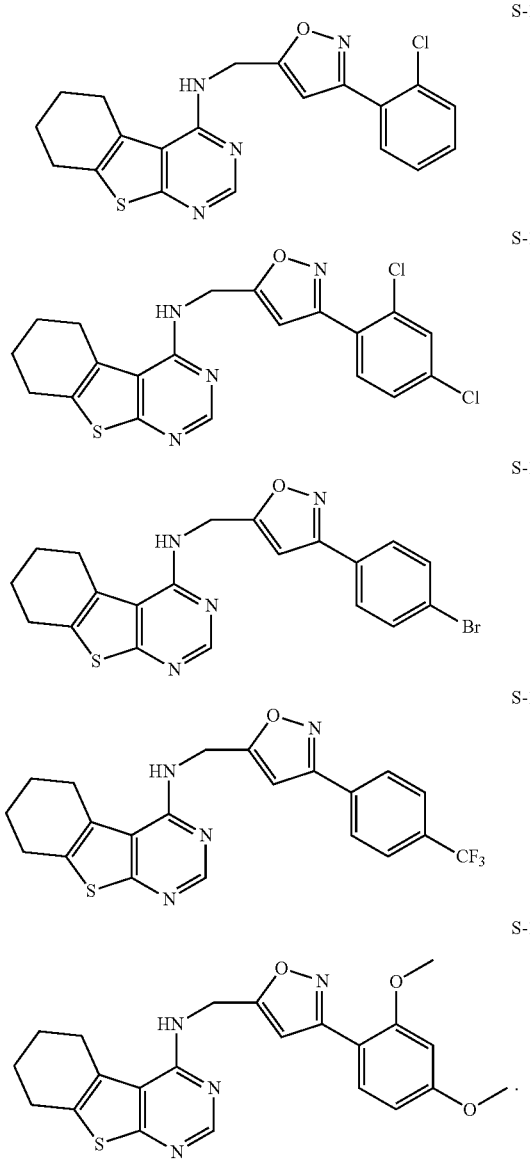

The thieno[2,3-d]pyrimidine compounds containing isoxazole heterocycles represented by formula (I) can be individually selected to form pharmaceutically acceptable salts with pharmaceutically acceptable acids, wherein the term "pharmaceutically acceptable salt" includes, but is not limited to salts formed with inorganic acids, such as hydrochloride, phosphate, diphosphate, hydrobromide, sulfate, sulfinate, nitrate, and similar salts, preferably hydrochloride, nitrate, sulfate, or phosphate; but also includes salts formed with organic acids, such as lactate, oxalate, malate, maleate, fumarate, tartrate, succinate, citrate, sulfonate, p-toluenesulfonate, 2-hydroxyethyl sulfonate, benzoate, salicylate, stearate, trifluoroacetate or amino acid salt; alkanoate, such as formate, acetate, and so on, or salts of acids of the type HOOC—$(CH_2)_n$—COOH, where n is 0-4, and similar salts. Organic acid salts are preferably selected from formate, acetate, oxalate, citrate, fumarate, maleate, malate, lactate, tartrate, p-toluenesulfonate, trifluoroacetate or amino acid salt. Similarly, pharmaceutically acceptable cations include, but are not limited to sodium, potassium, calcium, aluminum, lithium and ammonium.

The term "solvate" includes hydrates and alcoholates.

The present invention also provides a pharmaceutical composition comprising the above-described thieno[2,3-d]pyrimidine compounds represented by formula (I) or pharmaceutically acceptable salts or solvates thereof, and also at least one pharmaceutically acceptable, inert, non-toxic excipient or carrier or diluent.

According to said pharmaceutical composition, characterized in that said pharmaceutical composition further comprises one or more pharmaceutically acceptable auxiliary materials, which are sleeted from fillers, disintegrants, lubricants, glidants, effervescents, flavoring agents, preservatives and coating materials.

The present invention also provides a pharmaceutical formulation comprising the above-described thieno[2,3-d]pyrimidine compounds represented by formula (I), pharmaceutically acceptable salts or solvates thereof, and also at least one pharmaceutically acceptable, inert, non-toxic excipient or carrier or diluent.

According to the pharmaceutical formulation of the present invention, characterized in that said formulation is preferably an oral solid formulation, an oral liquid formulation or an injection.

According to the pharmaceutical formulation of the present invention, wherein said formulation is selected from tablet, dispersible tablet, enteric coated tablet, chewable tablet, orally disintegrating tablet, capsule, granule, oral solution, hydro-acupuncture for injection, lyophilized powder for injection, large volume infusion or small volume infusion.

The present invention also provides the thieno[2,3-d]pyrimidine compounds represented by formula (I) or pharmaceutically acceptable salts thereof of claim 1-4, which are used as medicant, particularly the medicants used for the effective treatment of tumors or cancers.

The present invention also provides any one of the above-described thieno[2,3-d]pyrimidine compounds represented by formula (I), pharmaceutically acceptable salts or solvates thereof used as medicants, particularly medicants for treatment of tumor by effectively inhibiting the overexpression and/or overactivity of EGFR.

The present invention also provides the use of any one of the above-described thieno[2,3-d]pyrimidine compounds represented by formula (I), pharmaceutically acceptable salts or solvates thereof in the preparation of antitumor or anticancer medicants.

According to said use of the present invention, said tumors or cancers are preferably selected from: bladder cancer, non-small cell lung cancer, ovarian cancer, breast cancer, stomach cancer, esophageal cancer, lung cancer, head and neck cancer, colon cancer, pharyngeal cancer and pancreatic cancer, and so on, more preferably non-small cell lung cancer.

According to the present invention, also provided is the use of the thieno[2,3-d]pyrimidine compounds represented by formula (I) and/or pharmaceutically acceptable salts thereof of any of claim 1-8 in the preparation of inhibitors for inhibiting the overexpression and/or overactivity of EGFR.

The present invention also provides the use of the above-described thieno[2,3-d]pyrimidine compounds represented by formula (I), and/or pharmaceutically acceptable salts or solvates thereof in the preparation of medicants for inhibiting the activity of colon cancer cell lines (HCT-116) and human lung cancer cell lines (A549).

The present invention also provides a preparation method of the thieno[2,3-d]pyrimidine compounds containing isoxazole heterocycle represented by formula (I), characterized in that said method includes the following steps:

5,6-disubustituted-4-chloro-thieno[2,3-d]pyrimidine represented by formula II and 3-substituted phenyl-5-hydroxymethyl-isoxazole represented by formula III or 3-substituted phenyl-5-aminomethyl-isoxazole represented by formula IV are reacted in a system of a dry organic solvent and an alkaline acid binding reagent to prepare the compound represented by formula (I-1) or formula (I-2):

carbonate, sodium hydride, sodium carbonate, etc. The more preferred alkaline acid binding agent is triethylamine.

Said reaction temperature is from 0° C. to reflux temperature, preferably from room temperature to reflux temperature.

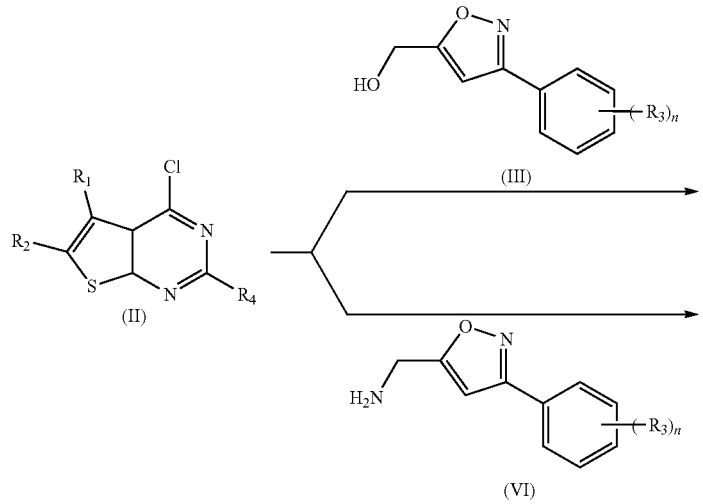

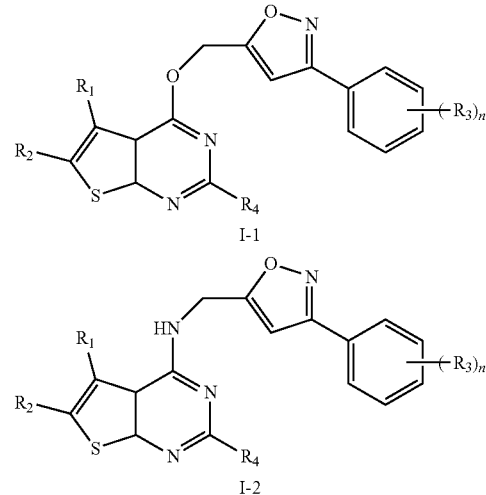

Meanwhile, with regard to the compound of formula (I) where Z in is another substituent, for example —NR$_5$ where R$_5$ is another substituent, C(R$_6$)$_2$, S, they can be prepared from formula (II) by corresponding coupling reaction with —NH(R$_5$), Cl—C(R$_6$)$_2$ or 3-substituted phenyl-5-mercapto isoxazole. 3-substituted phenyl-5-mercapto isoxazole is prepared by the synthetic procedure of formula (III) using propargyl mercaptan as a starting material.

According to the present invention, said reaction temperature is from −20° C. to reflux condition, preferably from room temperature to reflux condition.

According to the present invention, said organic solvent is aromatic hydrocarbons, halogenated hydrocarbons, $C_1$-$C_6$ lower alcohols, tetrahydrofuran or dimethyl sulfoxide (DMF). Said solvent is preferably selected from benzene, toluene, xylene, dichloromethane, chloroform, isopropanol, tetrahydrofuran or DMF, more preferably isopropanol.

According to the present invention, said alkaline acid binding reagent is an organic base or an inorganic base. Said organic base is selected from triethylamine, tripropylamine, DMAP, potassium tert-butoxide, etc. Said inorganic base is selected from potassium carbonate, sodium hydride, sodium carbonate, etc. The preferred acid binding reagent is triethylamine.

According to the present invention, the intermediate 3-substituted phenyl-5-hydroxymethyl-isoxazole of formula (III) is be prepared by the following method:

(1) substituted benzaldehyde is reacted with hydroxylamine or hydroxylamine hydrochloride in a methanol/water system under catalyzation by sodium carbonate to generate the corresponding benzaldehyde oxime;

(2) benzaldehyde oxime obtained in step (1) is reacted with propynol under the action of N-bromosuccinimide (NCS) and an alkaline acid binding agent by 1,3-dipolar cycloaddition reaction to form an isoxazole compound of formula (III).

According to the present invention, preferably, said alkaline acid binding agent is selected from an organic base or an inorganic base. Said organic base is selected from triethylamine, tripropylamine, DMAP, DMF, N-methyl morpholine, etc. Said inorganic base is selected from potassium According to the present invention, said intermediate 3-substituted phenyl-5-aminomethyl-isoxazole of formula (IV) is prepared by the following method:

(3) the isoxazole compounds of formula (III) (preferably obtained by the above-described method) is reacted with sulfonyl chloride to give the compound of formula (V);

According to the preferred technical solutions of the present invention, said sulfonyl chloride in step (3) is selected from: methanesulfonyl chloride, benzenesulfonyl chloride, substituted benzenesulfonyl chloride (such as halo benzenesulfonyl chloride, alkyl benzenesulfonyl chloride) and the like, more preferably methanesulfonyl chloride. Said reaction temperature is from −5° C. to reflux temperature, preferably from room temperature to reflux temperature. Said reaction solvent is selected from benzene, toluene, halogenated aromatic hydrocarbons, halogenated alkanes (such as chloroform, dichloromethane), tetrahydrofuran, acetonitrile and ionic liquids. More preferably, the reaction is reflux carried out in dichloromethane system.

(4) the compound of formula (V) is reacted with sodium azide, preferably in DMF system, at 60 to give the compound of formula (VI);

(5) the compound of (VI) is catalytic reduced with ammonium chloride and zinc powder, iron powder or palladium on carbon to prepare the compound of formula (IV), preferably the reaction is catalyzed by a catalyst under the condition of an inorganic acid, which is preferably hydrochloric acid or sulfuric acid, and said catalyst is preferably zinc powder and ammonium chloride.

The reaction solvent in step (5) is preferably selected from water or an organic solvent (e.g. alcohols, halogenated hydrocarbons, aromatic hydrocarbons, etc.) or mixtures thereof, preferably the reaction system of ethanol and water.

The preferred synthetic route is shown as follows:

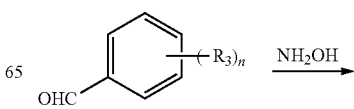

-continued

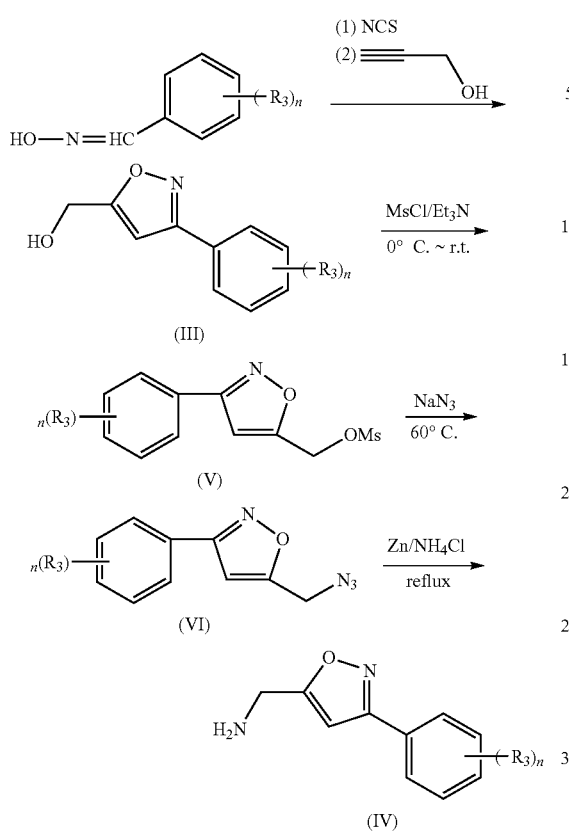

More preferably, said preparation method is as shown in the following scheme:

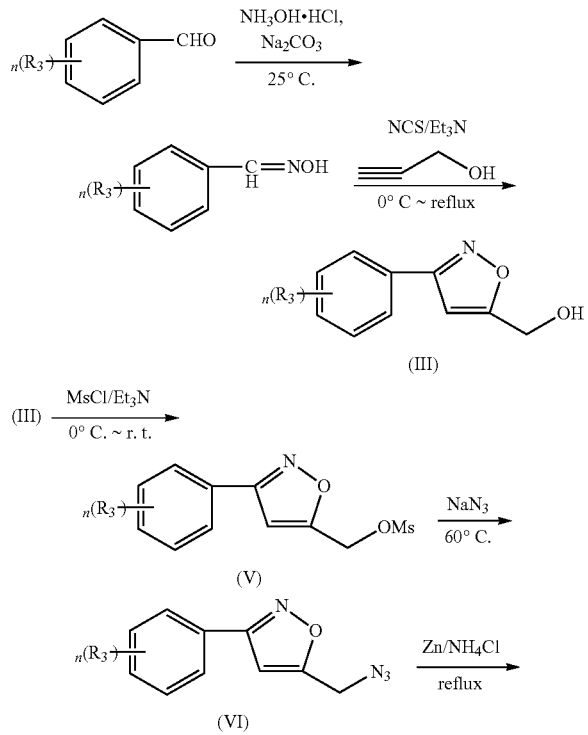

-continued

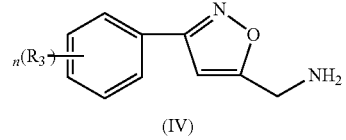

Meanwhile, with regard to the compound of formula (III) or (IV) where Z in is another substituent, for example —NR$_5$ where R$_5$ is another substituent, C(R$_6$)$_2$, S, the compound can be prepared using corresponding propynyl chloride, propargyl mercaptan.

According to the present invention, the 5,6-disubstituted-4-chloro-thieno[2,3-d]pyrimidine represented by formula (II) can be prepared by the following process:

(1) methyl 3-amino-4,5-disubstituted thiophen-2-carboxylate (VII) and formaidine acetate are reacted under the action of reagent 1 to form the compound of 5,6-disubstituted thienopyrimidinone (VIII), and preferably, said reaction temperature is from 0° C. to reflux temperature, more preferably from room temperature to reflux temperature;

(2) compound (VIII) is reacted under the action of reagent 2 to form the compound of 5,6-disubstituted-4-chloro-thieno [2,3-d]pyrimidine, and preferably, said reaction temperature is from 0° C. to reflux temperature, more preferably from room temperature to reflux temperature.

The details can be found in the following reaction scheme:

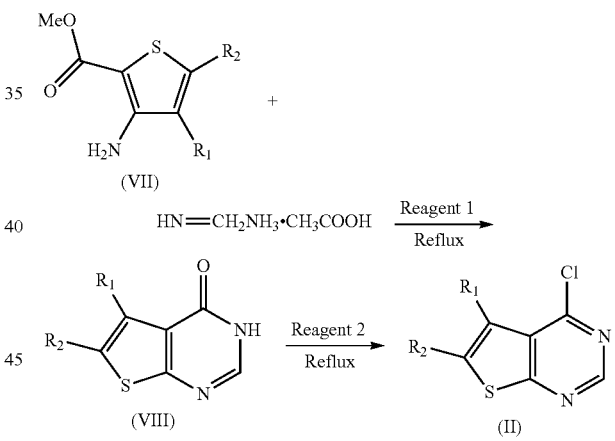

wherein Reagent 1 is selected from: benzene, toluene, ethylene glycol monomethyl ether, ethylene glycol dimethyl ether, ethylene glycol monoethyl ether, ethylene glycol diethyl ether, ethanol, 1,2-dichloroethane and ionic liquid, etc; Reagent 2 is selected from chlorinated reagents of thionyl chloride, phosphorus oxychloride, phosphorus pentachloride, etc.

According to the present invention, the preparation method of thieno[2,3-d]pyrimidine compounds containing isoxazole heterocycles represented by formula (I) is provided, characterized in that said method includes the following steps:

(1) substituted benzaldehyde is reacted with hydroxylamine or hydroxylamine hydrochloride in a methanol/water system under catalyzation by sodium carbonate, preferably at a temperature ranging from room temperature to reflux temperature, to generate the corresponding benzaldehyde oxime;

(2) benzaldehyde oxime obtained in step (1) is reacted with propynol under the action of N-bromosuccinimide (NCS) and triethylamine by 1,3-dipolar cycloaddition reaction to form an isoxazole compound of formula (III);

(3) the isoxazole compounds of formula (III) is reacted with sulfonyl chloride, preferably in dichloromethane, at room temperature to give the compound of formula (V);

(4) the compound of formula (V) is reacted with sodium azide, preferably in DMF system, at 60° C. to give the compound of formula (VI);

(5) the compound of (VI) is reacted under the catalyzation by zinc powder and ammonium chloride by reflux in ethanol/water system to prepare the compound of formula (IV);

(6) methyl 3-amino-4,5-disubstituted thiophen-2-carboxylate (VII) and formaidine acetate are reacted under the action of reagent 1 to form the compound of 5,6-disubstituted thienopyrimidinone (VIII);

(7) compound (VIII) is reacted under the action of reagent 2 to form the compound of 5,6-disubstituted-4-chloro-thieno[2,3-d]pyrimidine represented by formula II;

(8) 5,6-disubustituted-4-chloro-thieno[2,3-d]pyrimidine represented by formula II is reacted with 3-substituted phenyl-5-hydroxymethyl-isoxazole represented by formula III or 3-substituted phenyl-5-aminomethyl-isoxazole represented by formula IV in the system of a dry organic solvent and an alkaline acid binding reagent to prepare the compounds represented by formula (I-1) or formula (I-2).

If desired, the pharmaceutically acceptable salts or solvates of the compounds represented by formula (I) can be formed.

According to the present invention, said compounds represented by formula (I) include, but are not limited to their optical isomers, racemates and mixtures thereof.

According to the present invention, said halogen or the halogen atom is selected from fluoro, chloro or bromo.

According to the present invention, said alkyl group is a linear or branched alkyl group, such as $C_{1-6}$ alkyl, preferably $C_{1-3}$ alkyl, including but is not limited to methyl, ethyl, propyl, isopropyl, butyl, isobutyl, tert-butyl, n-pentyl, isopentyl, neopentyl, n-hexyl, etc.

According to the present invention, said 4- to 6-membered carbocyclic ring is selected from cyclobutyl, cyclopentyl, cyclohexyl, preferably cyclopentyl or cyclohexyl.

According to the present invention, said heterocyclic ring containing at least one heteroatom selected from N, O, S is selected from tetrahydrofuran, tetrahydrothiophene, azetidine, pyrrolidinyl, acridine, tetrahydropyrrole, 1,3-dihydrothiazole, 1,3-dihydrooxazole, piperidine, piperazine, morpholine, thiomorpholine, thiazine, preferably piperazinyl, morpholinyl or piperidinyl.

According to the present invention, said aryl group is a monocyclic or bicyclic aromatic hydrocarbon group, for example $C_{6-14}$ aryl group which is preferably phenyl or naphthyl, more preferably phenyl.

According to the present invention, said heteroaryl group is a monocyclic or bicyclic hetero aromatic hydrocarbon group, in which the ring containing heteroatoms is preferably a 5- or 6-membered heteroaryl, which comprises an aromatic ring containing at least one, preferably 1-4 heteroatoms of N, O, S. Said heteroaryl group is preferably pyridinyl, pyrimidinyl, quinolyl, isoquinolyl, quinazolinyl, quinoxalinyl, indolyl, pyrrolyl, thienyl, furyl, benzofuranyl, benzothienyl, thiazolyl, isothiazolyl, oxazolyl, isoxazolyl, pyrazolyl, furazanyl, thiadiazolyl, tetrazolyl, etc., more preferably pyrrolyl, thienyl, furyl, indolyl, benzofuranyl.

The term "effective amount" refers to the amount of at least one compound and/or at least one pharmaceutically acceptable salt that is effective for the "treatment" of the disease or discomfort of an individual. In case of cancer, an effective amount may reduce the number of cancer or tumor cells, reduce the size of the tumor, inhibit or prevent the tumor cell infiltration into surrounding organs, for example, the extension of tumors into soft tissue or bone; inhibit or prevent tumor metastasis; inhibit or prevent tumor growth; alleviate one or more symptoms associated with the cancer to an extent; reduce morbidity and mortality; improve quality of life; or a combination of the above effects. An effective amount may be an amount for reducing a symptoms of a disease via inhibiting EGFR activity. For cancer therapy, effect of in vivo experiments can be determined by assessing such as the duration of survival, time to disease progression (TTP), response rates (RR), the duration of sustained response and/or quality of life. An effective amount may vary, as recognized by those professionals, with a route of administration, excipient usage, and co-usage with other medicants.

The term "effective amount" may also refer to the dosage of at least one said compound and/or at least one pharmaceutically acceptable salt that is effective to inhibit the overexpression and/or overactivity of EGFR.

The compounds of the present invention possess antitumor or anticancer activity, particularly against colon cancer cell lines (HCT-116) and human lung cancer cell lines (A549). All of the compounds of the present invention possess inhibitory activity at a concentration of $1\times10^{-4}$ M. The inhibitory activity of the compounds in examples can reach more than 50%, preferably more than 60%, more preferably more than 80%. Among them, most of the compounds possess stronger inhibitory activity against colon cancer cell lines (HCT-116) and human lung cancer cell lines (A549). For example, the inhibitory ratio of compound S-101 at a concentration of $1\times10^{-4}$ M is 68.8% against colon cancer cell lines (HCT-116) and 88% against human lung cancer cell lines (A549). The inhibitory ratio of the compound S-3 at a concentration of $1\times10^{-4}$ M is 70% against colon cancer cell lines (HCT-116), and 86.4% against human lung cancer cell lines (A549). The inhibitory ratio of the compound S-83 at a concentration of $1\times10^{-4}$ M reaches 89.4% against human lung cancer cell lines (A549). Therefore, the compounds of the present invention can be used as medicant candidates or lead compounds for treatment of tumors and cancers.

SPECIFIC MODE FOR CARRYING OUT THE INVENTION

Hereinafter, the present invention will be further illustrated with reference to the examples. It should be noted that the compounds in the examples do not constitute a limitation of the perfection scope of the present invention. Any improvement and modification based on the present invention would not depart from the spirit of the present invention.

Wherein, the synthetic processes of intermediates and target compounds are representatively illustrated based on those in the examples, and the synthetic processes of the other intermediates and target compounds are the same as those of the representative compounds.

Instruments and Reagents

AVANCE III nuclear magnetic resonance spectrometer (400 MHz, DMSO-$d_6$, TMS as an internal standard), ion trap LC-MS spectrometer (DECAX-30000 LCQ Deca XP), Shimadzu FTIR-8400S (Shimadzu Corporation, Japan), XT5 digital displaying micro melting point detector (manufactured by Beijing Keyi electro-optical Instrument Plant, temperature uncorrected), wavelength-tunable microplate reader (Molecular Devices SPECTRAMAX190). All chemical reagents are commercially available reagents with analytical or chemically purity. RPMI1640 is commercially available from Gibco, Sulforodamine B (SRB) is commercially available from Sigma, and trichloroacetic acid (TCA), acetic acid and Tris base unbuffer are all analytical reagents made in China.

Example 1

Synthesis of the Intermediate 3-substituted phenyl-5-hydroxymethyl-isoxazole of Formula (III) and the Intermediate 3-substituted phenyl-5-aminomethyl-isoxazole Represented by Formula (IV)

wherein taking $R_3$=H as an example:
(1) Synthesis of Benzaldehyde Oxime

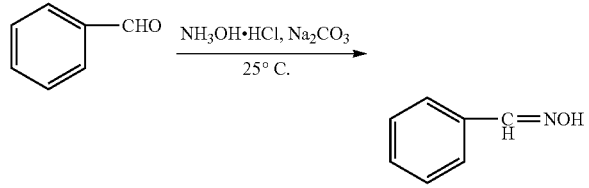

10.0 mmol of Benzaldehyde was dissolved in 30 ml of 30% solution of $CH_3OH$ and $H_2O$, and added into a triangular flask equipped with magnetic stirrer. 10.0 mmol of hydroxylamine hydrochloride was added under stirring. After hydroxylamine hydrochloride was dissolved, 5.0 mmol of dry and porphyrized sodium carbonate was slowly added. The reaction was carried out at room temperature. After the completion of the reaction monitored by TLC, methanol was removed from the system under reduced pressure. 30 ml $H_2O$ and dichloromethane (3×30 ml) were added to extract the mixture. The organic layers were combined, and then dried over anhydrous sodium sulfate. The solvent was removed to afford a crude product of benzaldehyde oxime in 86.2% yield. The crude material was directly used in the next reaction without separation and purification.

(2) Synthesis of 3-phenyl-5-hydroxymethyl-isoxazole

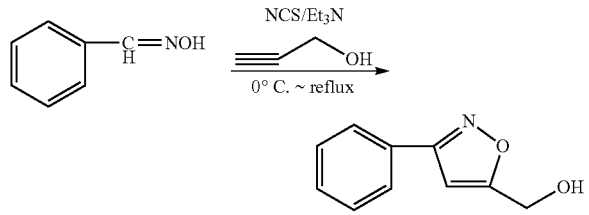

10.0 mmol of Benzaldehyde oxime and 30 ml of dry dichloromethane were added into a 250 ml single-necked round-bottom flask. After the addition of 1.60 g (12.0 mmol) of N-chlorosuccinimide (NCS) under stirring, the mixture was slightly heated until NCS was completely dissolved. 0.56 g (10.0 mmol) of 2-propyn-1-ol was added dropwise, and then 20 ml solution of triethylamine in dichloromethane containing 10.1 g (10.0 mmol) of triethylamine was slowly added dropwise. After the addition was complete, the system was refluxed. After the completion of the reaction monitored by TLC, the mother liquor was washed with water, dried over anhydrous sodium sulfate and was separated on column ($V_{petroleum\ ether}$:$V_{ethyl\ acetate}$=5:1-2:1) to give 3-phenyl-5-hydroxymethyl-isoxazole in 76.8% yield.

(3) Synthesis of 3-phenyl-5-aminomethyl-isoxazole

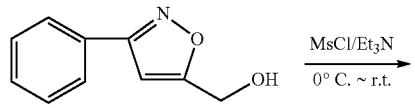

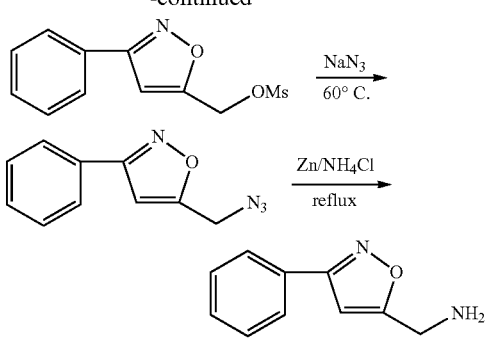

10.0 mmol of 5-hydroxymethyl-3-phenyl-isoxazole and 30 ml dry dichloromethane were added into a 250 ml single-necked round-bottom flask. In an ice bath, under stirring, 20 ml solution of triethylamine in dichloromethane containing 1.01 g (10.0 mmol) triethylamine was added into the system, and then a solution of 1.37 g (12.0 mmol) of methanesulfonyl chloride (MsCl) in dichloromethane was slowly added dropwise to the reaction system. After the reaction was held in an ice bath for 2 h, was and then carried out at room temperature. After the completion of the reaction monitored by TLC, the mother liquor was washed with water, 5% sodium bicarbonate solution, and water, dried over anhydrous sodium sulfate. The solvent was removed under reduced pressure to give a crude product of 3-phenyl-isoxazol-5-methyl methanesulfonate in 68.0% yield. The crude material was directly used in the next reaction without purification.

5.0 mmol of 3-phenyl-isoxazol-5-methyl methanesulfonate was dissolved in 20 ml of dry DMF. 0.34 g (5.20 mmol) of sodium azide was added and dissolved under stirring. The mixture was placed in an oil bath at 45-50 to react. After the completion of the reaction monitored by TLC, the mixture was filtered and the filter cake was washed with diethyl ether (2×30 ml). The organic layers were combined, to which 100 ml $H_2O$ was added. The resulting mixture as extracted with diethyl ether (5×30 ml). The organic layers were combined, washed with water for two times, and dried over anhydrous sodium sulfate. The solvent was removed to afford a crude product of 3-phenyl-5-azidemethyl-isoxazole in 90% yield. The crude product was directly used in the following reduction reaction.

5.0 mmol of 3-phenyl-5-azidemethyl-isoxazole was dissolved in a mixing solution of 80 ml of ethanol and 20 ml of water. 0.17 g (2.6 mmol) of zinc powder and 0.28 g (5.2 mmol) of $NH_4Cl$ were added into the system. After the reaction was refluxed for 1 hour, ethanol was removed under vacuum, and then 20 ml of water was added into the system, of which the pH value was then adjusted to 12 with 20% sodium hydroxide solution, and 50 ml of DCM was added. The mixture was stirred evenly and filtered. The filter residue was dissolved with small amount of water and filtered. Two filtrates were combined. The organic layer in the combined filtrates was collected, washed with water, and dried over anhydrous sodium sulfate. The solvent was removed under vacuum, and the residue was separated on column ($V_{dichloromethane}$:$V_{methanol}$=10:1) to afford the product of 3-phenyl-5-aminomethyl-isoxazole as a pale yellow solid in 75% yield, m.p. 39-40, $^1$H-NMR (400 MHz, CDCl$_3$, TMS), δppm: 1.60 (s, 2H, NH$_2$), 3.91 (s, 2H, CH$_2$), 6.40 (s, 1H), 7.39 (m, 2H, Ar—H), 7.76 (m, 2H, Ar—H).

Example 2

Synthesis of the Intermediate (II) (to be Illustrated by Taking the Synthesis of 6-tert-butyl-4-chloro-thieno[2,3-d]pyrimidine as an Example)

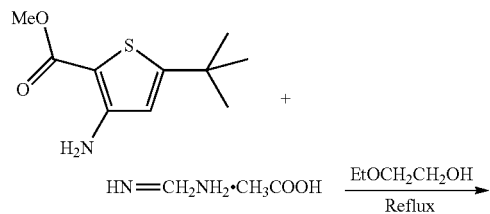

-continued

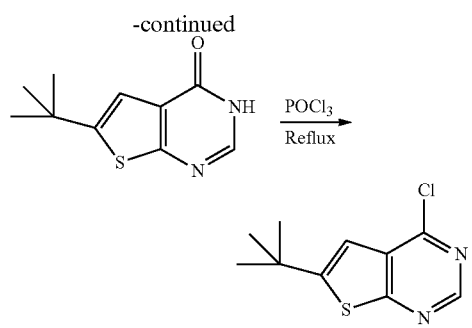

2.13 g (10 mmol) of methyl 3-amino-5-tert-butyl thiophen-2-carboxylate was added in a 250 ml single-necked round-bottom flask. Then 100 ml 2-ethoxyethanol and 2.14 g (20 mmol) formamidine acetate were added. The system is refluxed and stirring. After the completion of the reaction monitored by TLC, the reaction mixture was refluxed under stirring, the system was cooled down, distilled under reduced pressure until the residual ethylene glycol monomethyl ether was 30 ml, and said system was refrigerated for several hours so that a great number of solids was precipitated. The precipitation was filtered out and the filter cake was washed with cold ethyl ether several times, and dried under vacuum. The dried filter cake was directly used in the next reaction.

The above-described crude product was weighed and added in a 100 ml single-necked round-bottom flask. Three drops of phosphorous trichloride solution in DMF (20 in were slowly added dropwise. After the reaction mixture was refluxed for 6 hours, the excess amount of phosphorous trichloride was removed under reduced pressure. After cooling down, the resulting mixture was mixed with silica gel, and separated on column (V(petroleum ether):V(ethyl acetate)=4:1-1:1) to afford the target compound of 6-tert-butyl-4-chloro-thieno[2,3-d]pyrimidine as a pale yellow solid. $^1$H-NMR (400 MHz, CDCl$_3$, TMS), δ ppm: 1.43 (s, 9H, 3CH$_3$), 7.19 (s, 1H), 8.84 (s, 1H).

Example 3

Synthesis of 5-methyl-4-((3-phenyl-isoxazol-5-yl)-methoxy-)-thieno[2,3-d]pyrimidine

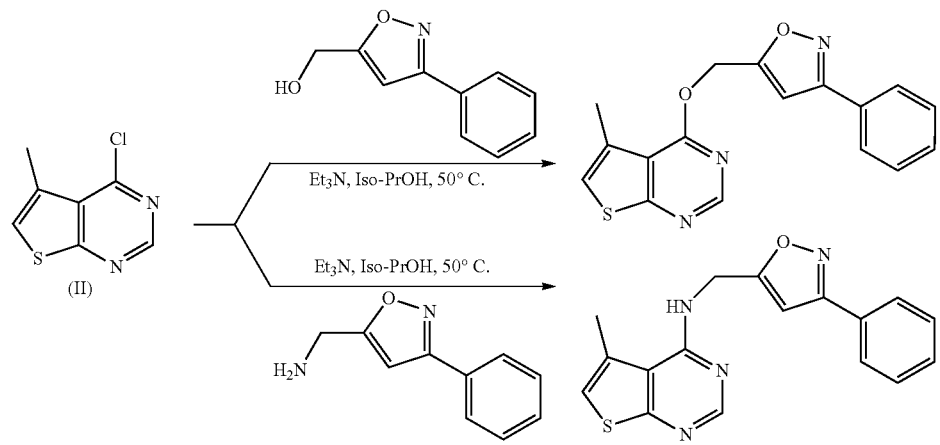

0.184 g (1 mmol) of 4-chloro-thieno[2,3-d]pyrimidine was dissolved in 5 ml of dry isopropanol. A solution of 0.175 g (1 mmol) of 5-hydroxymethyl-3-phenyl-isoxazole in 5 ml isopropanol was slowly added dropwise into the reaction system, followed by the addition of 0.101 g (1 mmol) freshly distilled triethylamine. The system was stirred at room temperature for 30 min and then was reacted at 60. After the completion of the reaction monitored by TLC, the reaction solution was concentrated under vacuum. The residue was directly separated on (V$_{(petroleum\ ether)}$:V$_{(ethyl\ acetate)}$=9:1-4:1) to give the target compound of 5-methyl-4-((3-phenyl-isoxazol-5-yl)-methoxy-)-thieno[2,3-d]pyrimidine (named S-1 in the following Table). The other compounds were synthesized according to the synthetic process of 5-methyl-4-((3-phenyl-isoxazol-5-yl)-methoxy-)-thieno[2,3-d]pyrimidine. Their structures were determined by analytical methods of IR, $^1$H NMR, ESI-MS, etc. The physical constants and spectral data of preferred compounds were illustrated in the form of table.

The structures, numbers and MS data of the compounds are shown as follows:

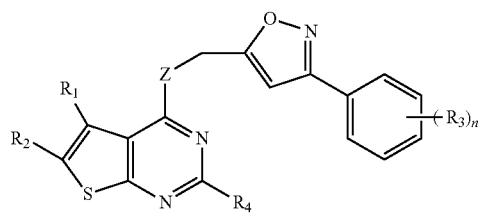

TABLE 1

Preferred compounds

| $R_1, R_2, R_4$ | Z | $(R_3)n$ | Number | MS (100%) | $(R_3)n_2$ | Number |
|---|---|---|---|---|---|---|
| $R_1$ = —$CH_3$ | O | H | S-1 | 323([M]$^+$, 25) | 4-F | S-4 |
| $R_2$ = H | | 4-$CH_3$ | S-2 | 337([M]$^+$, 10) | 2-Cl | S-6 |
| $R_4$ = H | | 4-$OCH_3$ | S-3 | 353([M]$^+$, 5) | 4-$CF_3$ | S-9 |
| | | 4-Cl | S-5 | 357([M]$^+$, 6) | 2,4-dimethoxy | S-10 |
| | | 2,4-dichloro | S-7 | 392([M]$^+$, 10) | | |
| | | 4-Br | S-8 | 402([M]$^+$, 15) | | |
| | NH | H | S-11 | | 2-Cl | S-16 |
| | | 4-$CH_3$ | S-12 | | 2,4-dichloro | S-17 |
| | | 4-$OCH_3$ | S-13 | | 4-Br | S-18 |
| | | 4-F | S-14 | | 4-$CF_3$ | S-19 |
| | | 4-Cl | S-15 | | 2,4-dimethoxy | S-20 |
| $R_1$ = —Ph | O | H | S-21 | 462([M + 1]$^+$, 100) | 4-$OCH_3$ | S-23 |
| $R_2$ = H | | 4-$CH_3$ | S-22 | | 4-F | S-24 |
| $R_4$ = —Ph | | 4-Cl | S-25 | 495([M]$^+$, 45), 496([M + 1]$^+$, 87) | 2,4-dichloro | S-27 |
| | | 2-Cl | S-26 | 495([M]$^+$, 52), 496([M + 1]$^+$, 78) | 4-$CF_3$ | S-29 |
| | | 4-Br | S-28 | 539([M − 1]$^−$, 37) | 2,4-dimethoxy | S-30 |
| | NH | H | S-31 | | 2-Cl | S-36 |
| | | 4-$CH_3$ | S-32 | | 2,4-dichloro | S-37 |
| | | 4-$OCH_3$ | S-33 | | 4-Br | S-38 |
| | | 4-F | S-34 | | 4-$CF_3$ | S-39 |
| | | 4-Cl | S-35 | | 2,4-dimethoxy | S-40 |
| $R_1$ = H | O | H | S-41 | 324([M + 1]$^+$, 20) | 4-F | S-44 |
| $R_2$ = —$CH_3$ | | 4-$CH_3$ | S-42 | 338([M + 1]$^+$, 100) | 4-$CF_3$ | S-49 |
| $R_4$ = H | | 4-$OCH_3$ | S-43 | 352([M]$^+$, 100) | 2,4-dimethoxy | S-50 |
| | | 4-Cl | S-45 | 379([M + 23]$^+$, 100) | | |
| | | 2-Cl | S-46 | 357([M]$^+$, 50) | | |
| | | 2,4-dichloro | S-47 | 393([M + 1]$^+$, 70) | | |
| | | 4-Br | S-48 | 441([M + 39]$^+$, 30) | | |
| | NH | H | S-51 | | 2-Cl | S-56 |
| | | 4-$CH_3$ | S-52 | | 2,4-dichloro | S-57 |
| | | 4-$OCH_3$ | S-53 | | 4-Br | S-58 |
| | | 4-F | S-54 | | 4-$CF_3$ | S-59 |
| | | 4-Cl | S-55 | | 2,4-dimethoxy | S-60 |
| $R_1$ = H | O | H | S-61 | | 2-Cl | S-66 |
| $R_2$ = —$C(CH_3)_3$ | | 4-$CH_3$ | S-62 | | 2,4-dichloro | S-67 |
| $R_4$ = H | | 4-$OCH_3$ | S-63 | | 4-Br | S-68 |
| | | 4-F | S-64 | | 4-$CF_3$ | S-69 |
| | | 4-Cl | S-65 | | 2,4-dimethoxy | S-70 |
| | NH | H | S-71 | | 2-Cl | S-76 |
| | | 4-$CH_3$ | S-72 | | 2,4-dichloro | S-77 |
| | | 4-$OCH_3$ | S-73 | | 4-Br | S-78 |
| | | 4-F | S-74 | | 4-$CF_3$ | S-79 |
| | | 4-Cl | S-75 | | 2,4-dimethoxy | S-80 |
| $R_1$ = H | O | H | S-81 | 337([M]$^+$, 10) | 4-F | S-84 |
| $R_2$ = —$CH_2CH_3$ | | 4-$CH_3$ | S-82 | 350([M − 1]$^−$, 18), 352([M + 1]$^+$, 10) | 4-$CF_3$ | S-89 |
| $R_4$ = H | | 4-$OCH_3$ | S-83 | 367([M]$^+$, 5), 368([M + 1]$^+$, 10) | 2,4-dimethoxy | S-90 |
| | | 4-Cl | S-85 | 389([M + 18]$^+$, 5) | | |
| | | 2-Cl | S-86 | 372([M + 1]$^+$, 15) | | |
| | | 2,4-dichloro | S-87 | 406([M]$^+$, 15) | | |
| | | 4-Br | S-88 | 416([M]$^+$, 5) | | |
| | NH | H | S-91 | | 2-Cl | S-96 |
| | | 4-$CH_3$ | S-92 | | 2,4-dichloro | S-97 |
| | | 4-$OCH_3$ | S-93 | | 4-Br | S-98 |
| | | 4-F | S-94 | | 4-$CF_3$ | S-99 |
| | | 4-Cl | S-95 | | 2,4-dimethoxy | S-100 |
| $R_1$ = —$CH_3$ | O | H | S-101 | 337([M]$^+$, 15) | 4-F | S-104 |
| $R_2$ = —$CH_3$ | | 4-$CH_3$ | S-102 | 352([M + 1]$^+$, 8) | 4-$CF_3$ | S-109 |
| $R_4$ = H | | 4-$OCH_3$ | S-103 | 367([M]$^+$, 10) | 2,4-dimethoxy | S-110 |
| | | 4-Cl | S-105 | 371([M]$^+$, 20) | | |
| | | 2-Cl | S-106 | 371([M]$^+$, 5) | | |
| | | 2,4-dichloro | S-107 | 406([M]$^+$, 10) | | |
| | | 4-Br | S-108 | 416([M]$^+$, 15) | | |
| | NH | H | S-111 | | 2-Cl | S-116 |
| | | 4-$CH_3$ | S-112 | | 2,4-dichloro | S-117 |
| | | 4-$OCH_3$ | S-113 | | 4-Br | S-118 |
| | | 4-F | S-114 | | 4-$CF_3$ | S-119 |
| | | 4-Cl | S-115 | | 2,4-dimethoxy | S-120 |

TABLE 1-continued

Preferred compounds

| $R_1, R_2, R_4$ | Z | $(R_3)n$ | Number | MS (100%) | $(R_3)n_2$ | Number |
|---|---|---|---|---|---|---|
| $R_1, R_2 =$ —$CH_2$—CH— | O | H | S-121 | 363([M]$^+$, 25) | 4-F | S-124 |
| $R_4 =$ H | | 4-$CH_3$ | S-122 | 378([M + 1]$^+$, 15) | 4-Cl | S-125 |
| $n_1 = 2$ | | 4-$OCH_3$ | S-123 | 394([M + 1]$^+$, 50) | 4-$CF_3$ | S-129 |
| | | 2-Cl | S-126 | 397([M]$^+$, 10) | 2,4-dimethoxy | S-130 |
| | | 2,4-dichloro | S-127 | 431([M − 1]$^-$, 67) | | |
| | | 4-Br | S-128 | 441([M − 1]$^-$, 100) | | |
| | NH | H | S-131 | | 2-Cl | S-136 |
| | | 4-$CH_3$ | S-132 | | 2,4-dichloro | S-137 |
| | | 4-$OCH_3$ | S-133 | | 4-Br | S-138 |
| | | 4-F | S-134 | | 4-$CF_3$ | S-139 |
| | | 4-Cl | S-135 | | 2,4-dimethoxy | S-140 |

TABLE 2

Physical states and IR data of the compounds in Table 1

| Number | Physical state | IR/cm$^{-1}$ |
|---|---|---|
| S-1 | white solid | 3103, 1567, 1546, 1442, 1309, 1026, 770 |
| S-2 | white solid | 3107, 1567, 1548, 1457, 1444, 1312, 1028, 817 |
| S-3 | white solid | 3107, 1567, 1548, 1457, 1444, 1312, 1028, 821 |
| S-4 | white solid | 3107, 1567, 1548, 1457, 1444, 1312, 1028, 836 |
| S-5 | white solid | 3107, 1567, 1548, 1457, 1444, 1312, 1028, 829 |
| S-6 | white solid | 3107, 1567, 1548, 1457, 1444, 1312, 1028, 817 |
| S-7 | white solid | 3107, 1567, 1548, 1457, 1444, 1312, 1028, 845 |
| S-8 | white solid | 3107, 1567, 1548, 1457, 1444, 1312, 1028, 847 |
| S-9 | white solid | 3107, 1567, 1548, 1457, 1444, 1312, 1028, 817 |
| S-10 | white solid | 3107, 1567, 1548, 1457, 1444, 1312, 1028, 816 |
| S-11 | white solid | 3237, 3103, 1567, 1546, 1442, 1309, 1026, 770 |
| S-12 | white solid | 3230, 3107, 1567, 1548, 1457, 1444, 1312, 1028, 817 |
| S-13 | white solid | 3368, 3107, 1567, 1548, 1457, 1444, 1312, 1028, 821 |
| S-14 | white solid | 3228, 3107, 1567, 1548, 1457, 1444, 1312, 1028, 836 |
| S-15 | white solid | 3231, 3107, 1567, 1548, 1457, 1444, 1312, 1028, 829 |
| S-16 | white solid | 3238, 3107, 1567, 1548, 1457, 1444, 1312, 1028, 817 |
| S-17 | white solid | 3210, 3107, 1567, 1548, 1457, 1444, 1312, 1028, 845 |
| S-18 | white solid | 3218, 3107, 1567, 1548, 1457, 1444, 1312, 1028, 847 |
| S-19 | white solid | 3228, 3107, 1567, 1548, 1457, 1444, 1312, 1028, 817 |
| S-20 | white solid | 3218, 3107, 1567, 1548, 1457, 1444, 1312, 1028, 816 |
| S-21 | white solid | 3107, 1567, 1548, 1457, 1444, 1312, 1028, 756 |
| S-22 | white solid | 3105, 1567, 1545, 1457, 1441, 1312, 1028, 817 |
| S-23 | white solid | 3107, 1567, 1545, 1457, 1440, 1312, 1028, 820 |
| S-24 | white solid | 3107, 1565, 1548, 1457, 1444, 1312, 1028, 815 |
| S-25 | white solid | 3107, 1567, 1548, 1457, 1444, 1312, 1028, 830 |
| S-26 | white solid | 3107, 1566, 1548, 1456, 1443, 1312, 1028, 835 |
| S-27 | white solid | 3107, 1567, 1548, 1457, 1444, 1312, 1028, 817 |
| S-28 | white solid | 3107, 1567, 1548, 1457, 1444, 1312, 1028, 817 |
| S-29 | white solid | 3107, 1567, 1548, 1457, 1444, 1312, 1028, 817 |
| S-30 | white solid | 3107, 1567, 1548, 1457, 1444, 1312, 1028, 817 |
| S-31 | white solid | 3237, 3103, 1567, 1546, 1442, 1309, 1026, 770 |
| S-32 | white solid | 3237, 3103, 1567, 1546, 1442, 1309, 1026, 770 |
| S-33 | white solid | 3237, 3103, 1567, 1546, 1442, 1309, 1026, 770 |
| S-34 | white solid | 3237, 3103, 1567, 1546, 1442, 1309, 1026, 770 |
| S-35 | white solid | 3237, 3103, 1567, 1546, 1442, 1309, 1026, 770 |
| S-36 | white solid | 3237, 3103, 1567, 1546, 1442, 1309, 1026, 770 |
| S-37 | white solid | 3237, 3103, 1567, 1546, 1442, 1309, 1026, 770 |
| S-38 | white solid | 3237, 3103, 1567, 1546, 1442, 1309, 1026, 770 |
| S-39 | white solid | 3237, 3103, 1567, 1546, 1442, 1309, 1026, 770 |
| S-40 | white solid | 3237, 3103, 1567, 1546, 1442, 1309, 1026, 770 |
| S-41 | white solid | 3103, 1567, 1546, 1442, 1309, 1026, 770 |
| S-42 | white solid | 3103, 1567, 1546, 1442, 1309, 1026, 812 |
| S-43 | white solid | 3103, 1567, 1546, 1442, 1309, 1026, 835 |
| S-44 | white solid | 3103, 1567, 1546, 1442, 1309, 1026, 850 |
| S-45 | white solid | 3103, 1567, 1546, 1442, 1309, 1026, 832 |
| S-46 | white solid | 3103, 1567, 1546, 1442, 1309, 1026, 867 |
| S-47 | white solid | 3103, 1567, 1546, 1442, 1309, 1026, 856 |
| S-48 | white solid | 3103, 1567, 1546, 1442, 1309, 1026, 834 |
| S-49 | white solid | 3103, 1567, 1546, 1442, 1309, 1026, 865 |
| S-50 | white solid | 3103, 1567, 1546, 1442, 1309, 1026, 823 |
| S-51 | white solid | 3237, 3103, 1567, 1546, 1442, 1309, 1026, 770 |
| S-52 | white solid | 3237, 3103, 1567, 1546, 1442, 1309, 1026, 815 |
| S-53 | white solid | 3237, 3103, 1567, 1546, 1442, 1309, 1026, 834 |
| S-54 | white solid | 3237, 3103, 1567, 1546, 1442, 1309, 1026, 850 |
| S-55 | white solid | 3237, 3103, 1567, 1546, 1442, 1309, 1026, 867 |

TABLE 2-continued

Physical states and IR data of the compounds in Table 1

| Number | Physical state | IR/cm$^{-1}$ |
|---|---|---|
| S-56 | white solid | 3237, 3103, 1567, 1546, 1442, 1309, 1026, 834 |
| S-57 | white solid | 3237, 3103, 1567, 1546, 1442, 1309, 1026, 821 |
| S-58 | white solid | 3237, 3103, 1567, 1546, 1442, 1309, 1026, 845 |
| S-59 | white solid | 3237, 3103, 1567, 1546, 1442, 1309, 1026, 860 |
| S-60 | white solid | 3237, 3103, 1567, 1546, 1442, 1309, 1026, 835 |
| S-61 | white solid | 3109, 1571, 1549, 1510, 1461, 1431, 1363, 1322, 1036, 775 |
| S-62 | white solid | 3109, 1571, 1549, 1510, 1461, 1431, 1363, 1322, 1036, 810 |
| S-63 | white solid | 3109, 1571, 1549, 1510, 1461, 1431, 1363, 1322, 1036, 823 |
| S-64 | white solid | 3109, 1571, 1549, 1510, 1461, 1431, 1363, 1322, 1036, 835 |
| S-65 | white solid | 3109, 1571, 1549, 1510, 1461, 1431, 1363, 1322, 1036, 840 |
| S-66 | white solid | 3109, 1571, 1549, 1510, 1461, 1431, 1363, 1322, 1036, 860 |
| S-67 | white solid | 3109, 1571, 1549, 1510, 1461, 1431, 1363, 1322, 1036, 851 |
| S-68 | white solid | 3109, 1571, 1549, 1510, 1461, 1431, 1363, 1322, 1036, 875 |
| S-69 | white solid | 3109, 1571, 1549, 1510, 1461, 1431, 1363, 1322, 1036, 835 |
| S-70 | white solid | 3109, 1571, 1549, 1510, 1461, 1431, 1363, 1322, 1036, 832 |
| S-71 | white solid | 3237, 3103, 1567, 1546, 1442, 1309, 1026, 775 |
| S-72 | white solid | 3237, 3103, 1567, 1546, 1442, 1309, 1026, 821 |
| S-73 | white solid | 3237, 3103, 1567, 1546, 1442, 1309, 1026, 835 |
| S-74 | white solid | 3237, 3103, 1567, 1546, 1442, 1309, 1026, 845 |
| S-75 | white solid | 3237, 3103, 1567, 1546, 1442, 1309, 1026, 835 |
| S-76 | white solid | 3237, 3103, 1567, 1546, 1442, 1309, 1026, 851 |
| S-77 | white solid | 3237, 3103, 1567, 1546, 1442, 1309, 1026, 823 |
| S-78 | white solid | 3237, 3103, 1567, 1546, 1442, 1309, 1026, 853 |
| S-79 | white solid | 3237, 3103, 1567, 1546, 1442, 1309, 1026, 835 |
| S-80 | white solid | 3237, 3103, 1567, 1546, 1442, 1309, 1026, 843 |
| S-81 | white solid | 3109, 1571, 1549, 1510, 1461, 1431, 1363, 1322, 1036, 775 |
| S-82 | white solid | 3109, 1571, 1549, 1510, 1461, 1431, 1363, 1322, 1036, 845 |
| S-83 | white solid | 3109, 1571, 1549, 1510, 1461, 1431, 1363, 1322, 1036, 845 |
| S-84 | white solid | 3109, 1571, 1549, 1510, 1461, 1431, 1363, 1322, 1036, 845 |
| S-85 | white solid | 3109, 1571, 1549, 1510, 1461, 1431, 1363, 1322, 1036, 845 |
| S-86 | white solid | 3109, 1571, 1549, 1510, 1461, 1431, 1363, 1322, 1036, 845 |
| S-87 | white solid | 3109, 1571, 1549, 1510, 1461, 1431, 1363, 1322, 1036, 845 |
| S-88 | white solid | 3111, 1571, 1548, 1512, 1461, 1429, 1372, 1322, 1036, 846 |
| S-89 | white solid | 3109, 1571, 1549, 1510, 1461, 1431, 1363, 1322, 1036, 845 |
| S-90 | white solid | 3109, 1571, 1549, 1510, 1461, 1431, 1363, 1322, 1036, 827 |
| S-91 | white solid | 3237, 3109, 1571, 1549, 1461, 1431, 1363, 1322, 1036, 775 |
| S-92 | white solid | 3230, 3109, 1571, 1549, 1461, 1431, 1363, 1322, 1036, 845 |
| S-93 | white solid | 3368, 3109, 1571, 1549, 1461, 1431, 1363, 1322, 1036, 845 |
| S-94 | white solid | 3228, 3109, 1571, 1549, 1461, 1431, 1363, 1322, 1036, 845 |
| S-95 | white solid | 3231, 3109, 1571, 1549, 1461, 1431, 1363, 1322, 1036, 845 |
| S-96 | white solid | 3238, 3109, 1571, 1549, 1461, 1431, 1363, 1322, 1036, 845 |
| S-97 | white solid | 3210, 3109, 1571, 1549, 1461, 1431, 1363, 1322, 1036, 845 |
| S-98 | white solid | 3218, 3111, 1571, 1548, 1461, 1429, 1372, 1322, 1036,, 846 |
| S-99 | white solid | 3228, 3109, 1571, 1549, 1461, 1431, 1363, 1322, 1036, 845 |
| S-100 | white solid | 3218, 3109, 1571, 1549, 1461, 1431, 1363, 1322, 1036, 827 |
| S-101 | white solid | 3103, 1567, 1546, 1442, 1309, 1026, 770 |
| S-102 | white solid | 3107, 1567, 1548, 1457, 1444, 1312, 1028, 817 |
| S-103 | white solid | 3107, 1567, 1548, 1457, 1444, 1312, 1028, 821 |
| S-104 | white solid | 3107, 1567, 1548, 1457, 1444, 1312, 1028, 836 |
| S-105 | white solid | 3107, 1567, 1548, 1457, 1444, 1312, 1028, 829 |
| S-106 | white solid | 3107, 1567, 1548, 1457, 1444, 1312, 1028, 817 |
| S-107 | white solid | 3107, 1567, 1548, 1457, 1444, 1312, 1028, 845 |
| S-108 | white solid | 3107, 1567, 1548, 1457, 1444, 1312, 1028, 847 |
| S-109 | white solid | 3107, 1567, 1548, 1457, 1444, 1312, 1028, 817 |
| S-110 | white solid | 3107, 1567, 1548, 1457, 1444, 1312, 1028, 816 |
| S-111 | white solid | 3237, 3103, 1567, 1546, 1442, 1309, 1026, 770 |
| S-112 | white solid | 3230, 3107, 1567, 1548, 1457, 1444, 1312, 1028, 817 |
| S-113 | white solid | 3368, 3107, 1567, 1548, 1457, 1444, 1312, 1028, 821 |
| S-114 | white solid | 3228, 3107, 1567, 1548, 1457, 1444, 1312, 1028, 836 |
| S-115 | white solid | 3231, 3107, 1567, 1548, 1457, 1444, 1312, 1028, 829 |
| S-116 | white solid | 3238, 3107, 1567, 1548, 1457, 1444, 1312, 1028, 817 |
| S-117 | white solid | 3210, 3107, 1567, 1548, 1457, 1444, 1312, 1028, 845 |
| S-118 | white solid | 3218, 3107, 1567, 1548, 1457, 1444, 1312, 1028, 847 |
| S-119 | white solid | 3228, 3107, 1567, 1548, 1457, 1444, 1312, 1028, 817 |
| S-120 | white solid | 3218, 3107, 1567, 1548, 1457, 1444, 1312, 1028, 816 |
| S-121 | white solid | 3109, 1561, 1531, 1510, 1455, 1434, 1386, 1311, 1028, 826 |
| S-122 | white solid | 3124, 2957, 1613, 1571, 1562, 1460, 1396, 1311, 1075, 1058, 888 |
| S-123 | white solid | 3124, 2957, 1613, 1571, 1562, 1460, 1396, 1311, 1075, 1058, 888 |
| S-124 | white solid | 3124, 2957, 1613, 1571, 1562, 1460, 1432, 1311, 1075, 1058, 888 |
| S-125 | white solid | 3124, 2957, 1613, 1571, 1562, 1460, 1432, 1311, 1075, 1058, 888 |
| S-126 | white solid | 3124, 2957, 1613, 1571, 1562, 1460, 1396, 1311, 1075, 1058, 888 |
| S-127 | white solid | 3124, 2957, 1613, 1571, 1562, 1460, 1396, 1311, 1075, 1058, 888 |
| S-128 | white solid | 3124, 2957, 1613, 1571, 1562, 1460, 1432, 1311, 1075, 1058, 888 |
| S-129 | white solid | 3124, 2957, 1613, 1571, 1562, 1460, 1432, 1311, 1075, 1058, 888 |
| S-130 | white solid | 3124, 2957, 1613, 1571, 1562, 1460, 1432, 1311, 1075, 1058, 888 |
| S-131 | white solid | 3237, 3109, 1561, 1531, 1510, 1455, 1434, 1386, 1028, 826 |

TABLE 2-continued

Physical states and IR data of the compounds in Table 1

| Number | Physical state | IR/cm$^{-1}$ |
| --- | --- | --- |
| S-132 | white solid | 3230, 3124, 2957, 1613, 1571, 1562, 1460, 1396, 1311, 1075, 888 |
| S-133 | white solid | 3368, 3124, 2957, 1613, 1571, 1562, 1460, 1432, 1396, 888 |
| S-134 | white solid | 3228, 3124, 2957, 1613, 1571, 1562, 1460, 1432, 1396, 888 |
| S-135 | white solid | 3231, 3124, 2957, 1613, 1571, 1562, 1460, 1432, 1396, 1075 |
| S-136 | white solid | 3238, 3124, 2957, 1613, 1571, 1562, 1460, 1432, 1396, 1075 |
| S-137 | white solid | 3210, 3124, 2957, 1613, 1571, 1562, 1460, 1432, 1396, 1311 |
| S-138 | white solid | 3218, 3124, 2957, 1613, 1571, 1562, 1460, 1432, 1396, 1075 |
| S-139 | white solid | 3228, 3124, 2957, 1613, 1571, 1562, 1460, 1432, 1396, 1311, 1057 |
| S-140 | white solid | 3218, 3124, 2957, 1613, 1571, 1562, 1460, 1432, 1396, 1311 |

TABLE 3

$^1$H NMR data of the compounds in Table 1

| Number | $^1$HNMR (400 MHz, DMSO-d$_6$) |
| --- | --- |
| S-1 | 2.54(s, 3H, CH$_3$), 5.82(s, 2H, CH$_2$), 7.22(s, 1H, isoxazole-H), 7.47(s, 1H), 7.48-7.53(m, 3H), 7.88-7.90(m, 2H), 8.70(s, 1H). |
| S-2 | 2.36(s, 3H, Ph—CH$_3$), 2.53(s, 3H, CH$_3$), 5.80(s, 2H, CH$_2$), 7.18(s, 1H, isoxazole-H), 7.33(d, 2H, J = 8.0 Hz), 7.47(s, 1H), 7.79(d, 2H, J = 8.0 Hz), 8.69(s, 1H). |
| S-3 | 2.51(s, 3H, CH$_3$), 3.82(s, 3H, Ph—OCH$_3$), 5.79(s, 2H, CH$_2$), 7.07(d, 2H, J = 8.8 Hz), 7.15(s, 1H, isoxazole-H), 7.47(s, 1H), 7.84(d, 2H, J = 8.8 Hz), 8.69(s, 1H). |
| S-4 | 2.51(s, 3H, CH$_3$), 5.82(s, 2H, CH$_2$), 7.25(s, 1H, isoxazole-H), 7.47(s, 1H), 7.59 (d, 2H, J = 8.4 Hz), 7.93(d, 2H, J = 8.4 Hz), 8.69(s, 1H). |
| S-5 | 2.51(s, 3H, CH$_3$), 5.82(s, 2H, CH$_2$), 7.25(s, 1H, isoxazole-H), 7.47(s, 1H), 7.59 (d, 2H, J = 8.4 Hz), 7.93(d, 2H, J = 8.4 Hz), 8.69(s, 1H). |
| S-6 | 2.53(s, 3H, CH$_3$), 5.84(s, 2H, CH$_2$), 7.11(s, 1H, isoxazole-H), 7.47-7.54(m, 3H), 7.64-7.66(m, 1H), 7.71-7.73(m, 1H), 8.70(s, 1H). |
| S-7 | 2.53(s, 3H, CH$_3$), 5.85(s, 2H, CH$_2$), 7.13(s, 1H, isoxazole-H), 7.47(d, 1H, J = 1.2 Hz), 7.58-7.60(m, 1H), 7.76(s, 1H), 7.85(d, 1H, J = 2.0 Hz), 8.70(s, 1H). |
| S-8 | 2.54(s, 3H, CH$_3$), 5.82(s, 2H, CH$_2$), 7.25(s, 1H, isoxazole-H), 7.47(s, 1H), 7.74(d, 2H, J = 6.8 Hz), 7.87(d, 2H, J = 8.8 Hz), 8.69(s, 1H). |
| S-9 | 2.52(s, 3H, CH$_3$), 5.85(s, 2H, CH$_2$), 7.18(s, 1H, isoxazole-H), 7.49(s, 1H), 7.78(d, 2H, J = 6.8 Hz), 7.92(d, 2H, J = 8.8 Hz), 8.72(s, 1H). |
| S-10 | 2.54(s, 3H, CH$_3$), 3.83(s, 6H, 2OCH$_3$), 5.82(s, 2H, CH$_2$), 7.22(s, 1H, isoxazole-H), 7.23-7.24(m, 2H), 7.62(d, 1H, J = 2.0 Hz), 8.70(s, 1H). |
| S-11 | 2.54(s, 3H, CH$_3$), 4.22(t, 1H, J = 6.6 Hz, NH), 5.82(s, 2H, CH$_2$), 7.22(s, 1H, isoxazole-H), 7.47(s, 1H), 7.48-7.53(m, 3H), 7.88-7.90(m, 2H), 8.70(s, 1H). |
| S-12 | 2.36(s, 3H, Ph—CH$_3$), 2.53(s, 3H, CH$_3$), 4.29(t, 1H, J = 6.4 Hz, NH), 5.80(s, 2H, CH$_2$), 7.18(s, 1H, isoxazole-H), 7.33(d, 2H, J = 8.0 Hz), 7.47(s, 1H), 7.79(d, 2H, J = 8.0 Hz), 8.69(s, 1H). |
| S-13 | 2.51(s, 3H, CH$_3$), 3.82(s, 3H, Ph—OCH$_3$), 4.28(t, 1H, J = 6.5 Hz, NH), 5.79(s, 2H, CH$_2$), 7.07(d, 2H, J = 8.8 Hz), 7.15(s, 1H, isoxazole-H), 7.47(s, 1H), 7.84(d, 2H, J = 8.8 Hz), 8.69(s, 1H). |
| S-14 | 2.51(s, 3H, CH$_3$), 4.28(t, 1H, J = 6.5 Hz, NH), 5.82(s, 2H, CH$_2$), 7.25(s, 1H, isoxazole-H), 7.47(s, 1H), 7.59 (d, 2H, J = 8.4 Hz), 7.93(d, 2H, J = 8.4 Hz), 8.69(s, 1H). |
| S-15 | 2.51(s, 3H, CH$_3$), 4.31(t, 1H, J = 6.5 Hz, NH), 5.82(s, 2H, CH$_2$), 7.25(s, 1H, isoxazole-H), 7.47(s, 1H), 7.59 (d, 2H, J = 8.4 Hz), 7.93(d, 2H, J = 8.4 Hz), 8.69(s, 1H). |
| S-16 | 2.53(s, 3H, CH$_3$), 4.33(t, 1H, J = 6.5 Hz, NH), 5.84(s, 2H, CH$_2$), 7.11(s, 1H, isoxazole-H), 7.47-7.54(m, 3H), 7.64-7.66(m, 1H), 7.71-7.73(m, 1H), 8.70(s, 1H). |
| S-17 | 2.53(s, 3H, CH$_3$), 4.38(t, 1H, J = 6.5 Hz, NH), 5.85(s, 2H, CH$_2$), 7.13(s, 1H, isoxazole-H), 7.47(d, 1H, J = 1.2 Hz), 7.58-7.60(m, 1H), 7.76(s, 1H), 7.85(d, 1H, J = 2.0 Hz), 8.70(s, 1H). |
| S-18 | 2.54(s, 3H, CH$_3$), 4.32(t, 1H, J = 6.5 Hz, NH), 5.82(s, 2H, CH$_2$), 7.25(s, 1H, isoxazole-H), 7.47(s, 1H), 7.74(d, 2H, J = 6.8 Hz), 7.87(d, 2H, J = 8.8 Hz), 8.69(s, 1H). |
| S-19 | 2.52(s, 3H, CH$_3$), 4.37(t, 1H, J = 6.5 Hz, NH), 5.85(s, 2H, CH$_2$), 7.18(s, 1H, isoxazole-H), 7.49(s, 1H), 7.78(d, 2H, J = 6.8 Hz), 7.92(d, 2H, J = 8.8 Hz), 8.72(s, 1H). |
| S-20 | 2.54(s, 3H, CH$_3$), 3.83(s, 6H, 2OCH$_3$), 4.26(t, 1H, J = 6.5 Hz, NH), 5.82(s, 2H, CH$_2$), 7.22(s, 1H, isoxazole-H), 7.23-7.24(m, 2H), 7.62(d, 1H, J = 2.0 Hz), 8.70(s, 1H). |
| S-21 | 5.83(s, 2H, CH$_2$), 6.81(s, 1H, isoxazole-H), 7.38-7.42(m, 3H), 7.51-7.62(m, 8H), 7.80(s, 1H), 7.81-7.84(m, 2H), 8.51-8.53(m, 2H) |
| S-22 | 2.37(s, 3H, Ph—CH$_3$), 5.82(s, 2H, CH$_2$), 6.76(s, 1H, isoxazole-H), 7.34-7.40(m, 5H), 7.56-7.62(m, 5H), 7.68-7.72(m, 2H), 7.80(s, 1H), 8.51-8.53(m, 2H). |
| S-23 | 3.84(s, 3H, Ph—OCH$_3$), 5.81(s, 2H, CH$_2$), 6.72(s, 1H, isoxazole-H), 7.08-7.10(m, 2H), 7.39-7.42(m, H), 7.56-7.62(m, 5H), 7.75(d, 1H, J = 2.0 Hz), 7.77(d, 1H, J = 2.0 Hz), 7.80(d, 1H, J = 1.6 Hz), 8.51-8.53(m, 2H). |
| S-24 | 5.83(s, 2H, CH$_2$), 6.83(s, 1H, isoxazole-H), 7.38-7.41(m, 3H), ), 7.55-7.63(m, 7H), 7.80(s, 1H), 7.83-7.84(m, 1H), 7.86-7.87(m, 1H), 8.50-8.53(m, 2H). |
| S-25 | 5.83(s, 2H, CH$_2$), 6.84(s, 1H, isoxazole-H), 7.39-7.42(m, 3H), ), 7.55-7.63(m, 7H), 7.80(s, 1H), 7.83-7.84(m, 1H), 7.86-7.87(m, 1H), 8.50-8.53(m, 2H). |
| S-26 | 5.86(s, 2H, CH$_2$), 6.81(s, 1H, isoxazole-H), 7.31-7.40(m, 3H), 7.48-7.60(m, 6H), 7.64(d, 1H, J = 0.8 Hz), 7.66(d, 1H, J = 1.6 Hz), 7.68(d, 1H, J = 1.6 Hz), 7.79(s, 1H), 8.52-8.54(m, 2H). |

TABLE 3-continued

<sup>1</sup>H NMR data of the compounds in Table 1

| Number | <sup>1</sup>HNMR (400 MHz, DMSO-d$_6$) |
|---|---|
| S-27 | 5.86(s, 2H, CH$_2$), 6.82(s, 1H, isoxazole-H), 7.34-7.40(m, 3H), 7.56-7.60(m, 5H), 7.62(d, 1H, J = 2.0 Hz), 7.70(d, 1H, J = 8.4 Hz), 7.79(s, 1H), 7.84(d, 1H, J = 2.0 Hz), 8.51-8.54(m, 2H). |
| S-28 | 5.83(s, 2H, CH$_2$), 6.84(s, 1H, isoxazole-H), 7.39-7.41(m, 3H), 7.56-7.61(m, 5H), 7.74-7.78(m, 3H), 7.80(s, 2H), 8.50-8.53(m, 2H). |
| S-29 | 5.82(s, 2H, CH$_2$), 6.83(s, 1H, isoxazole-H), 7.39-7.41(m, 3H), 7.56-7.61(m, 5H), 7.74-7.78(m, 3H), 7.80(s, 2H), 8.50-8.53(m, 2H). |
| S-30 | 3.83(s, 6H, 2OCH$_3$), 5.86(s, 2H, CH$_2$), 6.82(s, 1H, isoxazole-H), 7.34-7.40(m, 3H), 7.56-7.60(m, 5H), 7.62(d, 1H, J = 2.0 Hz), 7.70(d, 1H, J = 8.4 Hz), 7.79(s, 1H), 7.84(d, 1H, J = 2.0 Hz), 8.51-8.54(m, 2H). |
| S-31 | 4.22(t, 1H, J = 6.6 Hz, NH), 5.83(s, 2H, CH$_2$), 6.81(s, 1H, isoxazole-H), 7.38-7.42(m, 3H), 7.51-7.62(m, 8H), 7.80(s, 1H), 7.81-7.84(m, 2H), 8.51-8.53(m, 2H). |
| S-32 | 2.37(s, 3H, Ph—CH$_3$), 4.29(t, 1H, J = 6.4 Hz, NH), 5.82(s, 2H, CH$_2$), 6.76(s, 1H, isoxazole-H), 7.34-7.40(m, 5H), 7.56-7.62(m, 5H), 7.68-7.72(m, 2H), 7.80(s, 1H), 8.51-8.53(m, 2H). |
| S-33 | 3.84(s, 3H, Ph—OCH$_3$), 4.28(t, 1H, J = 6.5 Hz, NH), 5.81(s, 2H, CH$_2$), 6.72(s, 1H, isoxazole-H), 7.08-7.10(m, 2H), 7.39-7.42(m, H), 7.56-7.62(m, 5H), 7.75(d, 1H, J = 2.0 Hz), 7.77(d, 1H, J = 2.0 Hz), 7.80(d, 1H, J = 1.6 Hz), 8.51-8.53(m, 2H). |
| S-34 | 4.28(t, 1H, J = 6.5 Hz, NH), 5.83(s, 2H, CH$_2$), 6.83(s, 1H, isoxazole-H), 7.38-7.41(m, 3H), ), 7.55-7.63(m, 7H), 7.80(s, 1H), 7.83-7.84(m, 1H), 7.86-7.87(m, 1H), 8.50-8.53(m, 2H). |
| S-35 | 4.31(t, 1H, J = 6.5 Hz, NH), 5.83(s, 2H, CH$_2$), 6.84(s, 1H, isoxazole-H), 7.39-7.42(m, 3H), ), 7.55-7.63(m, 7H), 7.80(s, 1H), 7.83-7.84(m, 1H), 7.86-7.87(m, 1H), 8.50-8.53(m, 2H). |
| S-36 | 4.33(t, 1H, J = 6.5 Hz, NH), 5.86(s, 2H, CH$_2$), 6.81(s, 1H, isoxazole-H), 7.31-7.40(m, 3H), 7.48-7.60(m, 6H), 7.64(d, 1H, J = 0.8 Hz), 7.66(d, 1H, J = 1.6 Hz), 7.68(d, 1H, J = 1.6 Hz), 7.79(s, 1H), 8.52-8.54(m, 2H). |
| S-37 | 4.38(t, 1H, J = 6.5 Hz, NH), 5.86(s, 2H, CH$_2$), 6.82(s, 1H, isoxazole-H), 7.34-7.40(m, 3H), 7.56-7.60(m, 5H), 7.62(d, 1H, J = 2.0 Hz), 7.70(d, 1H, J = 8.4 Hz), 7.79(s, 1H), 7.84(d, 1H, J = 2.0 Hz), 8.51-8.54(m, 2H). |
| S-38 | 4.32(t, 1H, J = 6.5 Hz, NH), 5.83(s, 2H, CH$_2$), 6.84(s, 1H, isoxazole-H), 7.39-7.41(m, 3H), 7.56-7.61(m, 5H), 7.74-7.78(m, 3H), 7.80(s, 2H), 8.50-8.53(m, 2H). |
| S-39 | 4.37(t, 1H, J = 6.5 Hz, NH), 5.82(s, 2H, CH$_2$), 6.83(s, 1H, isoxazole-H), 7.39-7.41(m, 3H), 7.56-7.61(m, 5H), 7.74-7.78(m, 3H), 7.80(s, 2H), 8.50-8.53(m, 2H). |
| S-40 | 3.83(s, 6H, 2OCH$_3$), 4.26(t, 1H, J = 6.5 Hz, NH), 5.86(s, 2H, CH$_2$), 6.82(s, 1H, isoxazole-H), 7.34-7.40(m, 3H), 7.56-7.60(m, 5H), 7.62(d, 1H, J = 2.0 Hz), 7.70(d, 1H, J = 8.4 Hz), 7.79(s, 1H), 7.84(d, 1H, J = 2.0 Hz), 8.51-8.54(m, 2H). |
| S-41 | 2.61(s, 3H, CH$_3$), 5.80(s, 2H, CH$_2$), 7.24(s, 1H, isoxazole-H), 7.26-7.27(m, 1H), 7.51(d, 2H, J = 2.8 Hz), 7.52-7.53(m, 1H), 7.88-7.90(m, 2H), 8.68(s, 1H). |
| S-42 | 2.36(s, 3H, Ph—CH$_3$), 2.61(s, 3H, CH$_3$), 5.79(s, 2H, CH$_2$), 7.20(s, 1H, isoxazole-H), 7.26(d, 1H, J = 1.2 Hz), 7.33(d, 2H, J = 8.0 Hz), 7.78(d, 2H, J = 8.0 Hz), 8.67(s, 1H). |
| S-43 | 2.61(s, 3H, CH$_3$), 3.80(s, 3H, Ph—OCH$_3$), 5.78(s, 2H, CH$_2$), 7.06(d, 2H, J = 6.8 Hz), 7.17(s, 1H, isoxazole-H), 7.26(s, 1H), 7.84(d, 2H, J = 8.8 Hz), 8.67(s, 1H). |
| S-44 | 2.61(s, 3H, CH$_3$), 5.83(s, 2H, CH$_2$), 7.26(d, 2H, J = 1.2 Hz), 7.27(s, 1H, isoxazole-H), 7.59(d, 2H, J = 8.4 Hz), 7.92(d, 2H, J = 8.4 Hz), 8.67(s, 1H). |
| S-45 | 2.61(s, 3H, CH$_3$), 5.81(s, 2H, CH$_2$), 7.26(d, 2H, J = 1.2 Hz), 7.27(s, 1H, isoxazole-H), 7.59(d, 2H, J = 8.4 Hz), 7.92(d, 2H, J = 8.4 Hz), 8.67(s, 1H). |
| S-46 | 2.61(s, 3H, CH$_3$), 5.83(s, 2H, CH$_2$), 7.13(s, 1H, isoxazole-H), 7.26(d, 2H, J = 1.2 Hz), 7.47-7.51(m, 1H), 7.54-7.58(m, 1H), 7.64-7.67(m, 1H), 7.70-7.72(m, 1H), 8.68(s, 1H). |
| S-47 | 2.61(s, 3H, CH$_3$), 5.83(s, 2H, CH$_2$), 7.15(s, 1H, isoxazole-H), 7.26(d, 2H, J = 1.2 Hz), 7.58-7.61(m, 1H), 7.75(d, 1H, J = 8.4 Hz), 7.85(d, 1H, J = 2.0 Hz), 8.68(s, 1H). |
| S-48 | 2.61(s, 3H, CH$_3$), 5.81(s, 2H, CH$_2$), 7.26(d, 2H, J = 1.2 Hz), 7.27(s, 1H, isoxazole-H), 7.74(d, 2H, J = 8.8 Hz), 7.86(d, 2H, J = 6.4 Hz), 8.67(s, 1H). |
| S-49 | 2.61(s, 3H, CH$_3$), 5.81(s, 2H, CH$_2$), 7.26(d, 2H, J = 1.2 Hz), 7.27(s, 1H, isoxazole-H), 7.59(d, 2H, J = 8.4 Hz), 7.92(d, 2H, J = 8.4 Hz), 8.67(s, 1H). |
| S-50 | 2.61(s, 3H, CH$_3$), 3.83(s, 6H, 2OCH$_3$), 7.27(s, 1H, isoxazole-H), 7.47(d, 1H, J = 1.2 Hz), 7.58-7.60(m, 1H), 7.76(s, 1H), 7.85(d, 1H, J = 2.0 Hz), 8.65(s, 1H). |
| S-51 | 2.61(s, 3H, CH$_3$), 4.22(t, 1H, J = 6.6 Hz, NH), 5.80(s, 2H, CH$_2$), 7.24(s, 1H, isoxazole-H), 7.26-7.27(m, 1H), 7.51(d, 2H, J = 2.8 Hz), 7.52-7.53(m, 1H), 7.88-7.90(m, 2H), 8.68(s, 1H). |
| S-52 | 2.36(s, 3H, Ph—CH$_3$), 2.61(s, 3H, CH$_3$), 4.29(t, 1H, J = 6.4 Hz, NH), 5.79(s, 2H, CH$_2$), 7.20(s, 1H, isoxazole-H), 7.26(d, 1H, J = 1.2 Hz), 7.33(d, 2H, J = 8.0 Hz), 7.78(d, 2H, J = 8.0 Hz), 8.67(s, 1H). |
| S-53 | 2.61(s, 3H, CH$_3$), 3.80(s, 3H, Ph—OCH$_3$), 4.28(t, 1H, J = 6.5 Hz, NH), 5.78(s, 2H, CH$_2$), 7.06(d, 2H, J = 6.8Hz), 7.17(s, 1H, isoxazole-H), 7.26(s, 1H), 7.84(d, 2H, J = 8.8 Hz), 8.67(s, 1H). |
| S-54 | 2.61(s, 3H, CH$_3$), 4.28(t, 1H, J = 6.5 Hz, NH), 5.83(s, 2H, CH$_2$), 7.26(d, 2H, J = 1.2 Hz), 7.27(s, 1H, isoxazole-H), 7.59(d, 2H, J = 8.4 Hz), 7.92(d, 2H, J = 8.4 Hz), 8.67(s, 1H). |
| S-55 | 2.61(s, 3H, CH$_3$), 4.31(t, 1H, J = 6.5 Hz, NH), 5.81(s, 2H, CH$_2$), 7.26(d, 2H, J = 1.2 Hz), 7.27(s, 1H, isoxazole-H), 7.59(d, 2H, J = 8.4 Hz), 7.92(d, 2H, J = 8.4 Hz), 8.67(s, 1H). |
| S-56 | 2.61(s, 3H, CH$_3$), 4.33(t, 1H, J = 6.5 Hz, NH), 5.83(s, 2H, CH$_2$), 7.13(s, 1H, isoxazole-H), 7.26(d, 2H, J = 1.2 Hz), 7.47-7.51(m, 1H), 7.54-7.58(m, 1H), 7.64-7.67(m, 1H), 7.70-7.72(m, 1H), 8.68(s, 1H). |
| S-57 | 2.61(s, 3H, CH$_3$), 4.38(t, 1H, J = 6.5 Hz, NH), 5.83(s, 2H, CH$_2$), 7.15(s, 1H, isoxazole-H), 7.26(d, 2H, J = 1.2 Hz), 7.58-7.61(m, 1H), 7.75(d, 1H, J = 8.4 Hz), 7.85(d, 1H, J = 2.0 Hz), 8.68(s, 1H). |

TABLE 3-continued

<sup>1</sup>H NMR data of the compounds in Table 1

| Number | $^1$HNMR (400 MHz, DMSO-d$_6$) |
|---|---|
| S-58 | 2.61(s, 3H, CH$_3$), 4.32(t, 1H, J = 6.5 Hz, NH), 5.81(s, 2H, CH$_2$), 7.26(d, 2H, J = 1.2 Hz), 7.27(s, 1H, isoxazole-H), 7.74(d, 2H, J = 8.8 Hz), 7.86(d, 2H, J = 6.4Hz), 8.67(s, 1H). |
| S-59 | 2.61(s, 3H, CH$_3$), 4.37(t, 1H, J = 6.5 Hz, NH), 5.81(s, 2H, CH$_2$), 7.26(d, 2H, J = 1.2 Hz), 7.27(s, 1H, isoxazole-H), 7.59(d, 2H, J = 8.4 Hz), 7.92(d, 2H, J = 8.4 Hz), 8.67(s, 1H). |
| S-60 | 2.61(s, 3H, CH$_3$), 3.83(s, 6H, 2OCH$_3$), 4.26(t, 1H, J = 6.5 Hz, NH), 7.27(s, 1H, isoxazole-H), 7.47(d, 1H, J = 1.2 Hz), 7.58-7.60(m, 1H), 7.76(s, 1H), 7.85(d, 1H, J = 2.0 Hz), 8.65(s, 1H). |
| S-61 | 1.45(s, 9H, 3CH$_3$), 5.82(s, 2H, CH$_2$), 7.18(s, 1H, isoxazole-H), 7.44(s, 1H), 7.65-7.68(m, 3H), 7.78-7.80(m, 2H), 8.78(s, 1H). |
| S-62 | 1.44(s, 9H, 3CH$_3$), 2.36(s, 3H, Ph—CH$_3$), 5.82(s, 2H, CH$_2$), 7.19(s, 1H, isoxazole-H), 7.33(d, 2H, J = 8.0 Hz), 7.43(s, 1H), 7.78(d, 2H, J = 8.0 Hz), 8.78(s, 1H). |
| S-63 | 1.45(s, 9H, 3CH$_3$), 3.93(s, 3H, Ph—OCH$_3$), 5.82(s, 2H, CH$_2$), 7.08(d, 2H, J = 8.8 Hz), 7.17(s, 1H, isoxazole-H), 7.44(s, 1H), 7.84(d, 2H, J = 8.8 Hz), 8.78(s, 1H). |
| S-64 | 1.45(s, 9H, 3CH$_3$), 5.86(s, 2H, CH$_2$), 7.27(s, 1H, isoxazole-H), 7.44(s, 1H), 7.62(d, 2H, J = 8.4 Hz), 7.95(d, 2H, J = 8.4 Hz), 8.78(s, 1H). |
| S-65 | 1.45(s, 9H, 3CH$_3$), 5.85(s, 2H, CH$_2$), 7.26(s, 1H, isoxazole-H), 7.44(s, 1H), 7.60(d, 2H, J = 8.4 Hz), 7.94(d, 2H, J = 8.4 Hz), 8.78(s, 1H). |
| S-66 | 1.49(s, 9H, 3CH$_3$), 5.87(s, 2H, CH$_2$), 7.12(s, 1H, isoxazole-H), 7.44(s, 1H), 7.48-7.58(m, 2H), 7.67(d, 1H, J = 8.0 Hz), 7.73(d, 1H, J = 7.2 Hz), 8.79(s, 1H). |
| S-67 | 1.49(s, 9H, 3CH$_3$), 5.87(s, 2H, CH$_2$), 7.12(s, 1H, isoxazole-H), 7.44(s, 1H), 7.75(d, 1H, J = 8.4 Hz), 7.85(d, 1H, J = 2.0 Hz), 8.79(s, 1H). |
| S-68 | 1.45(s, 9H, 3CH$_3$), 5.85(s, 2H, CH$_2$), 7.27(s, 1H, isoxazole-H), 7.44(s, 1H), 7.74(d, 2H, J = 8.8 Hz), 7.87(d, 2H, J = 8.8 Hz), 8.78(s, 1H). |
| S-69 | 1.45(s, 9H, 3CH$_3$), 5.86(s, 2H, CH$_2$), 7.26(s, 1H, isoxazole-H), 7.44(s, 1H), 7.60(d, 2H, J = 8.4 Hz), 7.94(d, 2H, J = 8.4 Hz), 8.78(s, 1H). |
| S-70 | 1.45(s, 9H, 3CH$_3$), 3.93(s, 6H, 2OCH$_3$), 5.86(s, 2H, CH$_2$), 7.08(m, 1H), 7.17(s, 1H, isoxazole-H), 7.23-7.25(m, 2H) 7.44(s, 1H), 8.78(s, 1H). |
| S-71 | 1.45(s, 9H, 3CH$_3$), 4.22(t, 1H, J = 6.6 Hz, NH), 5.82(s, 2H, CH$_2$), 7.18(s, 1H, isoxazole-H), 7.44(s, 1H), 7.65-7.68(m, 3H), 7.78-7.80(m, 2H), 8.78(s, 1H). |
| S-72 | 1.44(s, 9H, 3CH$_3$), 2.36(s, 3H, Ph—CH$_3$), 4.29(t, 1H, J = 6.4 Hz, NH), 5.82(s, 2H, CH$_2$), 7.19(s, 1H, isoxazole-H), 7.33(d, 2H, J = 8.0 Hz), 7.43(s, 1H), 7.78(d, 2H, J = 8.0 Hz), 8.78(s, 1H). |
| S-73 | 1.45(s, 9H, 3CH$_3$), 3.93(s, 3H, Ph—OCH$_3$), 4.28(t, 1H, J = 6.5 Hz, NH), 5.82(s, 2H, CH$_2$), 7.08(d, 2H, J = 8.8 Hz), 7.17(s, 1H, isoxazole-H), 7.44(s, 1H), 7.84(d, 2H, J = 8.8 Hz), 8.78(s, 1H). |
| S-74 | 1.45(s, 9H, 3CH$_3$), 4.28(t, 1H, J = 6.5 Hz, NH), 5.86(s, 2H, CH$_2$), 7.27(s, 1H, isoxazole-H), 7.44(s, 1H), 7.62(d, 2H, J = 8.4 Hz), 7.95(d, 2H, J = 8.4 Hz), 8.78(s, 1H). |
| S-75 | 1.45(s, 9H, 3CH$_3$), 4.31(t, 1H, J = 6.5 Hz, NH), 5.85(s, 2H, CH$_2$), 7.26(s, 1H, isoxazole-H), 7.44(s, 1H), 7.60(d, 2H, J = 8.4 Hz), 7.94(d, 2H, J = 8.4 Hz), 8.78(s, 1H). |
| S-76 | 1.49(s, 9H, 3CH$_3$), 4.33(t, 1H, J = 6.5 Hz, NH), 5.87(s, 2H, CH$_2$), 7.12(s, 1H, isoxazole-H), 7.44(s, 1H), 7.48-7.58(m, 2H), 7.67(d, 1H, J = 8.0 Hz), 7.73(d, 1H, J = 7.2 Hz), 8.79(s, 1H). |
| S-77 | 1.49(s, 9H, 3CH$_3$), 4.38(t, 1H, J = 6.5 Hz, NH), 5.87(s, 2H, CH$_2$), 7.12(s, 1H, isoxazole-H), 7.44(s, 1H), 7.75(d, 1H, J = 8.4 Hz), 7.85(d, 1H, J = 2.0 Hz), 8.79(s, 1H). |
| S-78 | 1.45(s, 9H, 3CH$_3$), 4.32(t, 1H, J = 6.5 Hz, NH), 5.85(s, 2H, CH$_2$), 7.27(s, 1H, isoxazole-H), 7.44(s, 1H), 7.74(d, 2H, J = 8.8 Hz), 7.87(d, 2H, J = 8.8 Hz), 8.78(s, 1H). |
| S-79 | 1.45(s, 9H, 3CH$_3$), 4.37(t, 1H, J = 6.5 Hz, NH), 5.86(s, 2H, CH$_2$), 7.26(s, 1H, isoxazole-H), 7.44(s, 1H), 7.60(d, 2H, J = 8.4 Hz), 7.94(d, 2H, J = 8.4 Hz), 8.78(s, 1H). |
| S-80 | 1.45(s, 9H, 3CH$_3$), 3.93(s, 6H, 2OCH$_3$), 4.26(t, 1H, J = 6.5 Hz, NH), 5.86(s, 2H, CH$_2$), 7.08(m, 1H), 7.17(s, 1H, isoxazole-H), 7.23-7.25(m, 2H) 7.44(s, 1H), 8.78(s, 1H). |
| S-81 | 1.34(t, 3H, CH$_2$CH$_3$, J = 7.2 Hz), 2.92(q, 2H, CH$_2$CH$_3$, J = 0.8 Hz), 5.81(s, 2H, CH$_2$), 7.25(s, 1H, isoxazole-H), 7.26-7.27(m, 1H), 7.51-7.53(m, 3H), 7.88-7.91 (m, 2H), 8.68(s, 1H). |
| S-82 | 1.34(t, 3H, CH$_2$CH$_3$, J = 7.6 Hz), 2.36(s, 3H, Ph—CH$_3$), 2.97(q, 2H, CH$_2$CH$_3$, J = 1.2 Hz), 5.79(s, 2H, CH$_2$), 7.21(s, 1H, isoxazole-H), 7.27(s, 1H), 7.31(d, 2H, J = 7.6 Hz), 7.79(d, 2H, J = 8.4 Hz), 8.68(s, 1H). |
| S-83 | 1.32(t, 3H, CH$_2$CH$_3$, J = 7.6 Hz), 2.97(q, 2H, CH$_2$CH$_3$, J = 1.2 Hz), 3.93(s, 3H, Ph—OCH$_3$), 5.78(s, 2H, CH$_2$), 7.08(d, 2H, J = 8.8 Hz), 7.18(s, 1H, isoxazole-H), 7.26(s, 1H), 7.83(d, 2H, J = 8.8 Hz), 8.67(s, 1H). |
| S-84 | 1.32(t, 3H, CH$_2$CH$_3$, J = 7.6 Hz), 2.96(q, 2H, CH$_2$CH$_3$, J = 1.2 Hz), 5.81 (s, 2H, CH$_2$), 7.26(s, 1H, isoxazole-H), 7.28(s, 1H), 7.60(d, 2H, J = 8.8 Hz), 7.93(d, 2H, J = 8.8 Hz), 8.68(s, 1H). |
| S-85 | 1.32(t, 3H, CH$_2$CH$_3$, J = 7.6 Hz), 2.96(q, 2H, CH$_2$CH$_3$, J = 1.2 Hz), 5.81 (s, 2H, CH$_2$), 7.26(s, 1H, isoxazole-H), 7.28(s, 1H), 7.60(d, 2H, J = 8.8 Hz), 7.93(d, 2H, J = 8.8 Hz), 8.68(s, 1H). |
| S-86 | 1.33(t, 3H, CH$_2$CH$_3$, J = 7.6 Hz), 2.97(q, 2H, CH$_2$CH$_3$, J = 1.2 Hz), 5.83 (s, 2H, CH$_2$), 7.13(s, 1H, isoxazole-H), 7.27(s, 1H), 7.47-7.58(m, 2H), 7.64-7.66(m, 1H), 7.67-7.72 (m, 1H), 8.69(s, 1H). |
| S-87 | 1.33(t, 3H, CH$_2$CH$_3$, J = 7.6 Hz), 2.95(q, 2H, CH$_2$CH$_3$, J = 1.2 Hz), 5.83 (s, 2H, CH$_2$), 7.16(s, 1H, isoxazole-H), 7.26(s, 1H), 7.58-7.60(m, 1H), 7.75(d, 1H, J = 8.4 Hz), 7.85(s, 1H), 8.69(s, 1H). |
| S-88 | 1.32(t, 3H, CH$_2$CH$_3$, J = 7.6 Hz), 2.96(q, 2H, CH$_2$CH$_3$, J = 1.2 Hz), 5.81 (s, 2H, CH$_2$), 7.27(s, 1H, isoxazole-H), 7.28(s, 1H), 7.74(d, 2H, J = 8.4 Hz), 7.86(d, 1H, J = 8.4 Hz), 8.66(s, 1H). |

TABLE 3-continued

<sup>1</sup>H NMR data of the compounds in Table 1

| Number | <sup>1</sup>HNMR (400 MHz, DMSO-d$_6$) |
|---|---|
| S-89 | 1.32(t, 3H, CH$_2$CH$_3$, J = 7.6 Hz), 2.96(q, 2H, CH$_2$CH$_3$, J = 1.2 Hz), 5.81 (s, 2H, CH$_2$), 7.27(s, 1H, isoxazole-H), 7.28(s, 1H), 7.74(d, 1H, J = 8.4 Hz), 7.86(d, 1H, J = 8.4 Hz), 8.66(s, 1H). |
| S-90 | 1.34(t, 3H, CH$_2$CH$_3$, J = 7.2 Hz), 2.92(q, 2H, CH$_2$CH$_3$, J = 0.8 Hz), 3.83(s, 6H, 2OCH$_3$), 5.81(s, 2H, CH$_2$), 7.25(s, 1H, isoxazole-H), 7.23-7.24(m, 2H), 7.62(d, 1H, J = 2.0 Hz), 8.70(s, 1H). |
| S-91 | 1.34(t, 3H, CH$_2$CH$_3$, J = 7.2 Hz), 2.92(q, 2H, CH$_2$CH$_3$, J = 0.8 Hz), 4.22(t, 1H, J = 6.6 Hz, NH), 5.81(s, 2H, CH$_2$), 7.25(s, 1H, isoxazole-H), 7.26-7.27(m, 1H), 7.51-7.53(m, 3H), 7.88-7.91 (m, 2H), 8.68(s, 1H). |
| S-92 | 1.34(t, 3H, CH$_2$CH$_3$, J = 7.6 Hz), 2.36(s, 3H, Ph—CH$_3$), 2.97(q, 2H, CH$_2$CH$_3$, J = 1.2 Hz), 4.29(t, 1H, J = 6.4 Hz, NH), 5.79(s, 2H, CH$_2$), 7.21(s, 1H, isoxazole-H), 7.27(s, 1H), 7.31(d, 2H, J = 7.6 Hz), 7.79(d, 2H, J = 8.4 Hz), 8.68(s, 1H). |
| S-93 | 1.32(t, 3H, CH$_2$CH$_3$, J = 7.6 Hz), 2.97(q, 2H, CH$_2$CH$_3$, J = 1.2 Hz), 3.93(s, 3H, Ph—OCH$_3$), 4.28(t, 1H, J = 6.5 Hz, NH), 5.78(s, 2H, CH$_2$), 7.08(d, 2H, J = 8.8 Hz), 7.18(s, 1H, isoxazole-H), 7.26(s, 1H), 7.83(d, 2H, J = 8.8 Hz), 8.67(s, 1H). |
| S-94 | 1.32(t, 3H, CH$_2$CH$_3$, J = 7.6 Hz), 2.96(q, 2H, CH$_2$CH$_3$, J = 1.2 Hz), 4.28(t, 1H, J = 6.5 Hz, NH), 5.81 (s, 2H, CH$_2$), 7.26(s, 1H, isoxazole-H), 7.28(s, 1H), 7.60(d, 2H, J = 8.8 Hz), 7.93(d, 2H, J = 8.8 Hz), 8.68(s, 1H). |
| S-95 | 1.32(t, 3H, CH$_2$CH$_3$, J = 7.6 Hz), 2.96(q, 2H, CH$_2$CH$_3$, J = 1.2 Hz), 4.31(t, 1H, J = 6.5 Hz, NH), 5.81 (s, 2H, CH$_2$), 7.26(s, 1H, isoxazole-H), 7.28(s, 1H), 7.60(d, 2H, J = 8.8 Hz), 7.93(d, 2H, J = 8.8 Hz), 8.68(s, 1H). |
| S-96 | 1.33(t, 3H, CH$_2$CH$_3$, J = 7.6 Hz), 2.97(q, 2H, CH$_2$CH$_3$, J = 1.2 Hz), 4.33(t, 1H, J = 6.5 Hz, NH), 5.83 (s, 2H, CH$_2$), 7.13(s, 1H, isoxazole-H), 7.27(s, 1H), 7.47-7.58(m, 2H), 7.64-7.66(m, 1H), 7.67-7.72 (m, 1H), 8.69(s, 1H). |
| S-97 | 1.33(t, 3H, CH$_2$CH$_3$, J = 7.6 Hz), 2.95(q, 2H, CH$_2$CH$_3$, J = 1.2 Hz), 4.38(t, 1H, J = 6.5 Hz, NH), 5.83 (s, 2H, CH$_2$), 7.16(s, 1H, isoxazole-H), 7.26(s, 1H), 7.58-7.60(m, 1H), 7.75(d, 1H, J = 8.4 Hz), 7.85(s, 1H), 8.69(s, 1H). |
| S-98 | 1.32(t, 3H, CH$_2$CH$_3$, J = 7.6 Hz), 2.96(q, 2H, CH$_2$CH$_3$, J = 1.2 Hz), 4.32(t, 1H, J = 6.5 Hz, NH), 5.81 (s, 2H, CH$_2$), 7.27(s, 1H, isoxazole-H), 7.28(s, 1H), 7.74(d, 1H, J = 8.4 Hz), 7.86(d, 1H, J = 8.4 Hz), 8.66(s, 1H). |
| S-99 | 1.32(t, 3H, CH$_2$CH$_3$, J = 7.6 Hz), 2.96(q, 2H, CH$_2$CH$_3$, J = 1.2 Hz), 4.37(t, 1H, J = 6.5 Hz, NH), 5.81 (s, 2H, CH$_2$), 7.27(s, 1H, isoxazole-H), 7.28(s, 1H), 7.74(d, 1H, J = 8.4 Hz), 7.86(d, 1H, J = 8.4 Hz), 8.66(s, 1H). |
| S-100 | 1.34(t, 3H, CH$_2$CH$_3$, J = 7.2 Hz), 2.92(q, 2H, CH$_2$CH$_3$, J = 0.8 Hz), 3.83(s, 6H, 2OCH$_3$), 4.26(t, 1H, J = 6.5 Hz, NH), 5.81(s, 2H, CH$_2$), 7.25(s, 1H, isoxazole-H), 7.23-7.24(m, 2H), 7.62(d, 1H, J = 2.0 Hz), 8.70(s, 1H). |
| S-101 | 2.44(s, 3H, CH$_3$), 2.47(s, 3H, CH$_3$), 5.80(s, 2H, CH$_2$), 7.21(s, 1H, isoxazole-H), 7.51-7.52(m, 3H), 7.88-7.90(m, 2H), 8.62(s, 1H). |
| S-102 | 2.21(s, 3H, CH$_3$), 2.26(s, 3H, CH$_3$), 2.51(s, 3H, CH$_3$), 5.80(s, 2H, CH$_2$), 7.16(s, 1H, isoxazole-H), 7.33(d, 1H, J = 7.6 Hz), 7.79(d, 1H, J = 6.8 Hz), 8.62(s, 1H). |
| S-103 | 2.43(s, 3H, CH$_3$), 2.47(s, 3H, CH$_3$), 3.82(s, 3H, Ph—OCH$_3$), 5.78(s, 2H, CH$_2$), 7.05(d, 2H, J = 8.8 Hz), 7.14(s, 1H, isoxazole-H), 7.84(d, 2H, J = 8.8 Hz), 8.62(s, 1H). |
| S-104 | 2.43(s, 3H, CH$_3$), 2.49(s, 3H, CH$_3$), 5.78(s, 2H, CH$_2$), 7.24(s, 1H, isoxazole-H), 7.60(d, 2H, J = 8.4 Hz), 7.94(d, 2H, J = 8.8 Hz), 8.62(s, 1H). |
| S-105 | 2.43(s, 3H, CH$_3$), 2.49(s, 3H, CH$_3$), 5.78(s, 2H, CH$_2$), 7.24(s, 1H, isoxazole-H), 7.60(d, 2H, J = 8.4 Hz), 7.94(d, 2H, J = 8.8 Hz), 8.62(s, 1H). |
| S-106 | 2.43(s, 3H, CH$_3$), 2.47(s, 3H, CH$_3$), 5.82(s, 2H, CH$_2$), 7.24(s, 1H, isoxazole-H), 7.47-7.58(m, 2H), 7.64-7.66(m, 1H), 7.71-7.73(m, 1H), 8.63(s, 1H). |
| S-107 | 2.43(s, 3H, CH$_3$), 2.47(s, 3H, CH$_3$), 5.80(s, 2H, CH$_2$), 7.24(s, 1H, isoxazole-H), 7.26(s, 1H), 7.58-7.60(m, 1H), 7.75(d, 1H, J = 8.4 Hz), 7.85(s, 1H), 8.69(s, 1H). |
| S-108 | 2.43(s, 3H, CH$_3$), 2.47(s, 3H, CH$_3$), 5.80(s, 2H, CH$_2$), 7.24(s, 1H, isoxazole-H), 7.73(d, 2H, J = 8.8 Hz), 7.86(d, 2H, J = 8.4 Hz), 8.62(s, 1H). |
| S-109 | 2.43(s, 3H, CH$_3$), 2.47(s, 3H, CH$_3$), 5.80(s, 2H, CH$_2$), 7.24(s, 1H, isoxazole-H), 7.73(d, 2H, J = 8.8 Hz), 7.86(d, 2H, J = 8.4 Hz), 8.62(s, 1H). |
| S-110 | 2.44(s, 3H, CH$_3$), 2.47(s, 3H, CH$_3$), 3.83(s, 6H, 2OCH$_3$), 5.80(s, 2H, CH$_2$), 7.21(s, 1H, isoxazole-H), 7.23-7.24(m, 2H), 7.62(d, 1H, J = 2.0 Hz), 8.62(s, 1H). |
| S-111 | 2.44(s, 3H, CH$_3$), 2.47(s, 3H, CH$_3$), 4.22(t, 1H, J = 6.6 Hz, NH), 5.80(s, 2H, CH$_2$), 7.21(s, 1H, isoxazole-H), 7.51-7.52(m, 3H), 7.88-7.90(m, 2H), 8.62(s, 1H). |
| S-112 | 2.21(s, 3H, CH$_3$), 2.26(s, 3H, CH$_3$), 2.51(s, 3H, CH$_3$), 4.29(t, 1H, J = 6.4 Hz, NH), 5.80(s, 2H, CH$_2$), 7.16(s, 1H, isoxazole-H), 7.33(d, 1H, J = 7.6 Hz), 7.79(d, 1H, J = 6.8 Hz), 8.62(s, 1H). |
| S-113 | 2.43(s, 3H, CH$_3$), 2.47(s, 3H, CH$_3$), 3.82(s, 3H, Ph—OCH$_3$), 4.28(t, 1H, J = 6.5 Hz, NH), 5.78(s, 2H, CH$_2$), 7.05(d, 2H, J = 8.8 Hz), 7.14(s, 1H, isoxazole-H), 7.84(d, 2H, J = 8.8 Hz), 8.62(s, 1H). |
| S-114 | 2.43(s, 3H, CH$_3$), 2.49(s, 3H, CH$_3$), 4.28(t, 1H, J = 6.5 Hz, NH), 5.78(s, 2H, CH$_2$), 7.24(s, 1H, isoxazole-H), 7.60(d, 2H, J = 8.4 Hz), 7.94(d, 2H, J = 8.8 Hz), 8.62(s, 1H). |
| S-115 | 2.43(s, 3H, CH$_3$), 2.49(s, 3H, CH$_3$), 4.31(t, 1H, J = 6.5 Hz, NH), 5.78(s, 2H, CH$_2$), 7.24(s, 1H, isoxazole-H), 7.60(d, 2H, J = 8.4 Hz), 7.94(d, 2H, J = 8.8 Hz), 8.62(s, 1H). |
| S-116 | 2.43(s, 3H, CH$_3$), 2.49(s, 3H, CH$_3$), 4.33(t, 1H, J = 6.5 Hz, NH), 5.82(s, 2H, CH$_2$), 7.24(s, 1H, isoxazole-H), 7.47-7.58(m, 2H), 7.64-7.66(m, 1H), 7.71-7.73(m, 1H), 8.63(s, 1H). |
| S-117 | 2.43(s, 3H, CH$_3$), 2.47(s, 3H, CH$_3$), 4.38(t, 1H, J = 6.5 Hz, NH), 5.80(s, 2H, CH$_2$), 7.24(s, 1H, isoxazole-H), 7.26(s, 1H), 7.58-7.60(m, 1H), 7.75(d, 1H, J = 8.4 Hz), 7.85(s, 1H), 8.69(s, 1H). |
| S-118 | 2.43(s, 3H, CH$_3$), 2.47(s, 3H, CH$_3$), 4.32(t, 1H, J = 6.5 Hz, NH), 5.80(s, 2H, CH$_2$), 7.24(s, 1H, isoxazole-H), 7.73(d, 2H, J = 8.8 Hz), 7.86(d, 2H, J = 8.4 Hz), 8.62(s, 1H). |

TABLE 3-continued

¹H NMR data of the compounds in Table 1

| Number | ¹HNMR (400 MHz, DMSO-d$_6$) |
|---|---|
| S-119 | 2.43(s, 3H, CH$_3$), 2.47(s, 3H, CH$_3$), 4.37(t, 1H, J = 6.5 Hz, NH), 5.80(s, 2H, CH$_2$), 7.24(s, 1H, isoxazole-H), 7.73(d, 2H, J = 8.8 Hz), 7.86(d, 2H, J = 8.4 Hz), 8.62(s, 1H). |
| S-120 | 2.44(s, 3H, CH$_3$), 2.47(s, 3H, CH$_3$), 3.83(s, 6H, 2OCH$_3$), 4.26(t, 1H, J = 6.5 Hz, NH), 5.80(s, 2H, CH$_2$), 7.21(s, 1H, isoxazole-H), 7.23-7.24(m, 2H), 7.62(d, 1H, J = 2.0 Hz), 8.62(s, 1H). |
| S-121 | 1.82-1.84(m, 4H, 2CH$_2$), 2.82-2.84(m, 2H, CH$_2$), 2.91-2.93(m, 2H, CH$_2$), 5.78(s, 2H, CH$_2$), 7.20(s, 1H, isoxazole-H), 7.51-7.52 (m, 3H), 7.88-7.90(m, 2H), 8.63(s, 1H). |
| S-122 | 1.82-1.84(m, 4H, 2CH$_2$), 2.49-2.50(m, 2H, CH$_2$), 2.51-2.52(m, 2H, CH$_2$), 5.78(s, 2H, CH$_2$), 7.16(s, 1H, isoxazole-H), 7.33(d, 2H, J = 8.0 Hz), 7.78(d, 2H, J = 8.0 Hz), 8.62(s, 1H). |
| S-123 | 1.82-1.84(m, 4H, 2CH$_2$), 2.84-2.86(m, 2H, CH$_2$), 2.88-2.91(m, 2H, CH$_2$), 3.92(s, 3H, Ph—OCH$_3$), 5.78(s, 2H, CH$_2$), 7.07(d, 2H, J = 8.8 Hz), 7.13(s, 1H, isoxazole-H), 7.82(d, 2H, J = 8.8 Hz), 8.62(s, 1H). |
| S-124 | 1.82-1.84(m, 4H, 2CH$_2$), 2.83-2.87(m, 2H, CH$_2$), 2.88-2.90(m, 2H, CH$_2$), 5.79(s, 2H, CH$_2$), 7.23(s, 1H, isoxazole-H), 7.73(d, 1H, J = 8.4 Hz), 7.86(d, 1H, J = 8.4 Hz), 8.62(s, 1H). |
| S-125 | 181-1.87(m, 4H), 2.82-2.83(m, 2H), 2.91-2.93(m, 2H), 5.79(s, 2H, CH$_2$), 7.23(s, 1H, isoxazole-H), 7.59(d, 2H, J = 8.4 Hz), 7.93(d, 2H, J = 8.8 Hz), 8.62(s, 1H). |
| S-126 | 1.82-1.85(m, 4H, 2CH$_2$), 2.84-2.86(m, 2H, CH$_2$), 2.89-2.92(m, 2H, CH$_2$), 5.81(s, 2H, CH$_2$), 7.09(s, 1H, isoxazole-H), 7.47-7.58(m, 2H), 7.64-7.73(m, 2H), 8.63(s, 1H). |
| S-127 | 1.82-1.83(m, 4H, 2CH$_2$), 2.82-2.84(m, 2H, CH$_2$), 2.91-2.93(m, 2H, CH$_2$), 5.81(s, 2H, CH$_2$), 7.11(s, 1H, isoxazole-H), 7.58-7.60(m, 1H), 7.74-7.76(m, 1H), 7.85(d, 1H, J = 2.0 Hz), 8.63(s, 1H). |
| S-128 | 1.82-1.83(m, 4H, 2CH$_2$), 2.84-2.87(m, 2H, CH$_2$), 2.88-2.91(m, 2H, CH$_2$), 5.79(s, 2H, CH$_2$), 7.23(s, 1H, isoxazole-H), 7.73(d, 1H, J = 8.4 Hz), 7.86(d, 1H, J = 8.4 Hz), 8.62(s, 1H). |
| S-129 | 1.82-1.83(m, 4H, 2CH$_2$), 2.84-2.87(m, 2H, CH$_2$), 2.88-2.90(m, 2H, CH$_2$), 5.79(s, 2H, CH$_2$), 7.18(s, 1H, isoxazole-H), 7.75(d, 2H, J = 8.4 Hz), 7.86(d, 2H, J = 8.4 Hz), 8.63(s, 1H). |
| S-130 | 1.82-1.83(m, 4H, 2CH$_2$), 2.84-2.87(m, 2H, CH$_2$), 3.83(s, 6H, 2OCH$_3$), 5.79(s, 2H, CH$_2$), 7.18(s, 1H, isoxazole-H), 7.72(d, 2H, J = 8.4 Hz), 7.78(d, 2H, J = 8.4 Hz), 8.63(s, 1H). |
| S-131 | 1.82-1.84(m, 4H, 2CH$_2$), 2.83-2.85(m, 2H, CH$_2$), 2.90-2.93(m, 2H, CH$_2$), 4.28(t, 1H, J = 6.5 Hz, NH), 5.78(s, 2H, CH$_2$), 7.20(s, 1H, isoxazole-H), 7.51-7.52 (m, 3H), 7.88-7.90(m, 2H), 8.63(s, 1H). |
| S-132 | 1.82-1.84(m, 4H, 2CH$_2$), 2.50(t, 2H, J = 4.8 Hz, CH$_2$), 2.51(t, 2H, J = 4.6 Hz, CH$_2$), 4.27(t, 1H, J = 6.5 Hz, NH), 5.78(s, 2H, CH$_2$), 7.16(s, 1H, isoxazole-H), 7.33(d, 2H, J = 8.0 Hz), 7.78(d, 2H, J = 8.0 Hz), 8.62(s, 1H). |
| S-133 | 1.82-1.84(m, 4H, 2CH$_2$), 2.84-2.86(m, 2H, CH$_2$), 2.88-2.91(m, 2H, CH$_2$), 3.92(s, 3H, Ph—OCH$_3$), 4.27(t, 1H, J = 6.5 Hz, NH), 5.78(s, 2H, CH$_2$), 7.07(d, 2H, J = 8.8 Hz), 7.13(s, 1H, isoxazole-H), 7.82(d, 2H, J = 8.8 Hz), 8.62(s, 1H). |
| S-134 | 1.82-1.84(m, 4H, 2CH$_2$), 2.83-2.87(m, 2H, CH$_2$), 2.88-2.90(m, 2H, CH$_2$), 4.27(t, 1H, J = 6.5 Hz, NH), 5.79(s, 2H, CH$_2$), 7.23(s, 1H, isoxazole-H), 7.73(d, 1H, J = 8.4 Hz), 7.86(d, 1H, J = 8.4 Hz), 8.62(s, 1H). |
| S-135 | 181-1.87(m, 4H), 2.82-2.83(m, 2H), 2.91-2.93(m, 2H), 4.31(t, 1H, J = 6.5 Hz, NH), 5.79(s, 2H, CH$_2$), 7.23(s, 1H, isoxazole-H), 7.59(d, 2H, J = 8.4 Hz), 7.93(d, 2H, J = 8.8 Hz), 8.62(s, 1H). |
| S-136 | 1.82-1.85(m, 4H, 2CH$_2$), 2.84-2.86(m, 2H, CH$_2$), 2.89-2.92(m, 2H, CH$_2$), 4.26(t, 1H, J = 6.5 Hz, NH), 5.81(s, 2H, CH$_2$), 7.09(s, 1H, isoxazole-H), 7.47-7.58(m, 2H), 7.64-7.73(m, 2H), 8.63(s, 1H). |
| S-137 | 1.82-1.83(m, 4H, 2CH$_2$), 2.82-2.84(m, 2H, CH$_2$), 2.91-2.93(m, 2H, CH$_2$), 4.28(t, 1H, J = 6.5 Hz, NH), 5.81(s, 2H, CH$_2$), 7.11(s, 1H, isoxazole-H), 7.58-7.60(m, 1H), 7.74-7.76(m, 1H), 7.85(d, 1H, J = 2.0 Hz), 8.63(s, 1H). |
| S-138 | 1.82-1.83(m, 4H, 2CH$_2$), 2.84-2.87(m, 2H, CH$_2$), 2.88-2.91(m, 2H, CH$_2$), 4.28(t, 1H, J = 6.5 Hz, NH), 5.79(s, 2H, CH$_2$), 7.23(s, 1H, isoxazole-H), 7.73(d, 1H, J = 8.4 Hz), 7.86(d, 1H, J = 8.4 Hz), 8.62(s, 1H). |
| S-139 | 1.82-1.83(m, 4H, 2CH$_2$), 2.84-2.87(m, 2H, CH$_2$), 2.88-2.90(m, 2H, CH$_2$), 4.27(t, 1H, J = 6.5 Hz, NH), 5.79(s, 2H, CH$_2$), 7.18(s, 1H, isoxazole-H), 7.75(d, 2H, J = 8.4 Hz), 7.86(d, 2H, J = 8.4 Hz), 8.63(s, 1H). |
| S-140 | 1.82-1.83(m, 4H, 2CH$_2$), 2.84-2.87(m, 2H, CH$_2$), 3.83(s, 6H, 2OCH$_3$), 4.26(t, 1H, J = 6.5 Hz, NH), 5.79(s, 2H, CH$_2$), 7.18(s, 1H, isoxazole-H), 7.72(d, 2H, J = 8.4 Hz), 7.78(d, 2H, J = 8.4 Hz), 8.63(s, 1H). |

Example 4

Synthesis of Pharmaceutically Acceptable Salts of the Compounds of the Present Invention The synthesis of said salts was illustrated by means of the description of the hydrochloride and acetate of 5-methyl-4-((3-phenyl-isoxazol-5-yl)-methoxy-)-thieno[2,3-d]pyrimidine. The salts of the other compounds were prepared in a similar manner.

(1) Preparation of 5-methyl-4-((3-phenyl-isoxazol-5-yl)-methoxy-)-thieno[2,3-d]pyrimidine hydrochloride 0.5 mmol of 5-methyl-4-((3-phenyl-isoxazol-5-yl)-methoxy-)-thieno[2,3-d]pyrimidine was added in 20 ml of 5% mixing solution of hydrochloric acid solution and methanol (V:V, 1:1). Then the mixture was dissolved under stirring with slightly heating and slowly evaporated at room temperature to afford 5-methyl-4-((3-phenyl-isoxazol-5-yl)-methoxy-)-thieno[2,3-d]pyrimidine hydrochloride as a white solid in 72% yield.

(2) Preparation of 5-methyl-4-((3-phenyl-isoxazol-5-yl)-methoxy-)-thieno[2,3-d]pyrimidine acetate 0.5 mmol of 5-methyl-4-((3-phenyl-isoxazol-5-yl)-methoxy-)-thieno[2,3-d]pyrimidine was added into a 50 ml single-necked round-bottom flask containing 10 ml of dry dichloromethane. 2 ml of acetic acid was added under stirring, and the mixture was stirred for 1-2 hours at 30-40. The mixture was cooled down, crystallized, filtered and dried under vacuum to afford 5-methyl-4-((3-phenyl-isoxazol-5-yl)-methoxy-)-thieno[2,3-d]pyrimidine acetate as a colorless solid in 58% yield.

Example 5

The inhibitory activity against colon cancer cell lines (HCT-116) and human lung cancer cell lines (A549) were screened with an SRB method. The procedure of screening was described in the reference (Li M. H., Miao Z. H., Tan W. F. et al. Clin. Cancer Res. 2004, 10(24): 8266-8274).

Detailed experimental procedure is as follows:

(1) According to the growth rate of tumor cells, colon cancer cell lines (HCT-116) in logarithmic growth phase were inoculated in 96-well culture plates and allowed to adhere to the wall for 24 h. The medicants with a concentration of $1 \times 10^{-4}$ M were added. Three replicate wells were set for the concentration, and saline control and non-apoptotic well of the corresponding concentration were set. The tumor/cancer cells were incubated for 72 hours at 37 in 5% $CO_2$; (2) the plates were taken out, and the cells were fixed in each well with 10% cold triacetic acid (TCA) solution at 4 for 1 hour; (3) the fixation fluid was removed, and the plates were rinsed 5 times with distilled water and naturally dried in air; (4) SRB solution prepared from glacial acetic acid (1%) was added to stain at room temperature for 15 min; (5) the supernatant was removed, and the residue was washed 5 times with 1% acetic acid and air-dried; (6) finally Tris solution was added and the plates were shaken on a plate shaker for 5 min. Absorbance value at 560 nm ($A_{560}$) was determined by using a wavelength-tunable microplate reader. Enzyme inhibitory ratio was calculated with the following formula:

$$\text{Inhibitory ratio}(\%) = \frac{A_{560 \text{ control group}} - A_{560 \text{ treated group}}}{A_{560 \text{ control group}}} \times 100\%$$

The activities of the compounds represented by formula (I) or salts thereof of inhibiting colon cancer cell lines (HCT-116) and human lung cancer cell lines A549 at a concentration of $1 \times 10^{-4}$ M were determined. The results are shown in Table 5 and Table 6.

TABLE 5

Testing results of the activity to inhibit colon cancer cell lines (HCT-116) of the compounds in some examples of formula (I)

| Compound number | Inhibitory ratio (%) |
| --- | --- |
| S-3 | 70.0 |
| S-83 | 69.6 |
| S-87 | 72.7 |
| S-88 | 60.9 |
| S-101 | 68.8 |
| S-102 | 62.9 |
| S-103 | 71.1 |
| S-107 | 72.9 |

TABLE 6

Testing results of the activity to inhibit human lung cancer cell lines A549 of the compounds in some examples of formula (I)

| Compound number | Inhibitory ratio (%) |
| --- | --- |
| S-1 | 85.0 |
| S-2 | 80.0 |
| S-3 | 86.4 |
| S-5 | 80.8 |
| S-6 | 75.6 |
| S-8 | 85.9 |
| S-83 | 89.4 |
| S-101 | 88.0 |
| S-106 | 71.6 |
| S-121 | 54.1 |

The invention claimed is:

1. A thieno[2,3-d]pyrimidine compound of formula (I), or a pharmaceutically acceptable salt or solvate thereof,

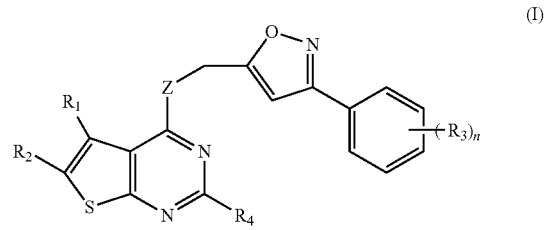

wherein:

$R_1$ and $R_2$ are the same or different and are independently selected from H, $C_{1-6}$ alkyl, $C_{1-6}$ alkoxy, halo-$C_{1-6}$ alkyl, halo-$C_{1-6}$ alkoxy, hydroxyl substituted $C_{1-6}$ alkyl, aryl group optionally substituted by $R^7$, or heteroaryl group optionally substituted by $R^8$;

Z is —$NR_5$—, $C(R_6)_2$, —S—, or —O—, in which $R_5$ is H or $C_{1-6}$ alkyl, and $R_6$ is the same or different, selected from H, $C_{1-6}$ alkyl, halo-$C_{1-6}$ alkyl, or hydroxyl substituted $C_{1-6}$ alkyl;

$R_3$ is selected from H, halogen, $C_{1-6}$ alkyl, $C_{1-6}$ alkoxy, halo-$C_{1-6}$ alkyl, halo-$C_{1-6}$ alkoxy, or hydroxyl substituted $C_{1-6}$ alkyl;

n is an integer of 0-5;

$R_4$ is selected from H, $C_{1-6}$ alkyl, $C_{1-6}$ alkoxy, halo-$C_{1-6}$ alkyl, halo-$C_{1-6}$ alkoxy, aryl group optionally substituted by $R^9$, or heteroaryl group optionally substituted by $R^{10}$; and $R^7$, $R^8$, $R^9$, and $R^{10}$ are independently selected from H, hydroxy, mercapto, cyano, amino, $C_{1-6}$ alkylamino, di($C_{1-6}$ alkyl)amino, nitro, halogen, $C_{1-6}$ alkyl, $C_{1-6}$ alkoxy, $C_{1-6}$ alkylthio, carboxy, halo-$C_{1-6}$ alkyl, halo-$C_{1-6}$ alkoxy or halo-$C_{1-6}$ alkylthio, wherein the following compounds are disclaimed:

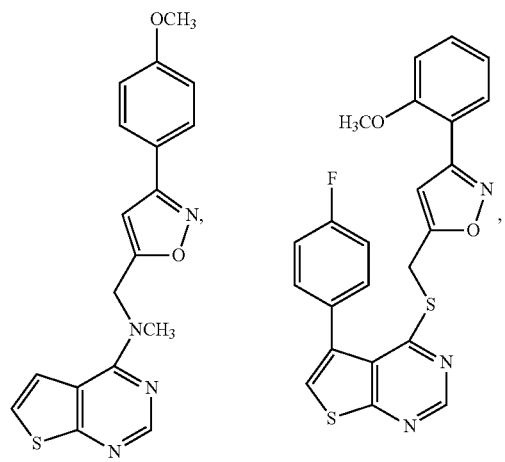

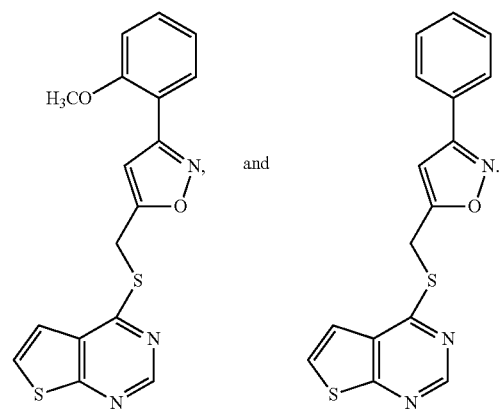

2. The thieno[2,3-d]pyrimidine compound, or the pharmaceutically acceptable salt or solvate thereof according to claim 1, wherein $R_1$ and $R_2$ are the same or different and is independently selected from H, $C_{1-3}$ alkyl, $C_{1-6}$ alkoxy, halo-$C_{1-6}$ alkyl, halo-$C_{1-6}$ alkoxy, phenyl, or $R^7$-substituted phenyl group, and $R_4$ is selected from H, $C_{1-6}$ alkyl, $C_{1-6}$ alkoxy, halo-$C_{1-6}$ alkyl, phenyl, or $R^9$-substituted phenyl group.

3. The thieno[2,3-d]pyrimidine compound, or the pharmaceutically acceptable salt or solvate according to claim 1, wherein $R_1$ and $R_2$ are independently selected from H, $C_{1-3}$ alkyl, phenyl, or $R^7$-substituted phenyl group, Z is —NH—, $CH_2$, or —O—;

$R_3$ is selected from H, fluoro, chloro, bromo, methyl, methoxy, or trifluoromethyl;

n is 1-4; and $R_4$ is selected from H, $C_{1-6}$ alkyl, $C_{1-6}$ alkoxy or halo-$C_{1-6}$ alkyl, phenyl, or $R^9$-substituted phenyl group.

4. The thieno[2,3-d]pyrimidine compound, or the pharmaceutically acceptable salt or solvate of claim 1, wherein said thieno[2,3-d]pyrimidine compound is selected from:

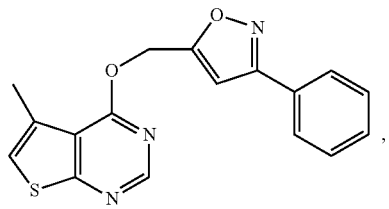

S-1

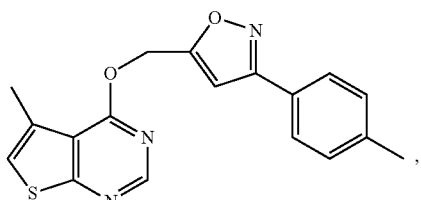

S-2

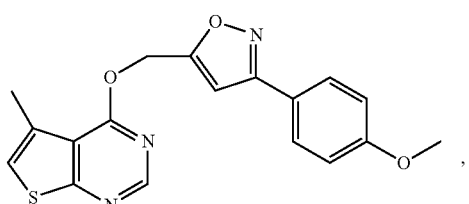

S-3

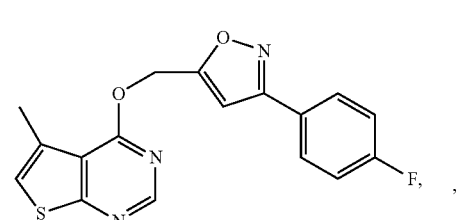

S-4

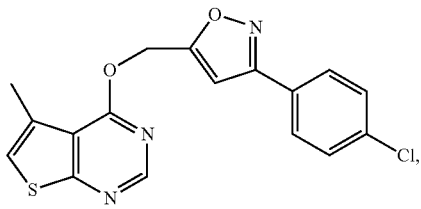

S-5

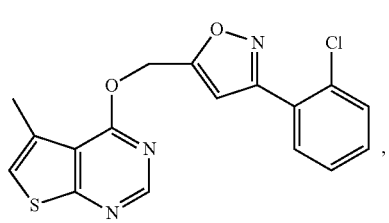

S-6

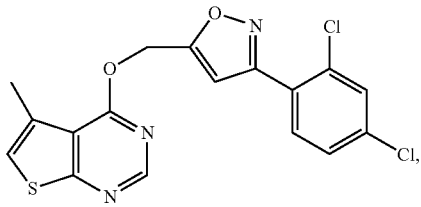

S-7

-continued
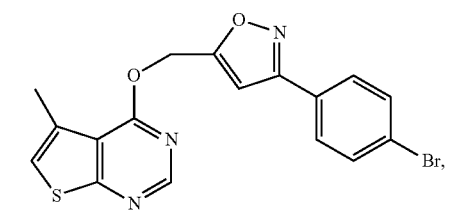
S-8
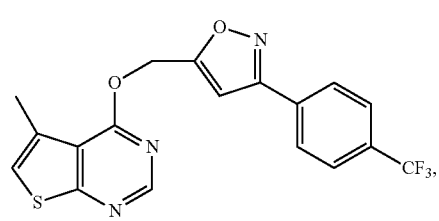
S-9
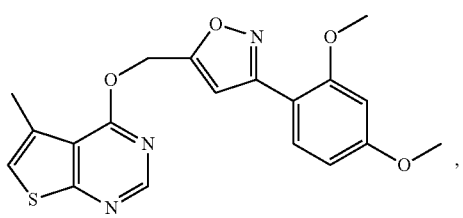
S-10
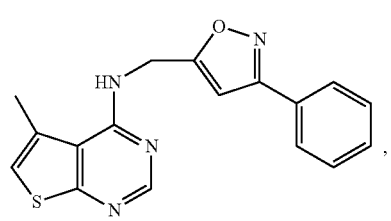
S-11
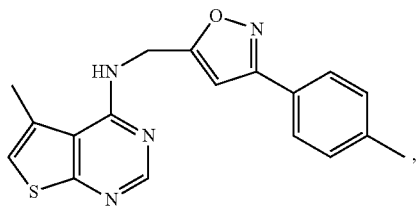
S-12
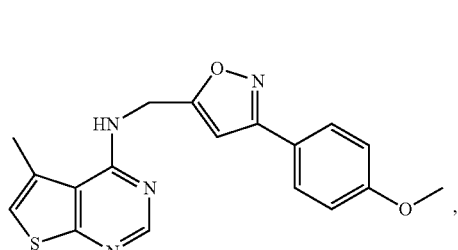
S-13
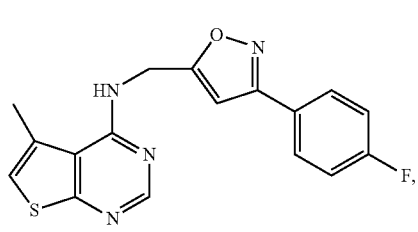
S-14
-continued
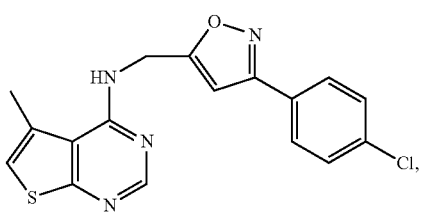
S-15
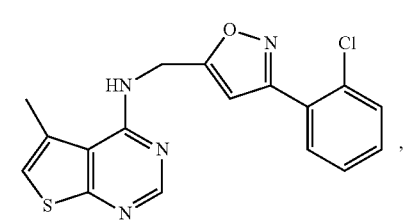
S-16
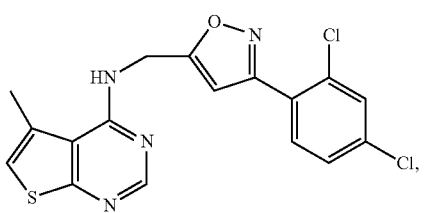
S-17
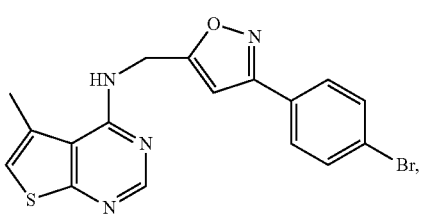
S-18
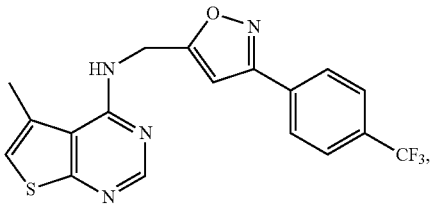
S-19
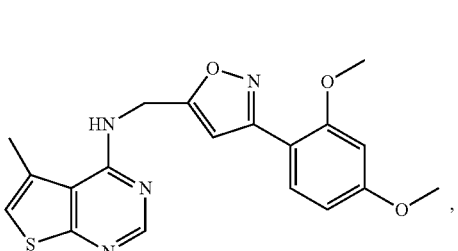
S-20
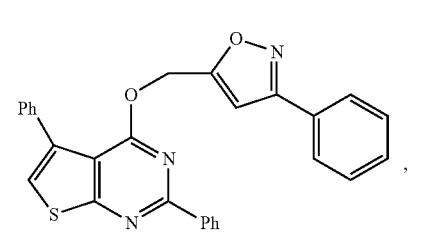
S-21

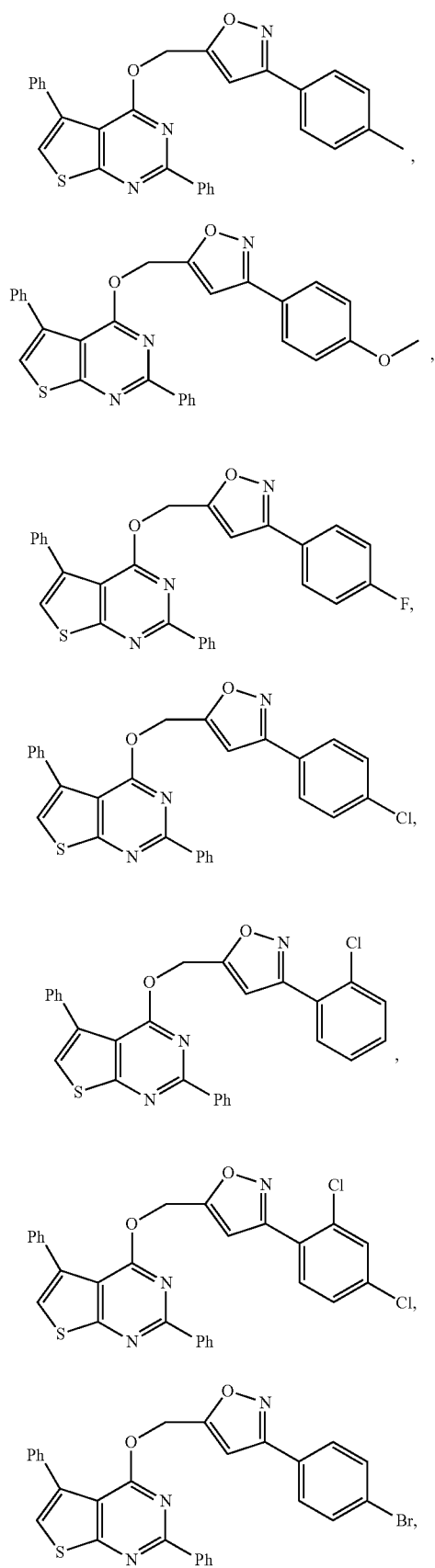
S-22
S-23
S-24
S-25
S-26
S-27
S-28
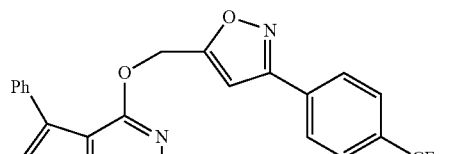
S-29
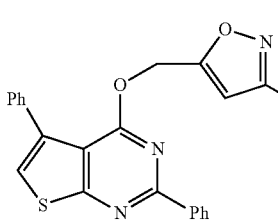
S-30
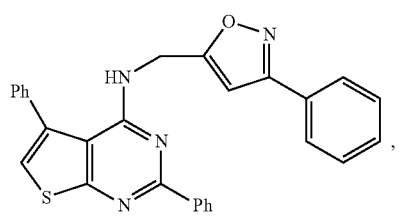
S-31
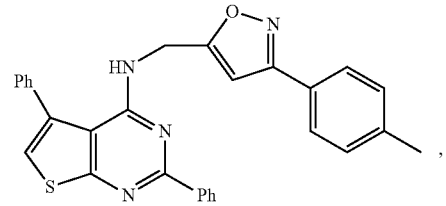
S-32
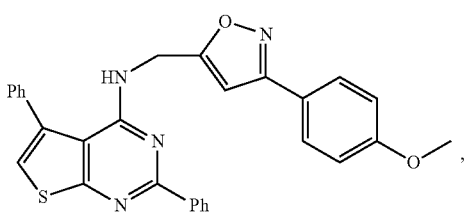
S-33
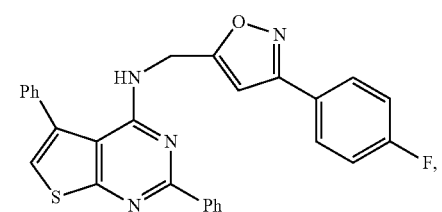
S-34
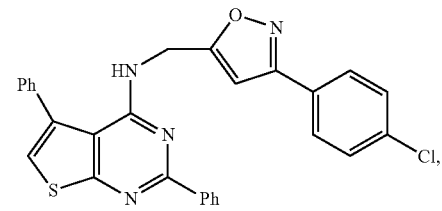
S-35

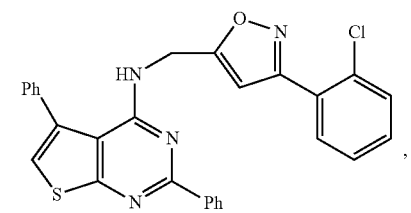 S-36
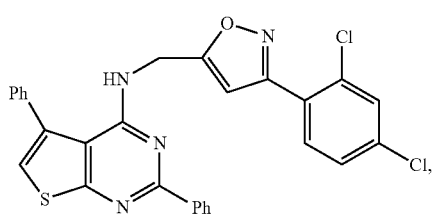 S-37
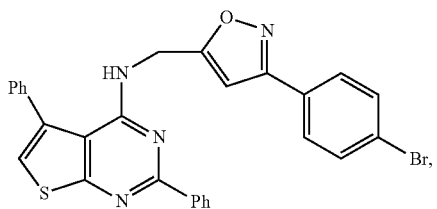 S-38
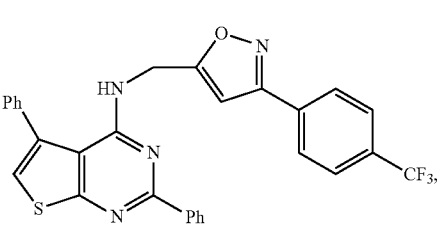 S-39
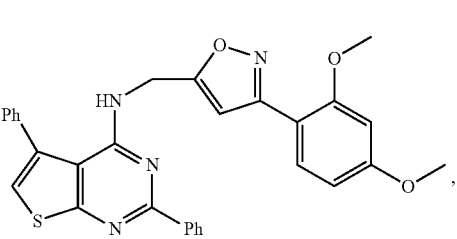 S-40
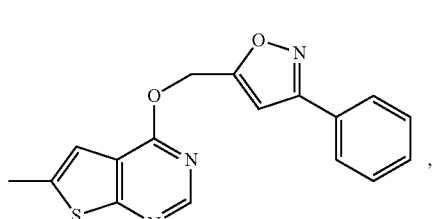 S-41
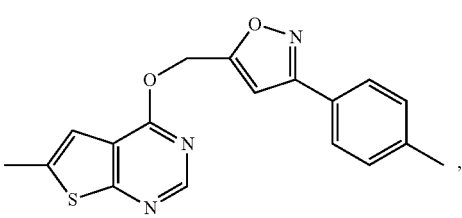 S-42
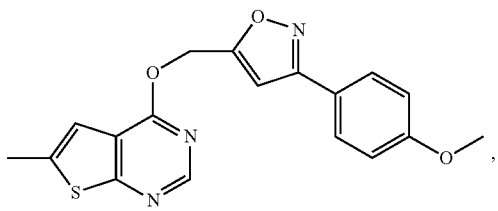 S-43
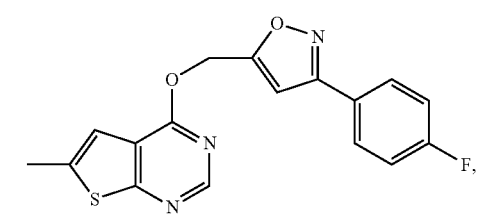 S-44
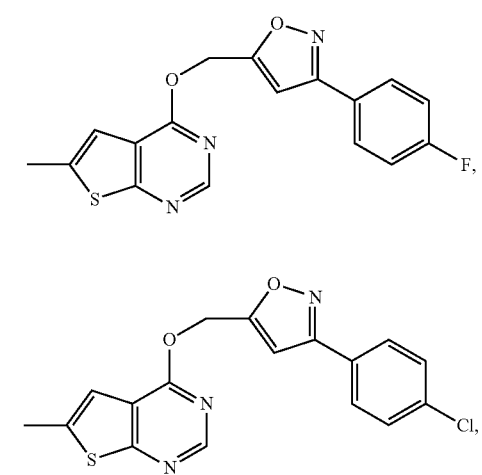 S-45
S-46
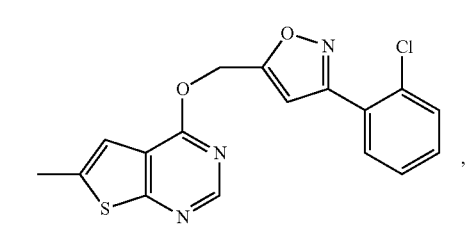 S-47
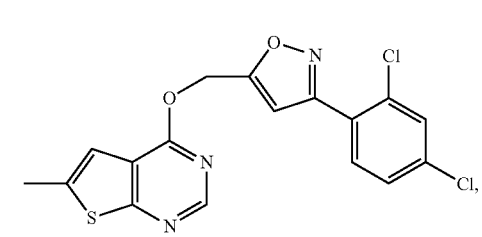 S-48
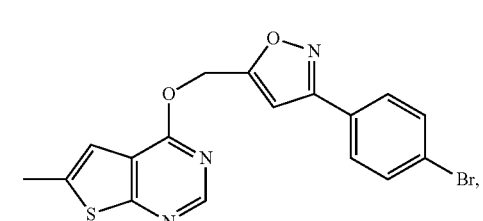 S-49
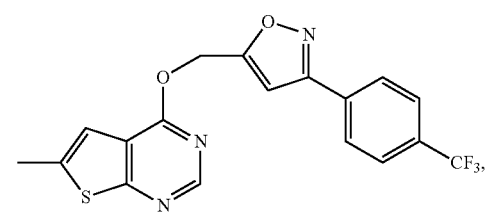

S-50 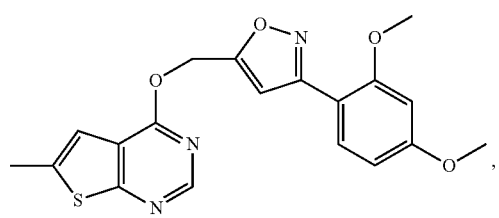
S-51 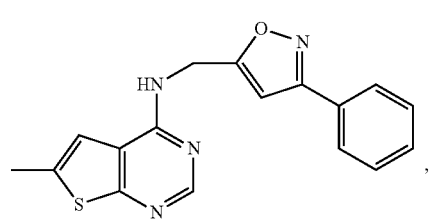
S-52 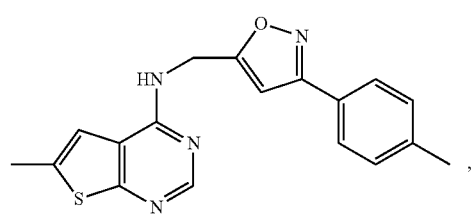
S-53 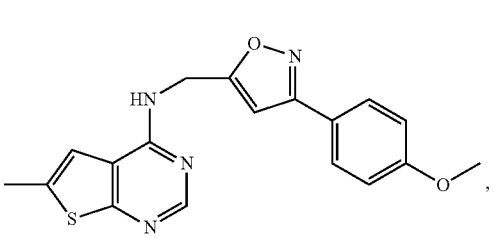
S-54 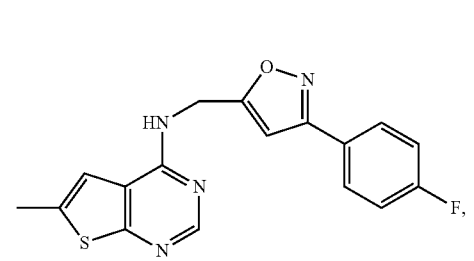
S-55 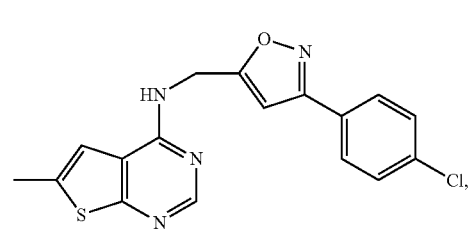
S-56 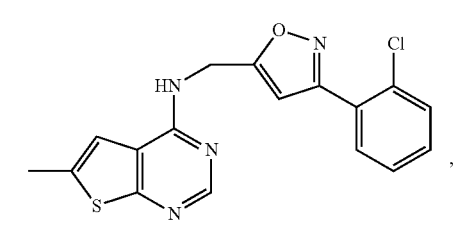
S-57 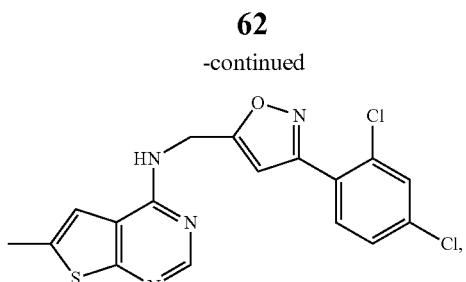
S-58 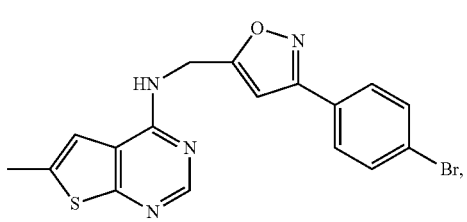
S-59 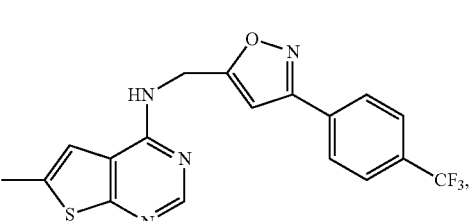
S-60 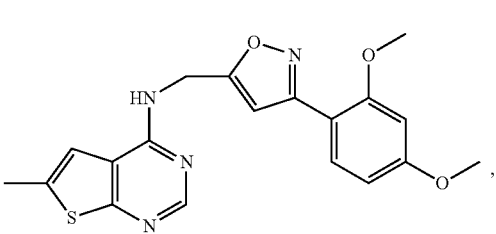
S-61 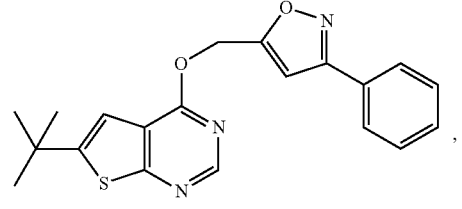
S-62 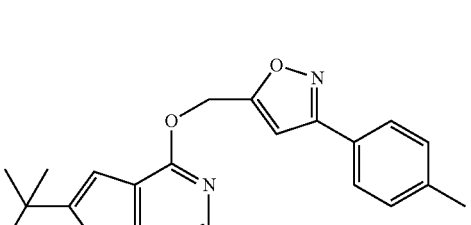
S-63 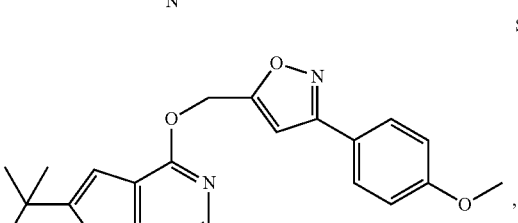

-continued

S-64, S-65, S-66, S-67, S-68, S-69, S-70

S-71, S-72, S-73, S-74, S-75, S-76, S-77

S-78
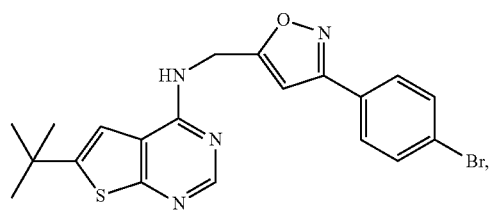
S-79
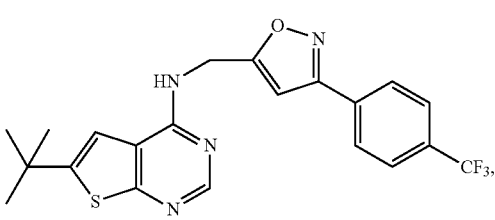
S-80
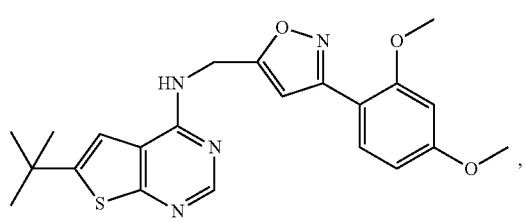
S-81
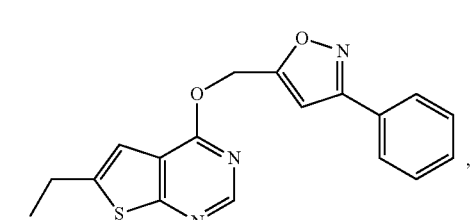
S-82
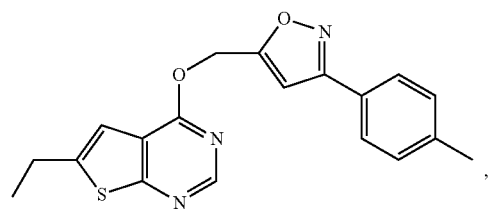
S-83
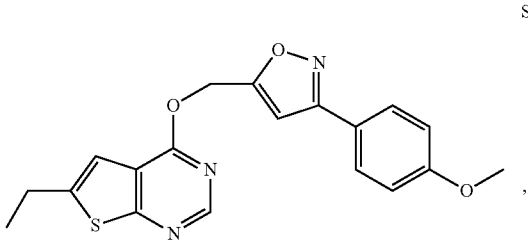
S-84
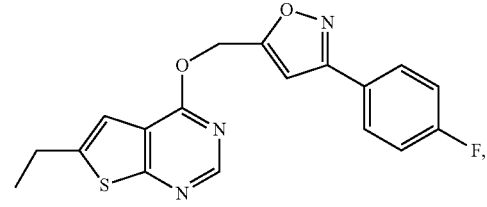
S-85
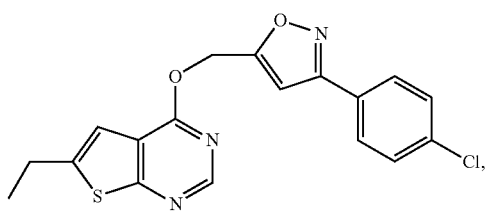
S-86
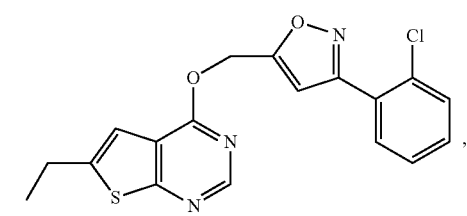
S-87
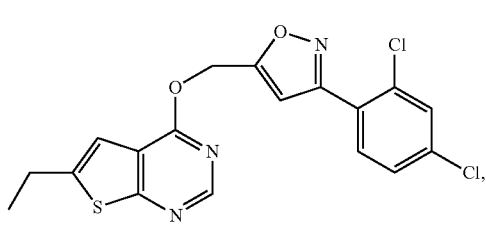
S-88
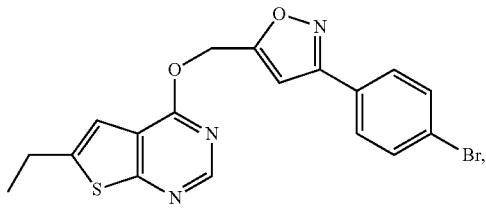
S-89
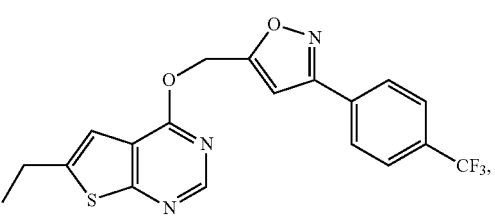
S-90
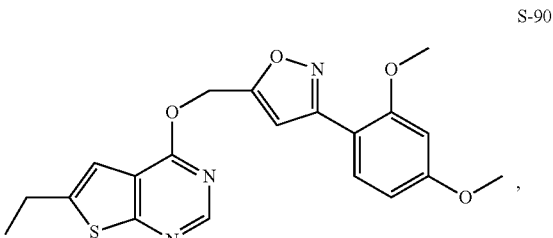
S-91
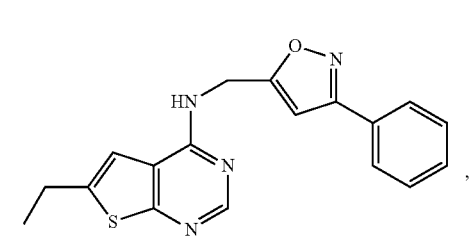

-continued
S-92
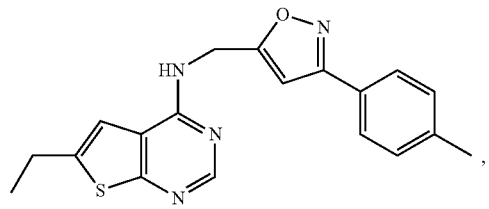
S-93
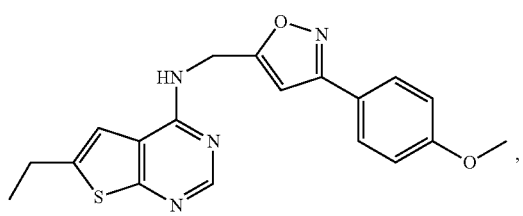
S-94
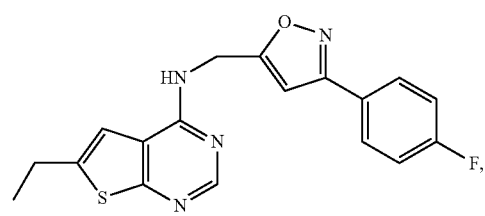
S-95
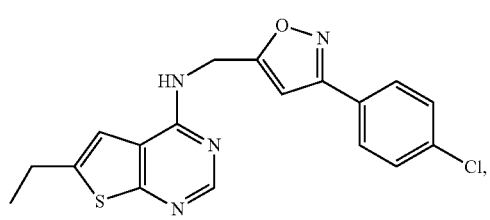
S-96
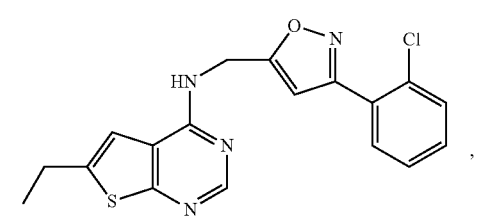
S-97
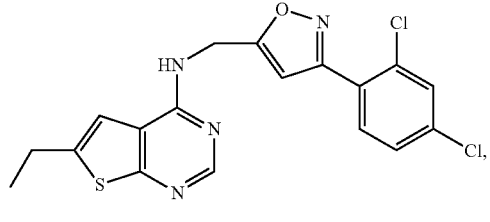
S-98
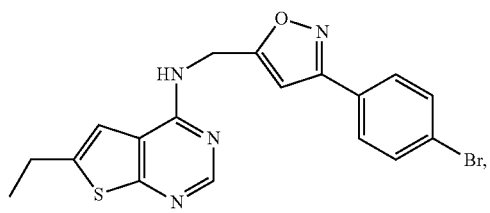
-continued
S-99
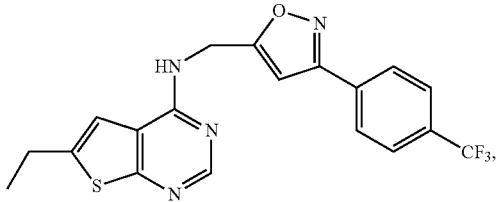
S-100
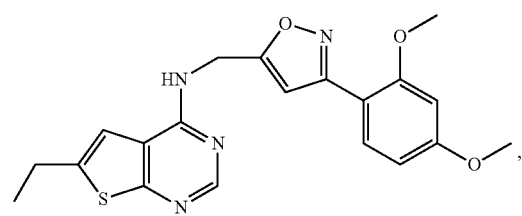
S-101
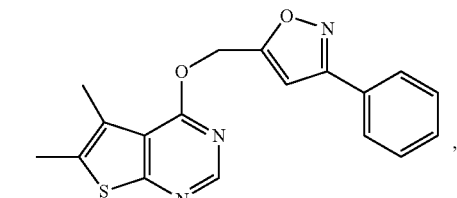
S-102
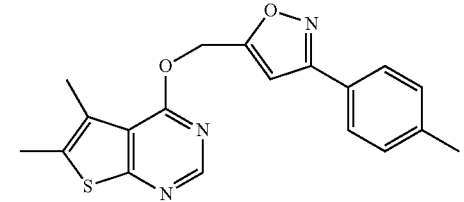
S-103
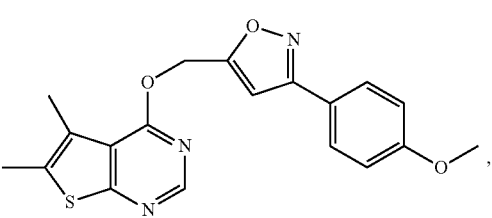
S-104
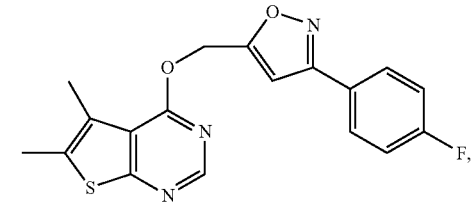
S-105
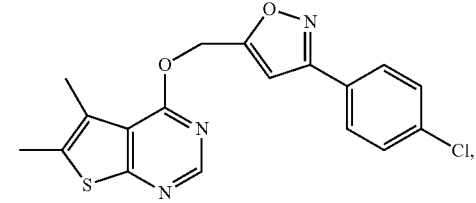

S-106
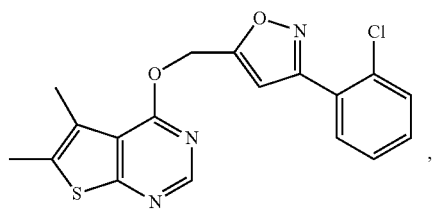
S-107
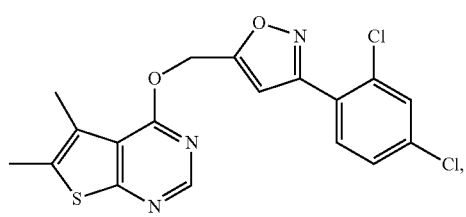
S-108
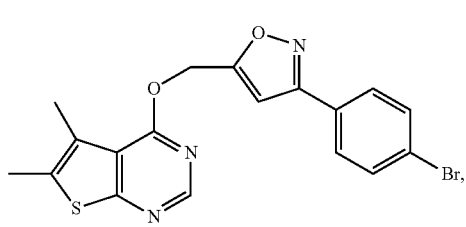
S-109
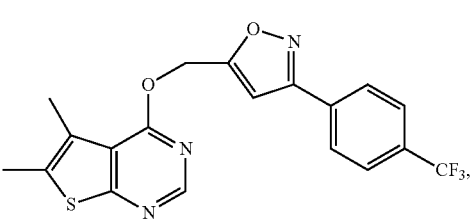
S-110
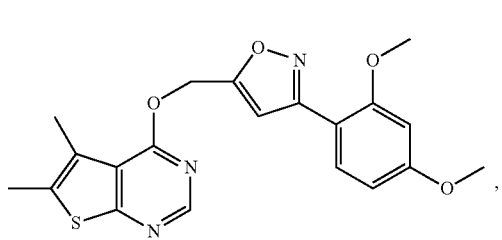
S-111
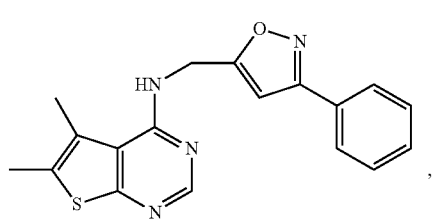
S-112
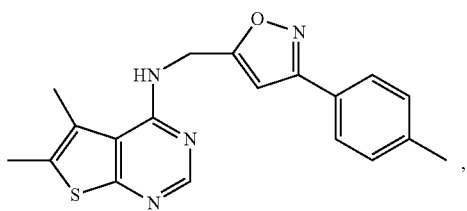
S-113
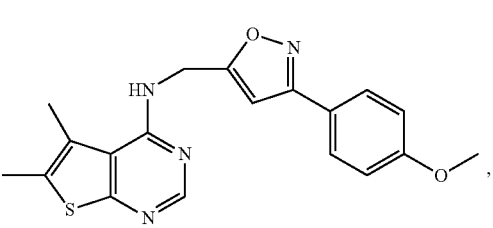
S-114
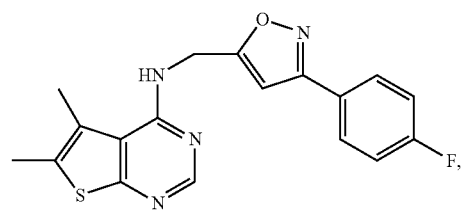
S-115
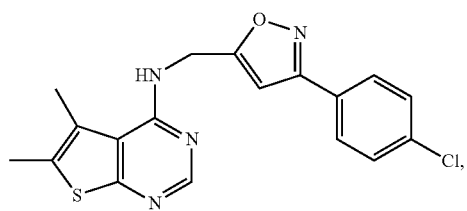
S-116
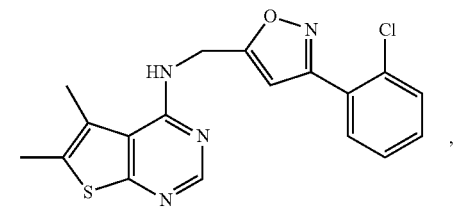
S-117
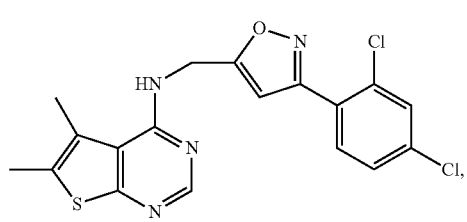

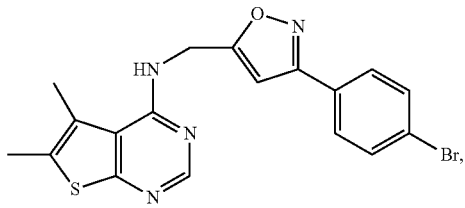
S-118

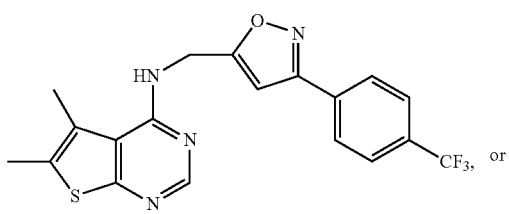
S-119

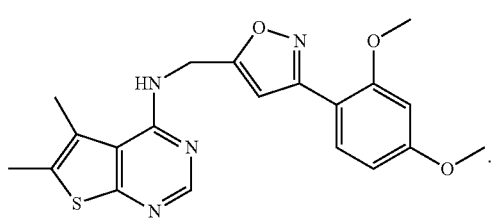
S-120

5. A pharmaceutical composition comprising:

the thieno[2,3-d]pyrimidine compound and/or the pharmaceutically acceptable salt or solvate thereof according to claim 1, and at least one pharmaceutically acceptable, inert, non-toxic excipient or carrier or diluent.

6. The pharmaceutical composition according to claim 5, wherein said pharmaceutical composition is a formulation selected from tablet, dispersible tablet, enteric coated tablet, chewable tablet, orally disintegrating tablet, capsule, granule, oral solution, hydro-acupuncture for injection, lyophilized powder for injection, large volume infusion, or small volume infusion.

7. A method for treating tumors or cancers in a human subject comprising administering to the subject an effective amount of the thieno[2,3-d]pyrimidine compound, and/or the pharmaceutically acceptable salt or solvate thereof according to claim 1, wherein the tumors or cancers is lung cancer or colon cancer.

8. A method for inhibiting an overexpression and/or overactivity of EGFR, comprising preparing an inhibitor comprising an effective amount of the thieno[2,3-d]pyrimidine compound, and/or the pharmaceutically acceptable salt or solvate thereof according to claim 1.

9. A preparation method of the thieno[2,3-d]pyrimidine compound of formula (I) according to claim 1, comprising:

reacting 2,5,6-trisubstituted-4-chloro-thieno[2,3-d]pyrimidine (formula II) and 3-substituted phenyl-5-hydroxymethyl-isoxazole (formula III) or 3-substituted phenyl-5-aminomethyl-isoxazole (formula VI) in a system comprising a dry organic solvent and an alkaline acid binding agent;

obtaining a compound of formula I-1 or I-2, respectively, wherein the reaction is schematically represented as follows:

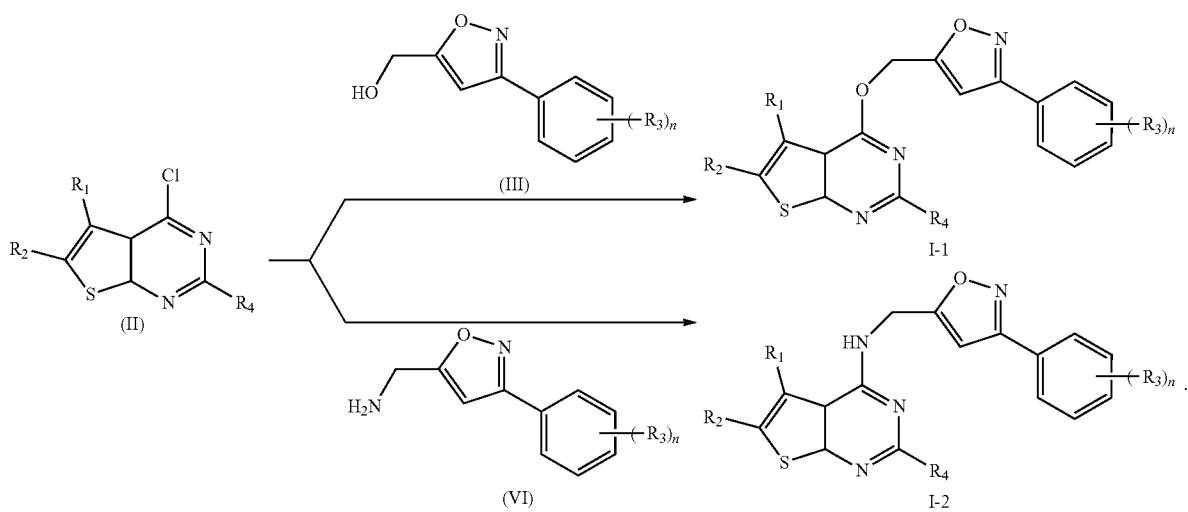

10. The thieno[2,3-d]pyrimidine compound, or the pharmaceutically acceptable salt or solvate thereof according to claim 3, wherein:

$R_1$ is selected from H, methyl, or phenyl and $R_2$ is selected from H, methyl, ethyl or tert-butyl;

Z is —NH— or —O—;

$R_3$ is at the ortho- or para-position in the isoxazole ring, and is selected from 4-fluoro, 4-chloro, 2-chloro, 4-bromo, 2,4-dichloro, 4-methyl, 4-methoxy, H, 4-trifluoromethyl, or 2,4-dimethoxy; and $R_4$ is selected from H, methyl, or phenyl.

11. The pharmaceutical composition of claim 5, further comprising one or more pharmaceutically acceptable auxiliary materials selected from fillers, disintegrants, lubricants, glidants, effervescents, flavoring agents, preservatives, or coating materials.

* * * * *